United States Patent [19]
Lassen et al.

[11] Patent Number: 6,039,942
[45] Date of Patent: Mar. 21, 2000

[54] PHYTASE POLYPEPTIDES

[75] Inventors: Soren Flensted Lassen, Copenhagen; Lisbeth Bech, Hillerod; Anders Ohmann, Bronshoj; Jens Breinholt, Bagsvaerd; Claus Crone Fuglsang, Niva; Peter Rahbek Ostergaard, Virum, all of Denmark

[73] Assignee: Novo Nordick A/S, Bagsvaerd, Denmark

[21] Appl. No.: 08/993,359

[22] Filed: Dec. 18, 1997

Related U.S. Application Data

[60] Provisional application No. 60/046,082, May 9, 1997, provisional application No. 60/046,081, May 9, 1997, and provisional application No. 60/067,304, Dec. 4, 1997.

[30] Foreign Application Priority Data

| Dec. 20, 1996 | [DK] | Denmark | 1480/96 |
| Dec. 20, 1996 | [DK] | Denmark | 1481/96 |
| Mar. 18, 1997 | [DK] | Denmark | 0301/97 |
| May 7, 1997 | [DK] | Denmark | 0529/97 |
| Dec. 1, 1997 | [DK] | Denmark | 1388/97 |

[51] Int. Cl.$^7$ .............................. A61K 38/46; C12N 9/14; C12N 1/20; C12N 15/00
[52] U.S. Cl. ........................ 424/94.6; 435/195; 435/196; 435/252.3; 435/320.1; 435/18; 536/23.2; 536/23.7; 530/300; 530/350
[58] Field of Search ........................ 424/94.6; 435/195, 435/18, 196, 252.3, 320.1; 536/23.2, 23.7; 530/300, 350

[56] References Cited

FOREIGN PATENT DOCUMENTS 0 684 313   11/1995   European Pat. Off. .

OTHER PUBLICATIONS

C. McElhinney et al., (1993) Mycol. Res. 97(6):725–732.
PIR Database No. Pirl:Jn0482, Accesssion No. JN0482.

*Primary Examiner*—Robert A. Wax
*Assistant Examiner*—Tekchand Saidha
*Attorney, Agent, or Firm*—Steve T. Zelson, Esq.; Reza Green, Esq.

[57] ABSTRACT

The present invention relates to isolated polypeptides having phytase activity, the corresponding cloned DNA sequences, a process for preparing such polypeptides, and the use thereof for a number of industrial applications. In particular, the invention relates to phytases derived from the phyllum Basidiomycota, phytases of certain consensus sequences and fungal 6-phytases.

15 Claims, 38 Drawing Sheets

1D-Ins(1)P        1L-Ins(1)P

PHYTASE POLYPEPTIDES

CROSS-REFERENCE TO RELATED APPLICATIONS

This application claims priority of U.S. provisional application Nos. 60/046,082, 60/046,081 each filed on May 9, 1997 and 60/067,304 filed on Dec. 4, 1997, and Danish application nos. 1480/96, 1481/96 each filed on Dec. 20, 1996 and 0301/97, 0529/97 and 1388/97 filed on Mar. 18, 1997, May 7, 1997 and Dec. 1, 1997, respectively, the contents of which are fully incorporated herein by reference.

FIELD OF INVENTION

The present invention relates to isolated polypeptides having phytase activity, the corresponding cloned DNA sequences, a method of producing such polypeptides, and the use thereof for a number of industrial applications. In particular, the invention relates to phytases derived from the phyllum Basidiomycota, phytases of certain consensus sequences and fungal 6-phytases.

BACKGROUND OF THE INVENTION

Phytic acid or myo-inositol 1,2,3,4,5,6-hexakis dihydrogen phosphate (or for short myo-inositol hexakisphosphate) is the primary source of inositol and the primary storage form of phosphate in plant seeds. In fact, it is naturally formed during the maturation of seeds and cereal grains. In the seeds of legumes it accounts for about 70% of the phosphate content and is structurally integrated with the protein bodies as phytin, a mixed potassium, magnesium and calcium salt of inositol. Seeds, cereal grains and legumes are important components of food and feed preparations, in particular of animal feed preparations. But also in human food cereals and legumes are becoming increasingly important.

The phosphate moieties of phytic acid chelates divalent and trivalent cations such as metal ions, i.a. the nutritionally essential ions of calcium, iron, zinc and magnesium as well as the trace minerals mangane, copper and molybdenum.

Besides, the phytic acid also to a certain extent binds proteins by electrostatic interaction. At a pH below the isoelectric point, pI, of the protein, the positively charged protein binds directly with phytate. At a pH above pI, the negatively charged protein binds via metal ions to phytate.

Phytic acid and its salts, phytates, are often not metabolized, since they are not absorbable from the gastro intestinal system, i.e. neither the phosphorous thereof, nor the chelated metal ions, nor the bound proteins are nutritionally available.

Accordingly, since phosphorus is an essential element for the growth of all organisms, food and feed preparations need to be supplemented with inorganic phosphate. Quite often also the nutritionally essential ions such as iron and calcium, must be supplemented. And, besides, the nutritional value of a given diet decreases, because of the binding of proteins by phytic acid. Accordingly, phytic acid is often termed an anti-nutritional factor.

Still further, since phytic acid is not metabolized, the phytate phosphorus passes through the gastrointestinal tract of such animals and is excreted with the manure, resulting in an undesirable phosphate pollution of the environment resulting e.g. in eutrophication of the water environment and extensive growth of algae.

Phytic acid or phytates, said terms being, unless otherwise indicated, in the present context used synonymously or at random, are degradable by phytases.

In most of those plant seeds which contain phytic acid, endogenous phytase enzymes are also found. These enzymes are formed during the germination of the seed and serve the purpose of liberating phosphate and, as the final product, free myo-inositol for use during the plant growth.

When ingested, the food or feed component phytates are in theory hydrolyzable by the endogenous plant phytases of the seed in question, by phytases stemming from the microbial flora in the gut and by intestinal mucosal phytases. In practice, however the hydrolyzing capability of the endogenous plant phytases and the intestinal mucosal phytases, if existing, is far from sufficient for increasing significantly the bioavailibility of the bound or constituent components of phytates. However, when the process of preparing the food or feed involve germination, fermentation or soaking, the endogenous phytase might contribute to a greater extent to the degradation of phytate.

In ruminant or polygastric animals such as horses and cows the gastro intestinal system hosts microorganisms capable of degrading phytic acid. However, this is not so in monogastric animals such as human beings, poultry and swine. Therefore, the problems indicated above are primarily of importance as regards such monogastric animals.

The production of phytases by plants as well as by microorganisms has been reported. Amongst the microorganisms, phytase producing bacteria as well as phytase producing fungi are known.

From the plant kingdom, e.g. a wheat-bran phytase is known (Thomlinson et al, Biochemistry, 1 (1962), 166–171). An alkaline phytase from lilly pollen has been described by Barrientos et al, Plant. Physiol., 106 (1994), 1489–1495.

Amongst the bacteria, phytases have been described which are derived from *Bacillus subtilis* (Paver and Jagannathan, 1982, *Journal of Bacteriology* 151:1102–1108) and Pseudomonas (Cosgrove, 1970, *Australian Journal of Biological Sciences* 23:1207–1220). Still further, a phytase from *E. coli* has been purified and characterized by Greiner et al, Arch. Biochem. Biophys., 303, 107–113, 1993). However, this enzyme is probably an acid phosphatase.

Phytase producing yeasts are also described, such as *Saccharomyces cerevisiae* (Nayini et al, 1984, *Lebensmittel Wissenschaft und Technologie* 17:24–26. However, this enzyme is probably a myo-inositol monophosphatase (Wodzinski et al, Adv. Appl. Microbiol., 42, 263–303). AU-A-24840/95 describes the cloning and expression of a phytase of the yeast *Schwanniomyces occidentalis*.

There are several descriptions of phytase producing filamentous fungi, however only belonging to the fungal phyllum of Ascomycota (ascomycetes). In particular, there are several references to phytase producing ascomycetes of the Aspergillus genus such as *Aspergillus terreus* (Yamada et al., 1986, *Agric. Biol. Chem.* 322:1275–1282). Also, the cloning and expression of the phytase gene from *Aspergillus niger* var. *awamori* has been described (Piddington et al., 1993, *Gene* 133:55–62). EP 0 420 358 describes the cloning and expression of a phytase of *Aspergillus ficuum* (*niger*). EP 0 684 313 describes the cloning and expression of phytases of the ascomycetes *Myceliophthora thermophila* and *Aspergillus terreus*.

Nomenclature and Position Specificity of Phytases

In the present context a phytase is an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate. In the following, for short, the above compounds are sometimes referred to as IP6, I, IP1, IP2, IP3, IP4, IP5 and P, respectively. This means that by action of a phytase, IP6 is degraded into P+one or more of the components IP5, IP4, IP3, IP2, IP1 and I. Alternatively, myo-inositol carrying in total n phosphate groups attached to positions p, q, r, . . . is denoted Ins(p,q,r, . . . )$P_n$. For convenience Ins(1,2,3,4,5,6)$P_6$ (phytic acid) is abbreviated PA.

According to the Enzyme nomenclature database ExPASy (a repository of information relative to the nomenclature of enzymes primarily based on the recommendations of the Nomenclature Committee of the International Union of Biochemistry and Molecular Biology (IUBMB) describing each type of characterized enzyme for which an EC (Enzyme Commission) number has been provided), two different types of phytases are known: A so-called 3-phytase (myo-inositol hexaphosphate 3-phosphohydrolase, EC 3.1.3.8) and a so-called 6-phytase (myo-inositol hexaphosphate 6-phosphohydrolase, EC 3.1.3.26). The 3-phytase hydrolyses first the ester bond at the 3-position, whereas the 6-phytase hydrolyzes first the ester bond at the 6-position.

Inositolphosphate Nomenclature

Considering the primary hydrolysis products of a phytase acting on phytic acid, some of the resulting esters are diastereomers and some are enantiomers. Generally, it is easier to discriminate between diastereomers, since they have different physical properties, whereas it is much more difficult to discriminate between enantiomers which are mirror images of each other.

Thus, Ins(1,2,4,5,6)$P_5$ (3-phosphate removed) and Ins(1,2,3,4,5)$P_5$ (6-phosphate removed) are diastereomers and easy to discriminate, whereas Ins(1,2,4,5,6)$P_5$ (3-phosphate removed) and Ins(2,3,4,5,6)$P_5$ (1-phosphate removed) are enantiomers. The same holds true for the pair Ins(1,2,3,4,5)$P_5$ (6-phosphate removed) and Ins(1,2,3,5,6)$P_5$ (4-phosphate removed). Accordingly, of the 6 penta-phosphate esters resulting from the first step of the phytase catalyzed hydrolysis of phytic acid, you can only discriminate easily between those esters in which the 2-, 3-, 5- and 6-phosphate has been removed, i.e. you have four diastereomers only, each of the remaining two esters being an enantiomer of one each of these compounds (4- and 6- are enantiomers, as are 1- and 3-).

Use of Lowest-Locant Rule

It should be noted here, that when using the notations Ins(2,3,4,5,6)$P_5$ and Ins(1,2,3,5,6)$P_5$, a relaxation of the previous recommendations on the numbering of the atoms of myo-inositol has been applied. This relaxation of the lowest-locant rule is recommended by the Nomenclature Committee of the International Union of Biochemistry (Biochem. J. (1989) 258, 1–2) whenever authors wish to bring out structural relationships.

In this lowest-locant rule, the L- and D-nomenclature is recommended: Inositolphosphate, phosphate esters of myo-inositol, are generally designated 1D- (or 1L-)Ins(r,s,t,u,w,x)$P_n$, n indicating the numer of phosphate groups and the locants r,s,t,u,w and x, their positions. The positions are numbered according to the Nomenclature Committee of the International Union of Biochemistry (NC-IUB) cited above (and the references herein), and 1D or 1L is used so as to make a substituent have the lowest possible locant or number ("lowest-locant rule"). Accordingly, 1L-myo-inositol-1-phosphate (1L-Ins(1)P, an intermediary product in the biosynthesis of inositol) and 1D-myo-inositol-1-phosphate (1D-Ins(1)P, a component of phospholipids), are numbered as it is apparent from FIG. 38.

Phytase Specificity

As said above, phytases are divided according to their specificity in the initial hydrolysis step, viz. according to which phosphate-ester group is hydrolyzed first.

As regards the specificity of known phytases, plant phytases are generally said to be 6-phytases. However the lilly pollen phytase is said to be a 5-phytase. The microorganism derived phytases are mainly said to be 3-phytases. E.g. the ExPASy database mentioned above refers for 3-phytases to four phytases of *Aspergillus awamori* (strain ALK0243) and *Aspergillus niger* (strain NRRL 3135) (Gene 133:55–62 (1993) and Gene 127:87–94 (1993)).

Using now the D-/L-notation (in which the D- and L-configuration refer to the 1-position), the wheat-bran phytase hydrolyzes first the phosphate ester group in the L-6 position, whereas the 3-phytases hydrolyzes first the phosphate ester group in position D-3.

The specificity can be examined in several ways, e.g by HPLC or by NMR spectroscopy. These methods, however, do not immediately allow the discrimination between hydrolysis of e.g. the phosphate-ester groups in positions D-6 and L-6, since the products of the hydrolysis, D-Ins(1,2,3,4,5)$P_5$ and L-Ins(1,2,3,4,5)$P_5$, are enantiomers (mirror images), and therefore have identical NMR spectres.

In other words, in the present context a 6-phytase means either of a L-6- or a D-6-phytase or both, viz. a phytase being a L-6-phytase, a D-6-phytase or a ((D-6-)+(L-6-))-phytase (having both activities). The latter is sometimes also designated D/L-6-phytase.

SUMMARY OF THE INVENTION

It is an object of the present invention to provide alternative phytases, in particular with superior properties such as increased heat stability or faster release of phosphate from phytate, and which can be produced in commercially useful quantities.

The present inventors have surprisingly found a whole sub-family of fungal phytases of interesting properties. This sub-family of phytases is characterized by having a high degree of conserved regions or partial sequences in common (consensus sequences). Representatives of this sub-family have turned up to be advantageous as compared to known phytases as regards various enzyme properties, such as e.g. position specificity and specific activity.

It is presently contemplated that the phytase consensus sequences of the present invention are common to all basidiomycete phytases.

In the present context a basidiomycete means a microorganism of the phyllum Basidiomycota. This phyllum of Basidiomycota is comprised in the fungal kingdom together with e.g. the phyllum Ascomycota ("ascomycetes"). Reference can be had to Jülich, 1981, Higher Taxa of Basidiomycetes; Ainsworth & Bisby, 1995, Dictionary of the Fungi; Hansen & Knudsen (Eds.), Nordic Macromycetes, vol. 2 (1992) and 3 (1997). Alternatively, a fungal taxonomy data base (NIH Data Base (Entrez)) is available via the internet on World Wide Web at the following address: http://www3.ncbi.nlm.nih.gov/Taxonomy/tax.html.

A method of screening for such phytases using PCR is also given, as are general procedures for isolating and purifying these phytase enzyme using recombinant DNA technology.

In a first aspect, the invention relates to an isolated polypeptide having phytase activity and being derived from the phyllum Basidiomycota.

In a second aspect, the invention relates to an isolated polypeptide having phytase activity and comprising at least one of several consensus sequences.

In a third aspect, the invention relates to an isolated polypeptide having phytase activity and being encoded by a DNA sequence which hybridizes under medium to high stringency with the product of a PCR reaction using a suitable set of primers derived from alignments disclosed herein and a target sequence, e.g. a DNA library.

In a fourth aspect, the invention relates to an isolated polypeptide having 6-phytase activity and being derived from a fungus.

In a fifth aspect, the invention relates to isolated polypeptides having phytase activity and being homologous to five specific sequences.

In further aspects, the invention provides cloned DNA sequences encoding the above polypeptides, as well as vectors and host cells comprising these cloned DNA sequences.

Within the scope of the invention, in a still further aspect, is the use of the phytase of the invention for liberating inorganic phosphate from phytic acid, as well as some more specific uses, and compositions, in particular food and feed preparations and additives comprising the phytase of the invention.

Generally, terms and expressions as used herein are to be interpreted as is usual in the art. In cases of doubt, however, the definitions of the present description might be useful.

GENERAL DEFINITIONS

By the expression "an isolated polypeptide/enzyme having/exhibiting phytase activity" or "an isolated phytase" is meant any peptide or protein having phytase activity (vide below) and which is essentially free of other non-phytase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE. Sometimes such polypeptide is alternatively referred to as a "purified" phytase.

The definition of "an isolated polypeptide" also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

The expression "polypeptide or enzyme exhibiting phytase activity" or "phytase" is intended to cover any enzyme capable of effecting the liberation of inorganic phosphate or phosphorous from various myo-inositol phosphates. Examples of such myo-inositol phosphates (phytase substrates) are phytic acid and any salt thereof, e.g. sodium phytate or potassium phytate or mixed salts. Also any stereoisomer of the mono-, di-, tri-, tetra- or penta-phosphates of myo-inositol might serve as a phytase substrate.

In accordance with the above definition, the phytase activity can be determined using any assay in which one of these substrates is used. In the present context (unless otherwise specified) the phytase activity is determined in the unit of FYT, one FYT being the amount of enzyme that liberates 1 µmol inorganic ortho-phosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are described in the experimental part.

"Polypeptide homology" or "amino acid homology" is determined as the degree of identity between two sequences. The homology may suitably be determined by means of computer programs known in the art such as GAP provided in the GCG version 8 program package (Program Manual for the Wisconsin Package, Version 8, Genetics Computer Group, 575 Science Drive, Madison, Wis., U.S.A. 53711) (Needleman, S. B. and Wunsch, C. D., (1970), Journal of Molecular Biology, 48, 443–453. Using GAP with the following settings for polypeptide sequence comparison: GAP creation penalty of 5.0 and GAP extension penalty of 0.3.

In the present context a "6-phytase" means a phytase which hydrolyzes first the 6-position in phytic acid or has a preference for these positions (plural is used since this term covers two positions). In particular, more than 50% of the hydrolysis product of the first step is Ins(1,2,3,4,5)$P_5$ and/or Ins(1,2,3,5,6)$P_5$. Preferably these two compounds comprise at least 60%, more preferably at least 70%, still more preferably at least 80%, especially at least 90% and mostly preferred more than 95% of the product of the initial hydrolysis step of PA.

The other specificity terms such as e.g. "3-phytase," "(3+6)-phytase" "6D-phytase" and "6L-phytase" are to be interpreted correspondingly, including the same preferred embodiments.

The terms "a phytase encoding part of a DNA sequence cloned into a plasmid present in a deposited *E. coli* strain" and "a phytase encoding part of the corresponding DNA sequence presented in the sequence listing" are presently believed to be identical, and accordingly they may be used interchangeably.

Primarily, the term "a phytase encoding part" used in connection with a DNA sequence means that region of the DNA sequence which is translated into a polypeptide sequence having phytase activity. Often this is the region between a first "ATG" start codon ("AUG" codon in mRNA) and a stop codon ("TAA", "TAG" or "TGA") first to follow.

However, the polypeptide translated as described above often comprises, in addition to a mature sequence exhibiting phytase activity, an N-terminal signal sequence and/or a pro-peptide sequence. Generally, the signal sequence guides the secretion of the polypeptide and the pro-peptide guides the folding of the polypeptide. For further information see Egnell, P. et al. Molecular Microbiol. 6(9):1115–19 (1992) or Stryer, L., "Biochemistry" W.H., Freeman and Company/New York, ISBN 0-7167-1920-7. Therefore, the term "phytase encoding part" is also intended to cover the DNA sequence corresponding to the mature part of the translated polypeptide or to each of such mature parts, if several exist.

Still further, any fragment of such sequence encoding a polypeptide fragment, which still retains some phytase activity, is to be included in this definition.

An isolated DNA molecule or, alternatively, a "cloned DNA sequence" "a DNA construct," "a DNA segment" or "an isolated DNA sequence" refers to a DNA molecule or sequence which can be cloned in accordance with standard cloning procedures used in genetic engineering to relocate the DNA segment from its natural location to a different site where it will be replicated. The term refers generally to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The degree of identity or "homology" between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., U.S.A. 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3.

Suitable experimental conditions for determining whether a given DNA or RNA sequence "hybridizes" to a specified nucleotide or oligonucleotide probe involves presoaking of the filter containing the DNA fragments or RNA to examine for hybridization in 5×SSC (Sodium chloride/Sodium citrate), (J. Sambrook, E. F. Fritsch, and T. Maniatis, 1989, *Molecular Cloning, A Laboratory Manual*, 2d edition, Cold Spring Harbor, N.Y.) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6–13), $^{32}$P-dCTP-labeled (specific activity>1×10$^9$ cpm/µg) probe for 12 hours at approximately 45° C.

The filter is then washed twice for 30 minutes in 2×SSC, 0.5% SDS at at least 55° C. (low stringency), at at least 60° C. (medium stringency), at at least 65° C. (medium/high stringency), at at least 70° C. (high stringency), or at at least 75° C. (very high stringency).

Molecules to which the oligonucleotide probe hybridizes under these conditions are detected using an x-ray film.

It has been found that it is possible to theoretically predict whether or not two given DNA sequences will hybridize under certain specified conditions.

Accordingly, as an alternative to the above described experimental method the determination whether or not an analogous DNA sequence will hybridize to the nucleotide probe described above, can be based on a theoretical calculation of the Tm (melting temperature) at which two heterologous DNA sequences with known sequences will hybridize under specified conditions (e.g. with respect to cation concentration and temperature).

In order to determine the melting temperature for heterologous DNA sequences (Tm(hetero)) it is necessary first to determine the melting temperature (Tm(homo)) for homologous DNA sequences.

The melting temperature (Tm(homo)) between two fully complementary DNA strands (homoduplex formation) may be determined by use of the following formula, Tm(homo)=81.5° C.+16.6 (log M)+0.41(% GC)−0.61 (% form)−500/L ("Current protocols in Molecular Biology". John Wiley and Sons, 1995), wherein "M" denotes the molar cation concentration in wash buffer,

| "%GC" | % Guanine (G) and Cytosine (C) of total number of bases in the DNA sequence, |
| --- | --- |
| "% form" | % formamid in the wash buffer, and |
| "L" | the length of the DNA sequence. |

The Tm determined by the above formula is the Tm of a homoduplex formation (Tm(homo)) between two fully complementary DNA sequences. In order to adapt the Tm value to that of two heterologous DNA sequences, it is assumed that a 1% difference in nucleotide sequence between the two heterologous sequences equals a 1° C. decrease in Tm ("Current protocols in Molecular Biology". John Wiley and Sons, 1995). Therefore, the Tm(hetero) for the heteroduplex formation is found by subtracting the homology % difference between the analogous sequence in question and the nucleotide probe described above from the Tm(homo). The DNA homology percentage to be subtracted is calculated as described herein (vide supra).

The term "vector" is intended to include such terms/objects as "nucleic acid constructs," "DNA constructs," "expression vectors" or "recombinant vectors."

The nucleic acid construct comprises a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature.

The term nucleic acid construct may be synonymous with the term expression cassette when the nucleic acid construct contains all the control sequences required for expression of a coding sequence of the present invention.

The term "coding sequence" as defined herein primarily comprises a sequence which is transcribed into mRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

In the expression vector, the DNA sequence encoding the phytase should be operably connected to a suitable promoter and terminator sequence. The promoter may be any DNA sequence which shows transcriptional activity in the host cell of choice and may be derived from genes encoding proteins which are either homologous or heterologous to the host cell. The procedures used to ligate the DNA sequences coding for the phytase, the promoter and the terminator and to insert them into suitable vectors are well known to persons skilled in the art (cf. e.g. Sambrook et al., (1989), Molecular Cloning. A Laboratory Manual, Cold Spring Harbor, N.Y.).

The recombinant expression vector may be any vector (e.g., a plasmid or virus) which can be conveniently subjected to recombinant DNA procedures and can bring about the expression of the nucleic acid sequence.

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

A "host cell" or "recombinant host cell" encompasses any progeny of a parent cell which is not identical to the parent cell due to mutations that occur during replication.

The cell is preferably transformed with a vector comprising a nucleic acid sequence of the invention followed by integration of the vector into the host chromosome.

"Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The host cell may be a unicellular microorganism, e.g., a prokaryote, or a non-unicellular microorganism, e.g., a eukaryote. Examples of a eukaryote cell is a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

Fungal cells may be transformed by a process involving protoplast formation, transformation of the protoplasts, and regeneration of the cell wall in a manner known per se.

The present invention also relates to a transgenic plant, plant part, such as a plant seed, or plant cell, which has been transformed with a DNA sequence encoding the phytase of the invention so as to express or produce this enzyme. Also compositions and uses of such plant or plant part are within the scope of the invention, especially its use as feed and food or additives therefore, along the lines of the present use and food/feed claims.

The transgenic plant can be dicotyledonous or monocotyledonous, for short a dicot or a monocot. Of primary interest are such plants which are potential food or feed components and which comprise phytic acid. A normal phytic acid level of feed components is 0.1–100 g/kg, or more usually 0.5–50 g/kg, most usually 0.5–20 g/kg. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are legumes, such as lupins, pea, bean and soybean, and cruciferous (family Brassicaceae), such as cauliflower, oil seed rape and the closely related model organism *Arabidopsis thaliana*.

Such transgenic plant etc. is capable of degrading its own phytic acid, and accordingly the need for adding such enzymes to food or feed comprising such plants is alleviated. Preferably, the plant or plant part, e.g. the seeds, are ground or milled, and possibly also soaked before being added to the food or feed or before the use, e.g. intake, thereof, with a view to adapting the speed of the enzymatic degradation to the actual use.

If desired, the plant produced enzyme can also be recovered from the plant. In certain cases the recovery from the plant is to be preferred with a view to securing a heat stable formulation in a potential subsequent pelleting process.

Examples of plant parts are stem, callus, leaves, root, fruits, seeds, tubers etc. But also any plant tissue is included in this definition.

Any plant cell, whatever the tissue origin, is included in the definition of plant cells above.

Also included within the scope of the invention are the progeny of such plants, plant parts and plant cells.

The skilled man will known how to construct a DNA expression construct for insertion into the plant in question, paying regard i.a. to whether the enzyme should be excreted in a tissue specific way. Of relevance for this evaluation is the stability (pH-stability, degradability by endogenous proteases etc.) of the phytase in the expression compartments of the plant. He will also be able to select appropriate regulatory sequences such as promoter and terminator sequences, and signal or transit sequences if required (Tague et al, Plant, Phys., 86, 506, 1988).

The plant, plant part etc. can be transformed with this DNA construct using any known method. An example of such method is the transformation by a viral or bacterial vector such as bacterial species of the genus Agrobacterium genetically engineered to comprise the gene encoding the phytase of the invention. Also methods of directly introducing the phytase DNA into the plant cell or plant tissue are known in the art, e.g. micro injection and electroporation (Gasser et al, Science, 244, 1293; Potrykus, Bio/Techn. 8, 535, 1990; Shimamoto et al, Nature, 338, 274, 1989).

Following the transformation, the transformants are screened using any method known to the skilled man, following which they are regenerated into whole plants.

These plants etc. as well as their progeny then carry the phytase encoding DNA as a part of their genetic equipment.

In general, reference is had to WO 9114782A and WO 9114772A.

*Agrobacterium tumefaciens* mediated gene transfer is the method of choice for generating transgenic dicots (for review Hooykas & Schilperoort, 1992. Plant Mol. Biol. 19: 15–38). Due to host range limitations it is generally not possible to transform monocots with the help of *A. tumefaciens*. Here, other methods have to be employed. The method of choice for generating transgenic monocots is particle bombardment (microscopic gold or tungsten particles coated with the transforming DNA) of embryonic calli or developing embryos (Christou, 1992. Plant J. 2: 275–281; Shimamoto, 1994. Curr. Opin. Biotechnol. 5: 158–162; Vasil et al., 1992. Bio/Technology 10: 667–674).

Also other systems for the delivery of free DNA into these plants, including viral vectors (Joshi & Joshi, 1991. FEBS Lett. 281: 1–8), protoplast transformation via polyethylene glycol or electroporation (for review see Potyrkus, 1991. Annu. Rev. Plant Physiol. Plant Mol. Biol. 42: 205–225), microinjection of DNA into mesophyll protoplasts (Crossway et al., 1986. Mol. Gen. Genet. 202: 79–85), and macroinjection of DNA into young floral tillers of cereal plants (de la Pena et al., 1987. Nature 325: 274–276) are preferred methods.

In general, the cDNA or gene encoding the phytase of the invention is placed in an expression cassette (e.g. Pietrzak et al., 1986. Nucleic Acids Res. 14: 5857–5868) consisting of a suitable promoter active in the target plant and a suitable terminator (termination of transcription). This cassette (of course including a suitable selection marker, see below) will be transformed into the plant as such in case of monocots via particle bombardment. In case of dicots the expression cassette is placed first into a suitable vector providing the T-DNA borders and a suitable selection marker which in turn are transformed into Agrobacterium tumefaciens. Dicots will be transformed via the Agrobacterium harbouring the expression cassette and selection marker flanked by T-DNA following standard protocols (e.g. Akama et al., 1992. Plant Cell Reports 12: 7–11). The transfer of T-DNA from Agrobacterium to the Plant cell has been recently reviewed (Zupan & Zambryski, 1995. Plant Physiol. 107: 1041–1047). Vectors for plant transformation via Agrobacterium are commercially available or can be obtained from many labs that construct such vectors (e.g. Deblaere et al., 1985. Nucleic Acids Res. 13: 4777–4788; for review see Klee et al., 1987. Annu. Rev. Plant Physiol. 38: 467–486).

Available plant promoters: Depending on the process under manipulation, organ- and/or cell-specific expression as well as appropriate developmental and environmental control may be required. For instance, it is desirable to express a phytase cDNA in maize endosperm etc. The most commonly used promoter has been the constitutive 35S-CaMV promoter Franck et al., 1980. Cell 21: 285–294). Expression will be more or less equal throughout the whole plant. This promoter has been used successfully to engineer herbicide- and pathogen-resistant plants (for review see Stitt & Sonnewald, 1995. Annu. Rev. Plant Physiol. Plant Mol. Biol. 46: 341–368). Organ-specific promoters have been reported for storage sink tissues such as seeds, potato tubers, and fruits (Edwards & Coruzzi, 1990. Annu. Rev. Genet. 24: 275–303), and for metabolic sink tissues such as meristems (Ito et al., 1994. Plant Mol. Biol. 24: 863– 878).

The medium used to culture the transformed host cells may be any conventional medium suitable for growing the host cells in question. The expressed phytase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Preferred host cells are a strain of Fusarium, Trichoderma or Aspergillus, in particular a strain of *Fusarium graminearum, Fusarium venenatum, Fusarium cerealis,* Fusarium sp. having the identifying characteristic of Fusarium ATCC 20334, as further described in PCT/US/95/07743, *Trichoderma harzianum* or *Trichoderma reesei, Aspergillus niger* or *Aspergillus oryzae.*

BRIEF DESCRIPTION OF THE DRAWINGS

In the detailed description of the invention below, reference is had to the drawings, of which FIG. 1 is the nucleotide sequence of the phyA cDNA and the deduced primary struture of PHYA phytase from *Peniophora lycii* (the signal peptide is boxed and the restriction sites used for cDNA cloning are underlined);

FIG. 2 is the nucleotide sequence of a phytase from *Agrocybe pediades,* as in FIG. 1;

FIG. 3 is the nucleotide sequence of a first phytase, PHYA1, from *Paxillus involtus,* as in FIG. 1, except for the box referring to the SignalP V1.1 prediction of the signal peptide;

FIG. 4 is the nucleotide sequence of a second phytase, PHYA2, from *Paxillus involtus,* as in FIG. 3;

FIG. 5 is the nucleotide sequence of a phytase from *Trametes pubescens,* as in FIG. 3;

FIG. 6 is an alignment of the deduced amino acid sequences of the encoded phytases of FIGS. 1–5, identical residues in at least three of the sequences being indicated by a grey box;

FIG. 7 is an alignment of the five phytases of FIG. 6 together with five known phytases which all belong to the fungal phyllum of Ascomycota, identical residues in at least seven of the sequences being indicated by a grey box;

DEPOSITIONS

Figure 8:
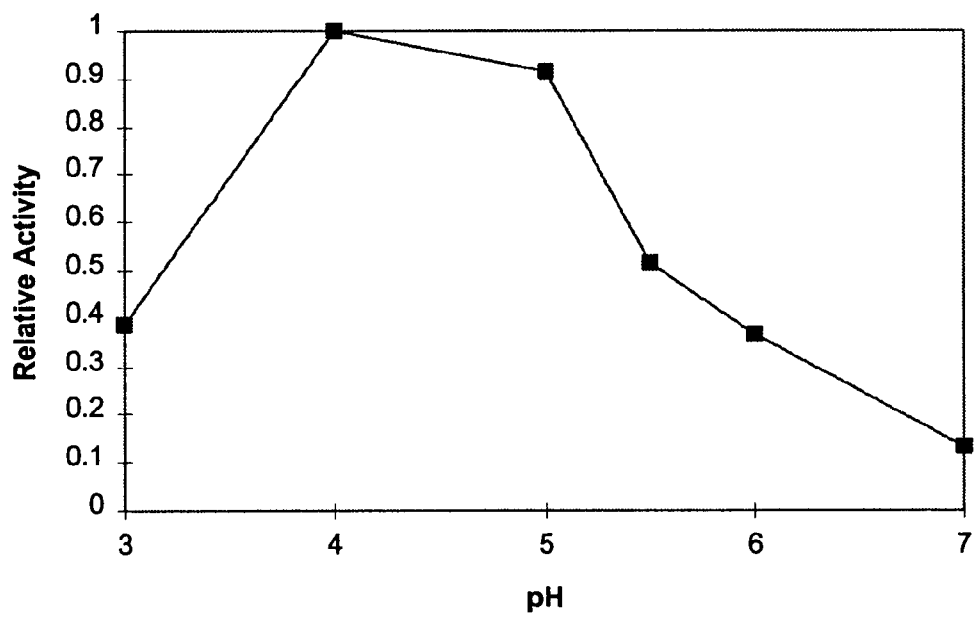
FIG. 8 is a pH-activity curve of the Peniophora phytase.
Figure 9:
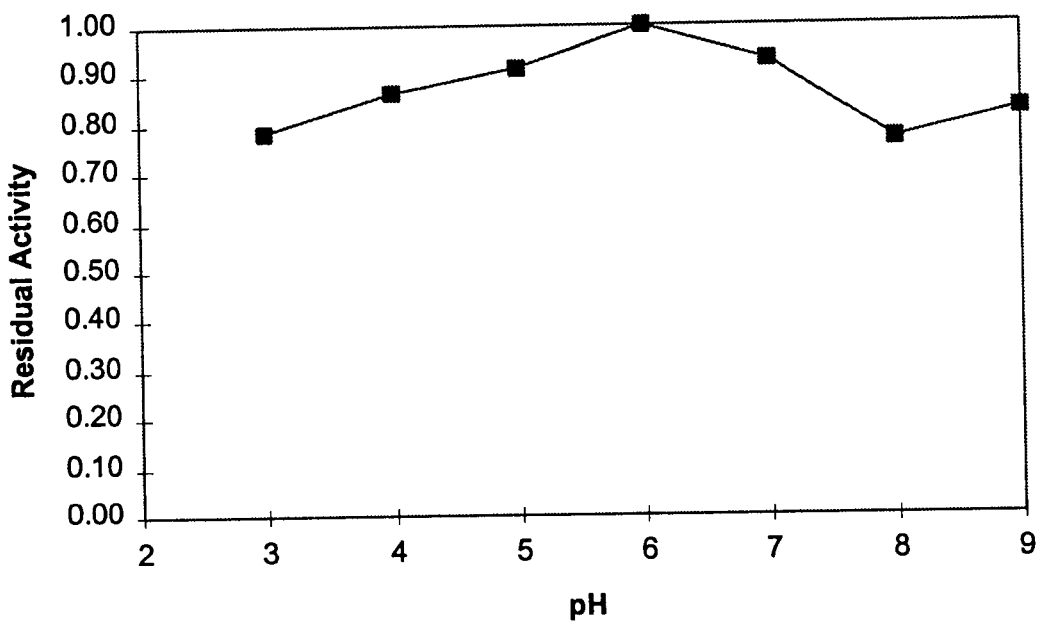
FIG. 9 a pH-stability curve thereof.
Figure 10:
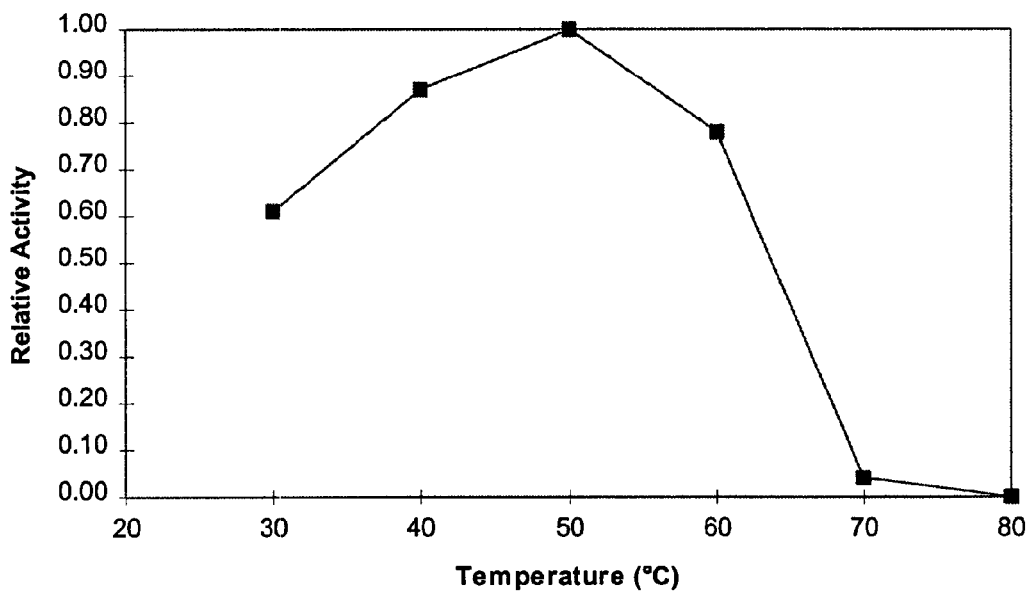
FIG. 10 a temperature-activity curve thereof.

Isolates of the strains of *Peniophora lycii, Agrocybe pediades, Paxillus involtus,* and *Trametes pubescens* from which phytases of the invention were obtained have been deposited according to the Budapest Treaty on the International Recognition of the Deposit of Microorganisms for the Purposes of Patent Procedure at the Centraalbureau voor Schimmel-cultures, P.O. Box 273, 3740 AG Baarn, The Netherlands, (CBS), as follows:

Deposit date: 4th of Dec. 1996
Depositor's ref.: NN006113
CBS No.: *Peniophora lycii* CBS No. 686.96
Deposit date: 4th of Dec. 1996
Depositor's ref.: NN009289
CBS No.: *Agrocybe pediades* CBS No. 900.96
Deposit date: 28th of Nov. 1997
Depositor's ref.: NN005693
CBS No.: *Paxillus involtus* CBS No. 100231
Deposit date: 28th of Nov. 1997
Depositor's ref.: NN009343
CBS No.: *Trametes pubescens* CBS No. 100232

Still further, the expression plasmids (shuttle vector) pYES 2.0 comprising the full length cDNA sequences encoding these phytases of the invention have been transformed into strains of *Escherichia coli* which were deposited according to the Budapest Treaty on the International Recognition of the Deposit of Microorganisms for the Purposes of Patent Procedure at the Deutsche Sammlung von Mikroorganismen und Zellkulturen GmbH., Mascheroder Weg 1b, D-38124 Braunschweig, Germany, (DSM), as follows, respectively (two phytases of *Paxillus involtus*):

Deposit date: 2nd of Dec. 1996
Depositor's ref.: NN 049282
DSM No.: *Escherichia coli* DSM No. 11312
Deposit date: 2nd of Dec. 1996
Depositor's ref.: NN 049283
DSM No.: *Escherichia coli* DSM No. 11313
Deposit date: 12th of Nov. 1997
Depositor's ref.: NN 049342
DSM No.: *Escherichia coli* DSM No. 11842
Deposit date: 12th of Nov. 1997
Depositor's ref.: NN 049343
DSM No.: *Escherichia coli* DSM No. 11843
Deposit date: 12th of Nov. 1997
Depositor's ref.: NN 049344
DSM No.: *Escherichia coli* DSM No. 11844

DETAILED DESCRIPTION OF THE INVENTION

The phytases of the invention derived from basidiomycetes are preferably derived from the classes Gasteromycetes, Hymenomycetes, Urediniomycetes, Ustilaginomycetes or from unclassified Basidiomycota, more preferably from the class Hymenomycetes.

The phytases derived from the class Hymenomycetes are preferably derived from strains of the orders Agaricales, Aphyllophorales, Auriculariales, Boletales, Cantharellales, Ceratobasidiales, Dacrymycetales, Echinodontiaceae, Hericiales, Stereales, Thelephorales, Tremellales, Tulasnellales or from the class of mitosporic Hymenomycetes.

Other preferred orders are Coriolales, Hyphodermatales, Schizophyllales, Hymenochaetales and Phanerochaetales.

Below, preferred families of some of these orders are listed, and examples of preferred genera within each family are added in parentheses behind each family.

Preferred families of the order Aphyllophorales are Polyporaceae (e.g. genus Trametes, Bjerkandera, Irpex, Oxyporus, Trichaptum, Daedalea, Fomes), Coniophoraceae (e.g. genus Coniophora), Corticiaceae (e.g. genus Hyphoderma, Trechispora, Steccherinum, Merulius, Peniophora), Schizophyllaceae (e.g. genus Schizophyllum).

Preferred families of the order Agaricales are Bolbitiaceae (e.g. genus Agrocybe, Conocybe, Bolbitius), Coprinaceae (e.g. genus Coprinus, Panaeolus), Pluteaceae (e.g. genus Volvariella), Podaxaceae (e.g. genus Podaxis), Tricholomataceae (e.g. genus Marasmiellus, Strobilurus, Lyophyllum, Cystoderma, Merismodes), Strophariaceae (e.g. genus Stropharia, Hypholoma).

A preferred family of the order Auriculariales is Exidiaceae (e.g. genus Exidia).

A preferred family of the order Dacrymetales is Dacrymycetaceae (e.g. genus Femsjonia).

Preferred families of the order Stereales are Hyphodermataceae (e.g. genus Hyphodontia) and Stereaceae (e.g. genus Amylostereum and Stereum).

A preferred family of the order Boletales is Paxillaceae (e.g. genus Paxillus and Hygrophoropsis).

A preferred family of the order Thelophorales is Thelephoraceae (e.g. genus Typhula).

Some examples of preferred strains of the above genera are *Stropharia cubensis* (in particular ATCC 13966), *Agrocybe pediades* (in particular CBS 900.96), *Bjerkandera adusta* (in particular CBS 580.95), *Trametes zonatella, Trametes pubescens* (in particular CBS 100232), *Paxillus involtus* (in particular CBS 100231), *Trametes hirsuta* (in particular DSM 2987), *Peniophora quercina, Hyphoderma argillaceum,* Scizophyllum sp. (in particular CBS 443.97), *Peniophora lycii* (in particular CBS 686.96), *Amylostereum chailletii,* Oxyporus sp. (in particular CBS 422.97). Further examples of preferred strains are listed in Example 5, Table 6.

The phytases of claim 2 have at least one of 14 partial amino acid sequences in common, the so-called consensus sequences, which are entered in the sequence listing as SEQ ID NOs: 1–14.

In the sequence listing, the amino acid three-letter-code is used, and some of the amino acids are denoted Xaa, which generally means "any amino acid" interpreted as below. In case of some of these Xaa-positions, however, a note is entered in the sequence listing to the effect that for instance X in position NN means any of two amino acids, cf. below.

In the claims, the amino acid one-letter-code is used in these sequences, and "X" denotes any amino acid including the non-naturally occuring ones and including any structurally or functionally similar variants thereof. Denotations like "[A/E]" mean any of the amino acids A and E. Accordingly, if in a partial sequence of a given formula two of such multiple choices exist, the number of sequences covered by the formula is $2^2$. Likewise, if there are "N" such multiple choices in a given formula, the number of sequences covered by this formula is $2^N$.

SEQ ID NOs: 1 to 9 are listed in the order of N-terminal to C-terminal end of the polypeptides. SEQ ID NOs: 10 to 14 are the amino acid sequences corresponding to the PCR probes specifically listed in Example 5 (viz. corresponding to the 522-sense and 540-anti-sense; 537-sense; 538-sense; 525-anti-sense and 539-anti-sense primers, respectively).

In preferred embodiments, the isolated polypeptide comprises at least two, three, four, five, six, seven, eight, nine, ten, eleven, twelve, thirteen or all fourteen sequences of SEQ ID Nos: 1–14, preferably at the positions indicated in claim 3. Claim 3 could also refer to the alignment in FIG. 6.

The sets of amino acid sequences of claim 4 reflect the PCR experiments of Examples 5 and 6 (viz. those primer-sets which are proposed).

Also some deletions seem to be characteristic for this phytase sub-family. Some regions of specific deletions are listed in claim 5. This claim could also refer to the alignment of FIG. 6.

Figure 7:
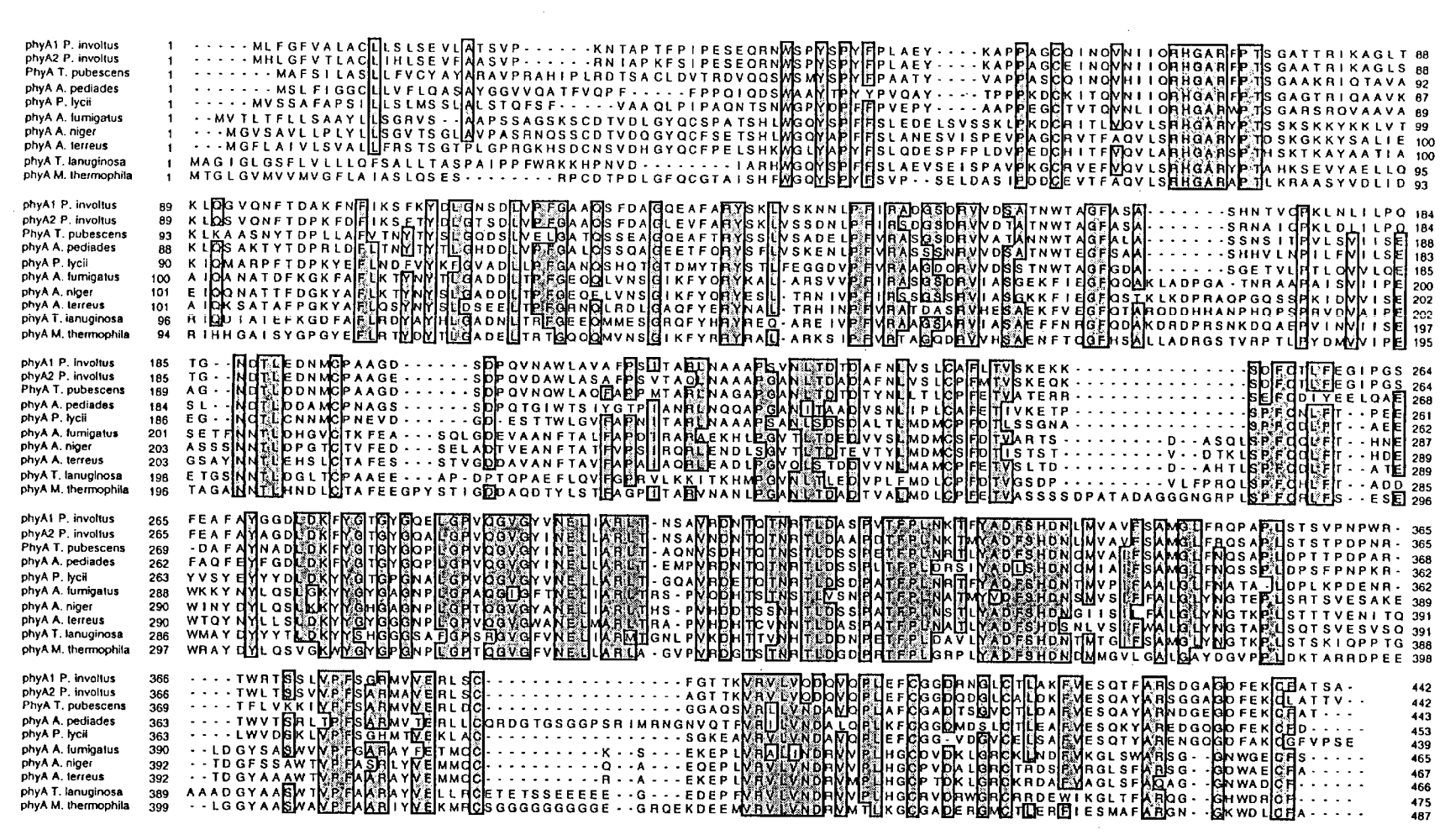

These partial sequences have been identified i.a. on the basis of the alignment shown in FIG. 7. In this alignment the five phytases at the top, viz. phyA1_*P. involtus*, phyA2_*P. involtus*, phyA_*T. pubescens*, phyA_*A. pediades* and phyA_*P. lycii*, are all derived from basidiomycetes and have been cloned as reported in the experimental section hereof. The five phytases listed at the bottom of the alignment are all derived from ascomycetes and their sequences are known from the prior art mentioned previously. Please refer to Example 4 hereof for further details and explanations with respect to the alignments, and please refer to Example 5 for one way of carrying out screening for phytases of this sub-family. Examples 8–18 describe the purification and characterization of five phytases of the invention, viz. the phytases of *Peniophora lycii, Agrocybe pediades, Paxillus involtus* and *Trametes pubescens*.

Claims 6–8 are related to the experiments of Examples 5, 6 and 7. The conditions corresponding to the term "medium to high stringency" are found in the general definition part above, viz. the washing conditions are 2×SSC and a temperature of 65° C. Preferably, the washing temperature is 65° C. or even higher, e.g. 70, 75, 80 or even 85° C., coresponding to high stringency, very high stringency or exceptionally high stringency.

Preferably, the PCR reaction is performed with a template or a target sequence, e.g. a nucleotide sequence, which can be e.g. genomic DNA or cDNA. However, for instance mRNA can also be used as a template. Genomic DNA need not be isolated, the PCR reaction can also be conducted directly on for instance fungal mycelium.

Alternatively, the PCR reaction is performed with the wild-type gene of any PE variant thereof. In particular, at least one PCR band is obtained using at least one primer set on the wild type gene.

Some specific primers for the PCR reaction are suggested in the experimental part. However, the skilled man is certainly able to propose also other specific primers from the alignment at FIG. 6 (basidiomycete phytases) which primers seem characteristic for basidiomycete phytases, i.e. he has to consider also the alignment at FIG. 7 (showing basidiomycete phytases as well as known ascomycete phytases). Therefore, claim 6 refers in general to such primers, as the skilled man would suggest be specific for basidiomycete phytases, based on his common general knowledge and the alignments at FIGS. 6 and 7.

As regards 6-phytases, the invention relates to such phytases derived from any fungus. "Fungal" is defined as described above and this term includes i.a. basidiomycetes. How to interpret the specificity is explained in the general definitions part hereof. It is noted, that in the present context, the concept of "a 6-phytase" means any of a D6-, L6- or D/L-6-phytase. Surprisingly, it has turned up that such fungal 6-phytases are of a superior performance as compared to known fungal 3-phytases, reference being had to Examples 10–12 hereof revealing the Peniophora phytase as a 6-phytase and of a highly superior performance as compared to the known Aspergillus phytases. In particular, e.g. the initial rate of hydrolysis of PA is increased and a very plausible explanation of this fact could be that this phytase is a 6-phytase, since these positions (4- and 6- in PA) are less sterically hindered than any of the other positions.

Preferably, the fungal 6-phytase is a basidiomycete phytase, still more preferably of the class, sub-class, orders, genera and strains as described at the beginning of this section headed "Detailed description of the invention." In another preferred embodiment the phytase is a D6-phytase. In another preferred embodiment the phytase is a L6-phytase.

As is apparent from claims 32–36 this application also relates to e.g. the use of a fungal 6-phytase in feed and food, compositions comprising such fungal 6-phytase, in particular food and feed additives, and the use of such fungal 6-phytase for liberating inorganic phosphate from phytic acid or phytate.

In a preferred embodiment of claims 1–8, the phytase is a (3+6)-phytase, viz. any of a D3-/D6-; L3-/L6-; D3-/L6-; L3-/D6-phytase, reference being had in particular to Examples 15–17 herein regarding the Agrocybe phytase which is also of superior performance as compared to the known Aspergillus phytase.

Preferably, the (3+6)-phytase is a basidiomycete phytase, still more preferably of the class, sub-class, orders, genera and strains as described at the beginning of this section headed "Detailed description of the invention."

Still more preferably, the (3+6)-phytase has a slight preference for one of these positions, in particular the 6-position.

The phytases of claims 11, 14, 17, 19 and 21 are all more than 50% homologous to the isolated phytases of *Agrocybe pediades, Peniophora lycii, Paxillus involtus* (phyA1 and phyA2) and *Trametes pubescens,* respectively, corresponding to SEQ ID Nos: 22, 24, 26, 28 and 30, respectively (or the mature polypeptides thereof or any fragment thereof still retaining phytase activity). For a definition of "homologous", please refer to the section headed "General definitions." The homology to known phytases appear i.a. from Table 1 in Example 4. Preferably, the number of amino acids in the fragments referred to above is at least 50%, more preferably at least 60%, still more preferably at least 70%, even more preferably at least 80%, in particular at least 90% of the number of amino acids of the sequences listed in the sequence listing. This is so also for any polypeptide fragment disclosed herein.

Preferably, all amino acid homologies of the present application are at least 55%, or at least 60%, or at least 65%, especially at least 70%. Preferably, the degree of homology is at least 80%, more preferably at least 90%, still more preferably at least 95%, especially at least 97%.

Claim 12 relates to certain fragments of the amino acid sequence of SEQ ID NO 22 derived from Agrocybe, these fragments, however, still exhibiting phytase activity. As described in more detail in the experimental part below (Examples 13–15), when expressed in yeast approximately 80% of the Agrocybe phytase enzyme has the N-terminal amino acid of Val (amino acid no. 27 in SEQ ID NO 22), whereas approximately 20% has the N-terminal amino acid of Thr (amino acid no. 25 in SEQ ID NO 22). When expressed in Aspergillus approximately ⅔ has the N-terminal amino acid of Phe (amino acid no.31 in SEQ ID NO 22), whereas approximately ⅓ has the N-terminal amino acid of Gln (amino acid no. 28 in SEQ ID NO 22). Accordingly, there are at least these four possible mature amino acid sequences.

Analogously, claim 15 relates to a fragment of the amino acid sequence of SEQ ID NO 24 derived from Peniophora, this fragment, however, still exhibiting phytase activity. As described in more detail in the experimental part below, when expressed in Aspergillus, the Peniophora phytase has an N-terminal amino acid sequence of Leu-Pro-Ile-Pro-Ala-Gln-Asn- (amino acids no. 31–37 in SEQ ID NO 24). Accordingly the sequence of amino acids nos. 31–439 of SEQ ID No 24 is presently believed to be a mature phytase sequence.

Claims 13, 16, 18, 20 and 22 are drawn to phytases homologous to the isolated phytases of *Agrocybe pediades, Peniophora lycii, Paxillus involtus* (phyA1 and phyA2) and *Trametes pubescens*, respectively.

These phytases are here defined as being encoded by a phytase encoding part of
  i) the DNA sequences listed in the sequence listing as SEQ ID Nos: 21, 23, 25, 27 and 29, respectively (phyA1 and phyA2 of *Paxillus involtus*); or
  ii) the DNA sequences cloned into plasmid pYES 2.0 present in *E. coli* DSM 11313, 11312, 11842, 11843 and 11844, respectively; or
analogues or derivatives thereof which are at least 50% homologous thereto.

For the definition of a "phytase encoding part" please refer to the general definitions section.

The five DNA sequences are obtainable directly from the deposited parent strains or from the deposited *E. coli* strains by extraction of plasmid DNA by methods known in the art (Sambrook et al. (1989) Molecular cloning: A laboratory manual, Cold Spring Harbor lab., Cold Spring Harbor, N.Y.).

Claims 23–26 relate to nucleotide sequences encoding the phytases of the invention, in particular to DNA molecules.

The DNA molecule of claim 24 comprises at least one of the specific primers suggested herein. In preferred embodiments, it comprises at least two, three, four, five or six of these sequences.

The DNA molecule of claim 25 is defined by encoding a phytase, and being selected from:
  (a) the specific nucleotide sequences of the Agrocybe, Peniophora, Paxillus and Trametes phytases (phyA1 and phyA2 of Paxillus), e.g. DNA as shown in the sequence listings having the SEQ ID nos indicated (or their complementary strands);
  (b) the same sequences as under (a) but expressed via the deposited plasmid clones;
  (c) sequences which are at least 55% homologous to these sequences;
  (d) sequences hybridizing under low stringency with the sequences of (a) or (b);
  (e) sequences which do not hybridize because of the degeneracy of the genetic code but encode the specific polypeptides or phytase active fragments thereof.

For a definition of "hybridization," please refer to the section headed "General definitions," which also lists some preferred hybridization conditions.

With respect to the homology part in feature (c), the degree of homology to the nucleic acid sequence set forth under heading (a) and (b) is at least about 55%, (still encoding an polypeptide exhibiting phytase activity). In particular, the homology is at least 60%, or at least 65%, especially at least 70%, preferably at least about 80%, more preferably at least about 90%, even more preferably at least about 95%, and most preferably at least about 97%. In particular, the degree of homology is based on a comparison with the entire sequences listed or their complementary strand or any of the sub-sequences thereof corresponding to a "mature" phytase.

The homology of the DNA of selected phytases of the invention to known phytases appear i.a. from Table 1 in Example 4.

Nucleotide claim 26 is related to polypeptide claims 6–8, and corresponding preferred embodiments mentioned with respect to these claims are hereby incorporated also with respect to this DNA claim (reference to Examples 5, 6 and 7; "medium to high stringency" means the washing conditions are 2×SSC and a temperature of 65° C., preferably 65° C. or even higher, e.g. 70, 75, 80 or even 85° C.; the PCR reaction is performed with a target nucleotide sequence, e.g. DNA, for instance genomic DNA or cDNA (or mRNA); wild-type gene of any PE variant thereof).

The DNA sequences of the invention can also be cloned by any general method involving
  cloning, in suitable vectors, a cDNA library from any organism expected to produce the phytase of interest,
  transforming suitable yeast host cells with said vectors,
  culturing the host cells under suitable conditions to express any enzyme of interest encoded by a clone in the cDNA library,
  screening for positive clones by determining any phytase activity of the enzyme produced by such clones, and
  isolating the enzyme encoding DNA from such clones.

A general isolation method has been disclosed in WO 93/11249 and WO 94/14953, the contents of which are hereby incorporated by reference. A detailed description of the screening methods is given in the experimental part.

Figure 6:
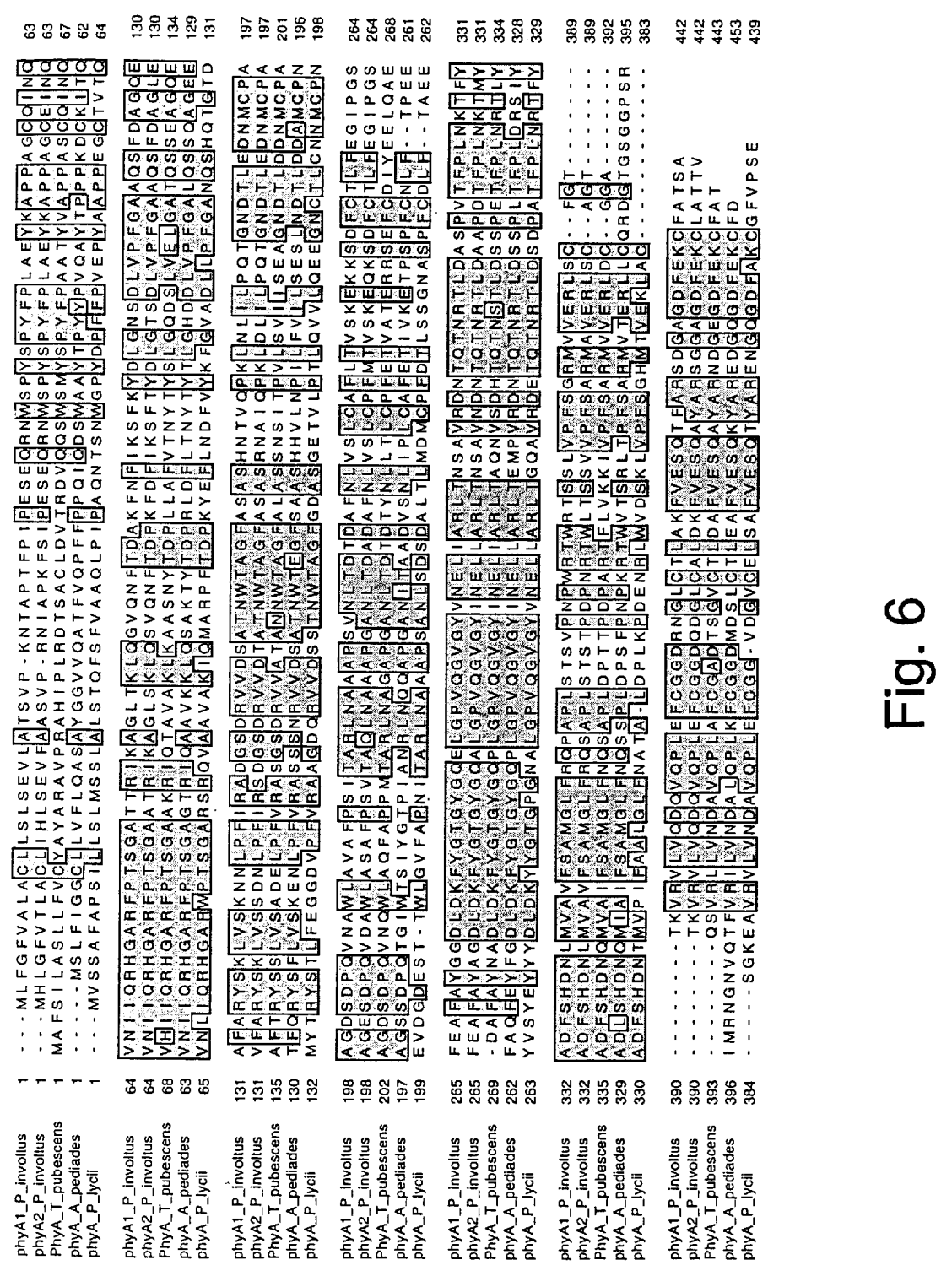

Claim 27 relates to a primer, probe, oligonucleotide molecule/DNA molecule which can be derived from the alignment of FIG. 6. Only primers specific or unique for the novel phytases of the invention are of course included herein, viz. one has to consider also the alignment at FIG. 7 (cf. remarks to claims 6–8 above).

A method of identifying further phytase producing cells, in particular microorganisms, is disclosed in claim 31. In particular, this is also a method of selecting or screening for phytase producing microorganisms. The concept of "cell" is here generally to be defined as the term "host cell" in the general definitions part hereof). Preferred cells are microorganism cells, in particular fungal cells, preferably of the phyllum Basidiomycota. More preferred basidiomycete cells are listed in the very beginning of the detailed description of the invention.

Any source, in particular any microorganism, can be selected to provide a template or a target sequence, usually in the form of genomic DNA, cDNA or mRNA.

General references to the PCR reaction, including standard reaction conditions, are found in the experimental part. As regards the selection of suitable primers, reference is had to the remarks under claims 6–8 above.

Preferably, it has to be verified that the amplified PCR fragment derived from the template is specific.

Some examples of suitable verification procedures are:

a) running an electrophoresis in agarose gels revealing the existence of a PCR band corresponding to the amplified PCR fragment; and, if desired, also b) controlling that the size of the amplified PCR-fragment is as expected; and, if desired, also c) isolating and sequencing the PCR fragment or band to show a high degree of homology to the parent sequences, from which the primers were derived.

Ad b): The potential presence of introns, (an example: 50 bases out of 300), is one of several reasons for allowing a deviation from exact size match. Preferably, the size of the amplified PCR-fragment (including introns) as measured for instance by the number of bases is within the ranges of 50–150%, 60–140%, 70–130%, 80–120%, 85–115%, 90–110%, 95–105% of the number of bases/nucleotides inbetween the primers in the parent sequences (FIG. 6), from which the primers were derived. In another preferred embodiment (excluding introns), the size of the amplified PCR-fragment is within the range of 80–120%, 85–115%, 90–110%, 95–105% of the number of bases inbetween the primers in the parent sequences (FIG. 6), from which the primers were derived.

Ad c): Preferably the degree of homology is more than 50, 60, 70, 75, 80, 85, 90, 95% homology (determined as described above). Alternatively, it is checked if the amplified PCR-fragment comprises at least one of the conserved regions inbetween the primers used, said conserved regions being shown in grey shading at FIG. 6. Preferably, the fragment comprises at least two, three, four, five etc. or all of such conserved regions. Another way of checking homology is by checking presence of areas of deletions characteristic for the parent sequences of FIG. 6. A further way of checking homology is checking characteristic distances between conserved regions, vide e.g. claim 5.

Claim 34 relates to a process for preparing the phytase polypeptide, said process logically following from this screening method of claim 31.

Steps a)+d) of claim 34 relate to the preparation of the phytase from the wild-type cell, in particular microorganism strain.

Steps b)+d) relate to the cloning of the entire phytase encoding gene from the under a) identified phytase producing cell, in particular microorganism, and transferring this gene into a heterologous or homologous host cell using any general recombinant DNA technic, e.g. as hereinbefore described and referring generally to e.g. Maniatis (cited above).

Steps c)+d) relate to the use of the amplified PCR fragment as a hybridization probe to identify and isolate phytase encoding DNA molecules (phytase encoding genes or phytase encoding parts of genes). Such DNA molecules may be isolated from any source (target sequence, template) which comprises polynucleotides, such as genomic DNA, cDNA, mRNA.

Hybridization experiments and in particular hybridization conditions, including preferred conditions, and isolation procedures are as generally hereinbefore described.

Once isolated, the DNA molecule is transferred to a host cell, as is also generally hereinbefore described.

Finally, the invention also relates generally to the use of the polypeptide according to any of claims 1–22 for liberating (or catalyzing the liberation of) phosphorous from any phytase substrate, in particular inorganic phosphate from phytate or phytic acid; alternatively for converting phytate to inorganic phosphate and (myo-inositol and/or mono-, di-, tri-, tetra-, penta-phosphate esters thereof). This claim encompasses any process wherein the phytase of the invention excerts its phytase activity as previously defined.

More specific uses according to the invention are in human food or animal feed preparations or in additives for such preparations, wherein the phytase i.a. serves the purposes of (i) reducing the phytate level of manure, (ii) improving the digestibility, promoting the growth, or improving the food and feed utilization or its conversion efficiency, i.a. by making available proteins, which would otherwise have been bound by phytate, (iii) preventing malnutrition or diseases such as anemia caused by essential ions and phosphate lacking, i.e. improving the bioavailibility of minerals or increasing the absorption thereof, eliminating the need for adding supplemental phosphate and ions etc.

In particular, the phytases of the invention can also be used in chicken food to improve egg shell quality (reduction of losses due to breaking), cf. e.g. The Merck Veterinary Manual, (Seventh edition, Merck & CO., Inc., Rahway, N.J., U.S.A., 1991; p.1268); Jeroch et al; Bodenkultur Vol. 45, No. 4 pp. 361–368 (1994); Poultry Science, Vol. 75, No. 1 pp. 62–68 (1996); Canadian Journal of Animal Science Vol. 75, No. 3 pp. 439–444 (1995); Poultry Science Vol. 74, No. 5 pp. 784–787 (1995) and Poultry Science Vol. 73, No. 10 pp. 1590–1596 (1994).

A "feed" and a "food," respectively, means any natural or artificial diet, meal or the like or components of such meals intended or suitable for being eaten, taken in, digested, by an animal and a human being, respectively.

The phytase may exert its effect in vitro or in vivo, i.e. before intake or in the stomach of the individual, respectively. Also a combined action is possible.

A phytase composition according to the invention always comprises at least one phytase of the invention.

Generally, phytase compositions are liquid or dry.

Liquid compositions need not contain anything more than the phytase enzyme, preferably in a highly purified form. Usually, however, a stabilizer such as glycerol, sorbitol or mono propylen glycol is also added. The liquid composition may also comprise other additives, such as salts, sugars, preservatives, pH-adjusting agents, proteins, phytate (a phytase substrate). Typical liquid compositions are aqueous or oil-based slurries. The liquid compositions can be added to a food or feed after an optional pelleting thereof.

Dry compositions may be spraydried compositions, in which case the composition need not contain anything more than the enzyme in a dry form. Usually, however, dry compositions are so-called granulates which may readily be mixed with e.g. food or feed components, or more preferably, form a component of a pre-mix. The particle size of the enzyme granulates preferably is compatible with that of the other components of the mixture. This provides a safe and convenient mean of incorporating enzymes into e.g. animal feed.

Agglomeration granulates are prepared using agglomeration technique in a high shear mixer (e.g. Lödige) during which a filler material and the enzyme are co-agglomerated to form granules. Absorption granulates are prepared by having cores of a carrier material to absorp/be coated by the enzyme.

Typical filler materials are salts such as disodium sulphate. Other fillers are kaolin, talc, magnesium aluminium silicate and cellulose fibres. Optionally, binders such as dextrins are also included in agglomeration granulates.

Typical carrier materials are starch, e.g. in the form of cassava, corn, potato, rice and wheat. Salts may also be used.

Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

Additionally, phytase compositions may contain other substituents such as colouring agents, aroma compounds, stabilizers, vitamins, minerals, other feed or food enhancing enzymes etc. This is so in particular for the so-called pre-mixes.

A "food or feed additive" is an essentially pure compound or a multi component composition intended for or suitable for being added to food or feed. In particular it is a substance which by its intended use is becoming a component of a food or feed product or affects any characteristics of a food or feed product. It is composed as indicated for phytase compositions above. A typical additive usually comprises one or more compounds such as vitamins, minerals or feed enhancing enzymes and suitable carriers and/or excipients.

In a preferred embodiment, the phytase compositions of the invention additionally comprises an effective amount of one or more feed enhancing enzymes, in particular feed enhancing enzymes selected from the group consisting of α-galactosidases, β-galactosidases, in particular lactases, other phytases, β-glucanases, in particular endo-β-1,4-glucanases and endo-β-1,3(4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phospholipases and cutinases.

The animal feed additive of the invention is supplemented to the mono-gastric animal before or simultaneously with the diet. Preferably, the animal feed additive of the invention is supplemented to the mono-gastric animal simultaneously with the diet. In a more preferred embodiment, the animal feed additive is added to the diet in the form of a granulate or a stabilized liquid.

An effective amount of phytase in food or feed is from about 10–20.000; preferably from about 10 to 15.000, more preferably from about 10 to 10.000, in particular from about 100 to 5.000, especially from about 100 to about 2.000 FYT/kg feed or food.

Examples of other specific uses of the phytase of the invention is in soy processing and in the manufacture of inositol or derivatives thereof.

The invention also relates to a method for reducing phytate levels in animal manure, wherein the animal is fed a feed comprising an effective amount of the phytase of the invention. As stated in the beginning of the present application one important effect thereof is to reduce the phosphate pollution of the environment.

Also within the scope of the invention is the use of a phytase of the invention during the preparation of food or feed preparations or additives, i.e. the phytase excerts its phytase activity during the manufacture only and is not active in the final food or feed product. This aspect is relevant for instance in dough making and baking.

The invention also relates to substantially pure biological cultures of the deposited microorganisms and to strains comprising, as a part of their genetic equipment, a DNA sequence encoding a phytase of the invention. Included within the definition of a substantially pure biological culture is any mutant of said strains having retained the phytase encoding capability.

The invention is described in further detail in the following examples which are not in any way intended to limit the scope of the invention.

EXAMPLES

Materials and Methods

Media

Phytate replication plates:

Add to 200 ml of melted SC agar 20 ml 20% galactose

800 µl 5% threonine 25 ml solution A 25 ml solution B

200 µl Trace element solution (DSM Catalogue 141)

Solution A:

6 g $CaCl_2$, $2H_2O$ 8 g $MgCl_2$, $6H_2O$ add $ddH_2O$ to 1l pH=6.5

Solution B:

35.12 g Na-phytate add $H_2O$ to 1l pH=6.5

Medium A:

| | |
|---|---|
| Yeast Nitrogen Base w/o Amino acids (Difco0919) | 7.5 g/l |
| Succinic acid (Merck 822260) | 11.3 g/l |
| NaOH (Merck 6498) | 6.8 g/l |
| Casamino acid w/o vitamin (Difco 0288) | 5.6 g/l |
| tryptophan (Merck 8374) | 0.1 g/l |
| Threonine | 1.0 g/l |
| Na-phytate (35.12 g/l pH 6.5) | 125 ml/l |
| Galactose | 20.0 g/l |
| Trace metal (DSM 141) | 1.0 ml/1 |
| ad 1l with $H_2O$ | |

Trace metal solution:

| | |
|---|---|
| Nitrilotriacetic acid | 1.50 g |
| $MgSO_4$, $7H_2O$ | 3.00 g |
| $MnSO_4.2H_2O$ | 0.50 g |
| NaCl | 1.00 g |
| $FeSO_4$, $7H_2O$ | 0.10 g |
| $COSO_4.7H_2O$ | 0.18 g |
| $CaCl_2$, $2H_2O$ | 0.10 g |
| $ZnSO_4$, $7H_2O$ | 0.18 g |
| $CuSO_4$, $5H_2O$ | 0.01 g |
| $KAl(SO_4)_2$, $12H_2O$ | 0.02 g |
| $H_3BO_3$ | 0.01 g |
| $Na_2MoO_4$, $2H_2O$ | 0.01 g |
| $NiCl_2$, $6H_2O$ | 0.025 g |
| $Na_2SeO$, $5H_2O$ | 0.30 g |
| Distilled water | 1 l |
| pH 7.0 | |

First dissolve nitrilotriacetic acid and adjust pH to 6.5 with KOH, then add minerals. Final pH 7.0 (with KOH).

Medium B:
Similar to medium A except for glucose is added as a C-source instead of galactose.

YPD:
10 g yeast extract, 20 g peptone, $H_2O$ to 900 ml. Autoclaved, 100 ml 20% glucose (sterile filtered) added.

YPM:
10 g yeast extract, 20 g peptone, $H_2O$ to 900 ml. Autoclaved, 100 ml 20% maltodextrin (sterile filtered) added.

10×Basal salt:
75 g yeast nitrogen base, 113 g succinic acid, 68 g NaOH, $H_2O$ ad 1000 ml, sterile filtered.

SC-URA:
100 ml 10×Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-agar:
SC-URA, 20 g/l agar added.

SC-variant agar:
20 g agar, 20 ml 10×Basal salt, $H_2O$ ad 900 ml, autoclaved

Phytase Activity Assay
The phytase activity can be measured using the following assay:

10 µl diluted enzyme samples (diluted in 0.1 M sodium acetate, 0.01% Tween20, pH 5.5) were added into 250 µl 5 mM sodium phytate (Sigma) in 0.1 M sodium acetate, 0.01% Tween20, pH 5.5 (pH adjusted after dissolving the sodium phytate; the substrate was preheated) and incubated for 30 minutes at 37° C. The reaction was stopped by adding 250 µl 10% TCA and free phosphate was measured by adding 500 µl 7.3 g $FeSO_4$ in 100 ml molybdate reagent (2.5 g $(NH_4)_6Mo_7O_{24} \cdot 4H_2O$ in 8 ml $H_2SO_4$ diluted to 250 ml). The absorbance at 750 nm was measured on 200 µl samples in 96 well microtiter plates. Substrate and enzyme blanks were included. A phosphate standard curve was also is included (0–2 mM phosphate). 1 FYT equals the amount of enzyme that releases 1 µmol phosphate/min at the given conditions.

General Molecular Biology Methods
Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Unless otherwise specified all enzymes for DNA manipulations, such as e.g. restriction endonucleases, ligases etc., were obtained from New England Biolabs, Inc. The enzymes were used according to the specifications of the suppliers.

Example 1

Cloning and Expression of a Phytase from
Peniophora lycii CBS No. 686.96

Deposited Organisms
Peniophora lycii CBS No. 686.96 comprises a phytase encoding DNA sequence of the invention.

Escherichia coli DSM NO 11312 contains the plasmid comprising the full length cDNA sequence, coding for a phytase of the invention, in the shuttle vector pYES 2.0.

Other Strains
Yeast strain: The Saccharomyces cerevisiae strain used was W3124 (van den Hazel, H. B; Kielland-Brandt, M. C.; Winther, J. R. in Eur. J. Biochem., 207, 277–283, 1992; (MATa; ura 3-52; leu 2-3, 112; his 3-D200; pep 4-1137; prc1::HIS3; prb1:: LEU2; cir+).

E. coli strain: DH10B (Life Technologies)

Plasmids
The Aspergillus expression vector pHD414 is a derivative of the plasmid p775 (described in EP 238 023). The construction of pHD414 is further described in WO 93/11249.

pYES 2.0 (Invitrogen)

pA2phy2 (See example 1)

Expression Cloning in Yeast
Expression cloning in yeast was done as described by H. Dalboege et al. (H. Dalboege et al Mol. Gen. Genet (1994) 243:253–260.; WO 93/11249; WO 94/14953), which are hereby incorporated as reference. All individual steps of Extraction of total RNA, cDNA synthesis, Mung bean nuclease treatment, Blunt-ending with T4 DNA polymerase, and Construction of libraries was done according to the references mentioned above.

Fermentation Procedure of Peniophora lycii CBS No. 686.96 for mRNA Isolation

Peniophora lycii CBS 686.96 was inoculated from a plate with outgrown mycelium into a shake flask containing 100 ml medium B (soya 30 g/l, malto dextrin 15 g/l, bacto peptone 5 g/l, pluronic 0.2 g/l). The culture was incubated stationary at 26° C. for 15 days. The resulting culture broth was filtered through miracloth and the mycelium was frozen down in liquid nitrogen.

mRNA was isolated from mycelium from this culture as described in (H. Dalboege et al Mol. Gen. Genet (1994) 243:253–260.; WO 93/11249; WO 94/14953).

Extraction of total RNA was performed with guanidinium thiocyanate followed by ultracentrifugation through a 5.7 M CsCl cushion, and isolation of poly(A)$^+$RNA was carried out by oligo(dT)-cellulose affinity chromatography using the procedures described in WO 94/14953.

cDNA Synthesis
Double-stranded cDNA was synthesized from 5 mg poly (A)$^+$RNA by the RNase H method (Gubler and Hoffman (1983) Gene 25:263–269, Sambrook et al. (1989) Molecular cloning: A laboratory manual, Cold Spring Harbor lab., Cold Spring Harbor, N.Y.). The poly(A)$^+$RNA (5 µg in 5 µl of DEPC-treated water) was heated at 70° C. for 8 min. in a pre-siliconized, RNase-free Eppendorph tube, quenched on ice and combined in a final volume of 50 µl with reverse transcriptase buffer (50 mM Tris-Cl, pH 8.3, 75 mM KCl, 3 mM $MgCl_2$, 10 mM DTT, Bethesda Research Laboratories) containing 1 mM of dATP, dGTP and dTTP and 0.5 mM 5-methyl-dCTP (Pharmacia), 40 units human placental ribonuclease inhibitor (RNasin, Promega), 1.45 µg of oligo(dT)$_{18}$-Not I primer (Pharmacia) and 1000 units SuperScript II RNase H reverse transcriptase (Bethesda Research Laboratories). First-strand cDNA was synthesized by incubating the reaction mixture at 45° C. for 1 hour. After synthesis, the mRNA:cDNA hybrid mixture was gelfiltrated through a MicroSpin S-400 HR (Pharmacia) spin column according to the manufacturer's instructions.

After the gelfiltration, the hybrids were diluted in 250 µl second strand buffer (20 mM Tris-Cl, pH 7.4, 90 mM KCl, 4.6 mM $MgCl_2$, 10 mM $(NH_4)_2SO_4$, 0.16 mM bNAD+) containing 200 µl of each dNTP, 60 units E. coli DNA polymerase I (Pharmacia), 5.25 units RNase H (Promega) and 15 units E. coli DNA ligase (Boehringer Mannheim). Second strand cDNA synthesis was performed by incubating the reaction tube at 16° C. for 2 hours and additional 15 min. at 25° C. The reaction was stopped by addition of EDTA to a final concentration of 20 mM followed by phenol and chloroform extractions.

Mung Bean Nuclease Treatment

The double-stranded cDNA was precipitated at −20° C. for 12 hours by addition of 2 vols 96% EtOH, 0.2 vol 10 M $NH_4Ac$, recovered by centrifugation, washed in 70% EtOH, dried and resuspended in 30 µl Mung bean nuclease buffer (30 mM NaAc, pH 4.6, 300 mM NaCl, 1 mM $ZnSO_4$, 0.35 mM DTT, 2% glycerol) containing 25 units Mung bean nuclease (Pharmacia). The single-stranded hair-pin DNA was clipped by incubating the reaction at 30° C. for 30 min., followed by addition of 70 µl 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-Ending With T4 DNA Polymerase

The double-stranded cDNAs were recovered by centrifugation and blunt-ended in 30 ml T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs) by incubating the reaction mixture at 16° C. for 1 hour. The reaction was stopped by addition of EDTA to a final concentration of 20 mM, followed by phenol and chloroform extractions, and precipitation for 12 hours at −20° C. by adding 2 vols 96% EtOH and 0.1 vol 3 M NaAc pH 5.2.

Adaptor Ligation, Not I Digestion and Size Selection

After the fill-in reaction the cDNAs were recovered by centrifugation, washed in 70% EtOH and dried. The cDNA pellet was resuspended in 25 µl ligation buffer (30 mM Tris-Cl, pH 7.8, 10 mM $MgCl_2$, 10 mM DTT, 0.5 mM ATP) containing 2.5 µg non-palindromic BstXI adaptors (Invitrogen) and 30 units T4 ligase (Promega) and incubated at 16° C. for 12 hours. The reaction was stopped by heating at 65° C. for 20 min. and then cooling on ice for 5 min. The adapted cDNA was digested with Not I restriction enzyme by addition of 20 µl water, 5 µl 10× Not I restriction enzyme buffer (New England Biolabs) and 50 units Not I (New England Biolabs), followed by incubation for 2.5 hours at 37° C. The reaction was stopped by heating at 65° C. for 10 min. The cDNAs were size-fractionated by gel electrophoresis on a 0.8% SeaPlaque GTG low melting temperature agarose gel (FMC) in 1× TBE to separate unligated adaptors and small cDNAs. The cDNA was size-selected with a cut-off at 0.7 kb and rescued from the gel by use of b-Agarase (New England Biolabs) according to the manufacturer's instructions and precipitated for 12 hours at −20° C. by adding 2 vols 96% EtOH and 0.1 vol 3 M NaAc pH 5.2.

Construction of Libraries

The directional, size-selected cDNA was recovered by centrifugation, washed in 70% EtOH, dried and resuspended in 30 µl 10 mM Tris-Cl, pH 7.5, 1 mM EDTA. The cDNAs were desalted by gelfiltration through a MicroSpin S-300 HR (Pharmacia) spin column according to the manufacturer's instructions. Three test ligations were carried out in 10 µl ligation buffer (30 mM Tris-Cl, pH 7.8, 10 mM $MgCl_2$, 10 mM DTT, 0.5 mM ATP) containing 5 µl double-stranded cDNA (reaction tubes #1 and #2), 15 units T4 ligase (Promega) and 30 ng (tube #1), 40 ng (tube #2) and 40 ng (tube #3, the vector background control) of BstXI-NotI cleaved pYES 2.0 vector. The ligation reactions were performed by incubation at 16° C. for 12 hours, heating at 70° C. for 20 min. and addition of 10 µl water to each tube. 1 µl of each ligation mixture was electroporated into 40 µl electrocompetent E. coli DH10B cells (Bethesda research Laboratories) as described (Sambrook et al. (1989) Molecular cloning: A laboratory manual, Cold Spring Harbor lab., Cold Spring Harbor, N.Y.). Using the optimal conditions a library was established in E. coli consisting of pools. Each pool was made by spreading transformed E. coli on LB+ampicillin agar plates giving 15.000–30.000 colonies/plate after incubation at 37° C. for 24 hours. 20 ml LB+ampicillin was added to the plate and the cells were suspended herein. The cell suspension was shaked in a 50 ml tube for 1 hour at 37° C. Plasmid DNA was isolated from the cells according to the manufacturer's instructions using QIAGEN plasmid kit and stored at −20° C.

1 µl aliquots of purified plasmid DNA (100 ng/ml) from individual pools were transformed into S. cerevisiae W3124 by electroporation (Becker and Guarante (1991) Methods Enzymol. 194:182–187) and the transformants were plated on SC agar containing 2% glucose and incubated at 30° C.

Identification of Positive Colonies

After 3–5 days of growth, the agar plates were replica plated onto a set of the phytate replication plates, and incubated for 3–5 days at 30° C. 1% LSB-agarose (Sigma) containing 0.2M CaCl2 is poured over the plates and after 1–4 days the phytase positive colonies are identified as colonies surrounded by a clearing zone.

Cells from enzyme-positive colonies were spread for single colony isolation on agar, and an enzyme-producing single colony was selected for each of the phytase-producing colonies identified.

Isolation of a cDNA Gene for Expression in Aspergillus

A phytase-producing yeast colony was inoculated into 20 ml YPD broth in a 50 ml glass test tube. The tube was shaken for 2 days at 30° C. The cells were harvested by centrifugation for 10 min. at 3000 rpm.

DNA was isolated according to WO 94/14953 and dissolved in 50 ml water. The DNA was transformed into E. coli by standard procedures. Plasmid DNA was isolated from E. coli using standard procedures, and analyzed by restriction enzyme analysis.

The cDNA insert was excised using the restriction enzymes Hind III and Xba I and ligated into the Aspergillus expression vector pHD414 resulting in the plasmid pA2phy2.

The cDNA inset of Qiagen purified plasmid DNA of pA2phy2 (Qiagen, U.S.A.) was sequenced with the Taq deoxy terminal cycle sequencing kit (Perkin Elmer, U.S.A.) and synthetic oligonucleotide primers using an Applied Biosystems ABI PRISM™ 377 DNA Sequencer according to the manufacturers instructions.

Transformation of Aspergillus oryzae or Aspergillus niger

Protoplasts are prepared as described in WO 95/02043, p. 16, line 21–page 17, line 12.

100 µl of protoplast suspension is mixed with 5–25 µg of the appropriate DNA in 10 µl of STC (1.2 M sorbitol, 10 mM Tris-HCl, pH=7.5, 10 mM $CaCl_2$). Protoplasts are mixed with p3SR2 (an A. nidulans amdS gene carrying plasmid) (Tove Christensen et al. Bio/Technology, pp 1419–1422 vol.6, December 1988). The mixture is left at room temperature for 25 minutes. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates (Cove, Biochem. Biophys. Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* Transformants

Each of the *A. oryzae* transformants are inoculated in 10 ml of YPM (cf. below) and propagated. After 2–5 days of incubation at 30° C., the supernatant is removed.

The phytase activity is identified by applying 20 μl supernatant to 4 mm diameter holes punched out in 1% LSB-agarose plates containing 0.1M Sodiumacetate pH 4.5 and 0.1%

Inositol hexaphosphoric acid. The plates are left over night at 37° C. A buffer consisting of 0.1M CaCl2 and 0.2M Sodium acetate pH 4.5 is poured over the plates and the plates are left at room temperature for 1 h. Phytase activity is then identified as a clear zone.

Fed Batch Fermentation

Fed batch fermentation was performed in a medium comprising maltodextrin as a carbon source, urea as a nitrogen source and yeast extract. The fed batch fermentation was performed by inoculating a shake flask culture of *A. oryzae* host cells in question into a medium comprising 3.5% of the carbon source and 0.5% of the nitrogen source. After 24 hours of cultivation at pH 7.0 and 34° C. the continuous supply of additional carbon and nitrogen sources were initiated. The carbon source was kept as the limiting factor and it was secured that oxygen was present in excess. The fed batch cultivation was continued for 4 days.

Isolation of the DNA Sequence Shown in SEQ ID No. 23

The phytase encoding part of the DNA sequence shown in SEQ ID No. 23 coding for the phytase of the invention can be obtained from the deposited organism *Escherichia coli* DSM 11312 by extraction of plasmid DNA by methods known in the art (Sambrook et al. (1989) Molecular cloning: A laboratory manual, Cold Spring Harbor lab., Cold Spring Harbor, N.Y.).

Cloning and expression was done by using the Expression cloning in yeast technique as described above.

mRNA was isolated from *Peniophora lycii*, CBS No. 686.96, grown as described above.

Mycelia were harvested after 15 days' growth, immediately frozen in liquid nitrogen and stored at –80° C. A library from *Peniophora lycii*, CBS No. 686.96, consisting of approx. $9 \times 10^5$ individual clones was constructed in *E. coli* as described with a vector background of 1%. Plasmid DNA from some of the pools was transformed into yeast, and 50–100 plates containing 250–400 yeast colonies were obtained from each pool.

Phytase-positive colonies were identified and isolated as described above and inoculated into 20 ml YPD broth in a 50 ml glass test tube. The tube was shaken for 2 days at 30° C. The cells were harvested by centrifugation for 10 min. at 3000 rpm. DNA was isolated according to WO 94/14953 and dissolved in 50 μl water. The DNA was transformed into *E. coli* by standard procedures. Plasmid DNA was isolated from *E. coli* using standard procedures, and the DNA sequence of the cDNA encoding the phytase was sequenced with the Taq deoxy terminal cycle sequencing kit (Perkin Elmer, U.S.A.) and synthetic oligonucleotide primers using an Applied Biosystems ABI PRISM™ 377 DNA Sequencer according to the manufacturers instructions. The DNA sequence of the cDNA encoding the phytase is shown in SEQ ID No. 23 and the corresponding amino acid sequence is shown in SEQ ID No. 24. In SEQ ID No. 23 DNA nucleotides from No 1 to No. 1320 define a phytase encoding region.

The part of the DNA sequence in SEQ ID NO 23, which is encoding the mature part of the phytase is position 91 to 1320, which corresponds to amino acid position 31–439 in SEQ ID NO 24.

The cDNA is obtainable from the plasmid in DSM 11312.

Total DNA was isolated from a yeast colony and plasmid DNA was rescued by transformation of *E. coli* as described above. In order to express the phytase in Aspergillus, the DNA was digested with appropriate restriction enzymes, size fractionated on gel, and a fragment corresponding to the phytase gene was purified. The gene was subsequently ligated to pHD414, digested with appropriate restriction enzymes, resulting in the plasmid pA2phy2.

After amplification of the DNA in *E. coli* the plasmid was transformed into *Aspergillus oryzae* as described above.

Test of *A. oryzae* Transformants

Each of the transformants were tested for enzyme activity as described above. Some of the transformants had phytase activity which was significantly larger than the *Aspergillus oryzae* background. This demonstrates efficient expression of the phytase in *Aspergillus oryzae*.

Example 2

Cloning and Expression of a Phytase From *Agrocybe pediades* CBS No. 900.96

Deposited Organisms

*Agrocybe pediades* CBS No. 900.96 comprises a phytase encoding DNA sequence of the invention.

*Escherichia coli* DSM NO 11313 contains the plasmid comprising the full length cDNA sequence, coding for a phytase of the invention, in the shuttle vector pYES 2.0.

Isolation of the DNA Sequence Shown in SEQ ID No. 21

The phytase encoding part of the DNA sequence shown in SEQ ID No. 21 coding for a phytase of the invention can be obtained from the deposited organism *Escherichia coli* DSM 11313 by extraction of plasmid DNA by methods known in the art (Sambrook et al. (1989) Molecular cloning: A laboratory manual, Cold Spring Harbor lab., Cold Spring Harbor, N.Y.).

Cloning and expression was done by using the Expression cloning in yeast technique as described in Example 1.

mRNA was isolated from *Agrocybe pediades*, CBS No. 900.96, grown as described above with agitation to ensure sufficient aeration.

Mycelia were harvested after 3–5 days' growth, immediately frozen in liquid nitrogen and stored at –80° C. A library from *Agrocybe pediades*, CBS No. 900.96, consisting of approx. $9 \times 10^5$ individual clones was constructed in *E. coli* as described with a vector background of 1%. Plasmid DNA from some of the pools was transformed into yeast, and 50–100 plates containing 250–400 yeast colonies were obtained from each pool.

Phytase-positive colonies were identified and isolated as described above. cDNA inserts were amplified directly from the yeast colonies and characterized as described in the Materials and Methods section above. The DNA sequence of the cDNA encoding the phytase is shown in SEQ ID No. 21 and the corresponding amino acid sequence is shown in SEQ ID No. 22. In SEQ ID No. 21 DNA nucleotides from No 1 to No. 1362 define the phytase encoding region.

The part of the DNA sequence in SEQ ID NO 21, which is encoding the mature part of the phytase is position 79 to 1362, which correspond to amino acid position 27–453 in SEQ ID NO 22.

The cDNA is obtainable from the plasmid in DSM 11313.

Total DNA was isolated from a yeast colony and plasmid DNA was rescued by transformation of *E. coli* as described above. In order to express the phytase in Aspergillus, the DNA was digested with appropriate restriction enzymes, size fractionated on gel, and a fragment corresponding to the phytase gene was purified. The gene was subsequently ligated to pHD414, digested with appropriate restriction enzymes, resulting in the plasmid pA3phy3.

After amplification of the DNA in *E. coli* the plasmid was transformed into *Aspergillus oryzae* as described in Example 1.

Test of *A. oryzae* Transformants

Each of the transformants were tested for enzyme activity as described in Example 1. Some of the transformants had phytase activity which was significantly larger than the *Aspergillus oryzae* background. This demonstrates efficient expression of the phytase in *Aspergillus oryzae*.

Example 3

Cloning and Expression of Phytases From *Paxillus involtus* CBS 100231 and *Trametes pubescens* CBS 100232

Deposited Organisms

*Paxillus involtus* CBS No. 100231 comprises two phytase encoding DNA sequences of the invention and *Trametes pubescens* CBS 100232 comprises a phytase of the invention.

*Escherichia coli* DSM Nos. 11842, 11843 and 11844 contain the plasmids comprising the full length cDNA sequences, coding for these phytases of the invention, in the shuttle vector pYES 2.0, viz. PhyA1, PhyA2 of *Paxillus involtus* and the phytase of *Trametes pubescens*, respectively.

Isolation of the DNA Sequences Shown in SEQ ID Nos. 25, 27 and 29

The phytase encoding part of the DNA sequences shown in SEQ ID Nos. 25, 27 and 29 coding for phytases of the invention can be obtained from the deposited organisms *Escherichia coli* DSM 11842, 11843 and 11844, respectively, by extraction of plasmid DNA by methods known in the art (Sambrook et al. (1989) Molecular cloning: A laboratory manual, Cold Spring Harbor lab., Cold Spring Harbor, N.Y.).

Cloning and expression was done by using the Expression cloning in yeast technique as described in Example 1.

mRNA was isolated from the respective microorganisms, grown under phytase producing conditions, e.g. as described above with agitation to ensure sufficient aeration.

Mycelia were harvested after 3–5 days' growth, immediately frozen in liquid nitrogen and stored at −80° C. Libraries, consisting of approx. 9×10$^5$ individual clones was constructed in *E. coli* as described with a vector background of 1%. Plasmid DNA from some of the pools was transformed into yeast, and 50–100 plates containing 250–400 yeast colonies were obtained from each pool.

Phytase-positive colonies were identified and isolated as described above. cDNA inserts were amplified directly from the yeast colonies and characterized as described in the Materials and Methods section above. The DNA sequences of the cDNA encoding the phytases are shown in SEQ ID Nos. 25, 27 and 29 and the corresponding amino acid sequences are shown in SEQ ID Nos. 26, 28 and 30, respectively.

The cDNA is obtainable from the plasmids in DSM 11842, 11843 and 11844.

Total DNA was isolated from a yeast colony and plasmid DNA was rescued by transformation of *E. coli* as described above. In order to express the phytases in Aspergillus, the DNA was digested with appropriate restriction enzymes, size fractionated on gel, and a fragment corresponding to the phytase gene was purified. The gene was subsequently ligated to pHD414, digested with appropriate restriction enzymes.

After amplification of the DNA in *E. coli* the plasmid was transformed into Aspergillus oryzae as described in Example 1.

Test of *A. oryzae* Transformants

Each of the transformants were tested for enzyme activity as described in Example 1. Some of the transformants had phytase activity which was significantly larger than the *Aspergillus oryzae* background. This demonstrates efficient expression of the phytases in *Aspergillus oryzae*.

The two phytases of *Paxillus involtus* CBS 100231 (PhyA1P.i. and PhyA2P.i.) and the phytase of *Trametes pubescens* CBS 100232 (PhyAT.p.) have the following characteristics:

| | Number of amino acids | Calculated molecular weight (MW) | Isoelectric point (pI) |
| --- | --- | --- | --- |
| PhyA1 *P. i.* | 423 | 46 K | 6.4 |
| PhyA2 *P. i.* | 423 | 45 K | 4.5 |
| PhyA *T. p.* | 426 | 46 K | 4.3 |

Example 4

Expression Cloning and Characterization of Five Phytase (phyA) cDNAs From Four Basidiomycetes *Agrocybe pediades, Peniophora lycii, Paxillus involtus* and *Trametes pubescens*

Directional cDNA libraries are constructed as described in the previous examples from phytase induced mycelia from the four basidiomycetes *A. pediades, P. lycii, P. involtus* and *T. pubescens*, in the yeast expression vector pYES2.0.

The cDNA libraries are screened for phytase activity, resulting in isolation of five different phytase cDNAs, phyA *P. lycii*, phyA *A. pediades*, phyA1 *P. involtus*, phyA2 *P. involtus*, and phyA *T. pubescens*.

Characterization of the phyA cDNA from these clones reveals conserved regions apparently specific to the basidiomycete phytases. This indicates that the basidiomycete phytases belong to their own subfamily within the group of fungal phytases.

The five new phytases are transformed and overexpressed in *A. oryzae* in order to facilitate the purification and characterization of the recombinant enzymes.

Isolation of phyA cDNAs by Expression Cloning in Yeast

The fungal strains *A. pediades, P. lycii, P. involtus* and *T. pubescens* are cultivated stationary on FG-4 medium (30 g/l soy meal, 15 g/l malto dextrine, 5 g/l bacto peptone, 0.2 g/l pluronic).

The accumulation of total phytase activity in the culture supernatants is monitored on a plate assay as described in the section "Test of *A. oryzae* transformants" of Example 1.

Highest levels of phytase activity are detected after five to fifteen days of growth, and therefore poly(A)+RNAs isolated from mycelia harvested according to this, are used to construct four cDNA libraries in the yeast expression vector pYES2.0. Aliquots of the libraries are transformed into *S. cerevisiae* W3124 and the transformants are plated on SC agar containing 2% glucose and incubated at 30° C.

Isolation of poly(A)+RNA and construction of cDNA libraries is performed as described in Example 1 (the section "Fermentation procedure of *Peniophora lycii* CBS no. 686.96 for mRNA isolation" to the section "Transformation of *Aspergillus oryzae* or *Aspergillus niger*."

Identification of Positive Colonies

Positive colonies are identified as described in Example 1 under the same heading.

Between 20000 and 30000 yeast clones from each library are screened for phytase activity and one to four phytase positive yeast clones are found in each library. The positive colonies correspond to five different phytase genes, phyA *P. lycii* (pC1phy2), phyA *A. pediades* (pC1phy3), phyA1 *P. involtus* (pC1phy5), phyA2 *P. involtus* (pC1phy7), and phyA *T. pubescens* (pC1phy6).

Characterization of the phyA cDNAs

Figure 1:
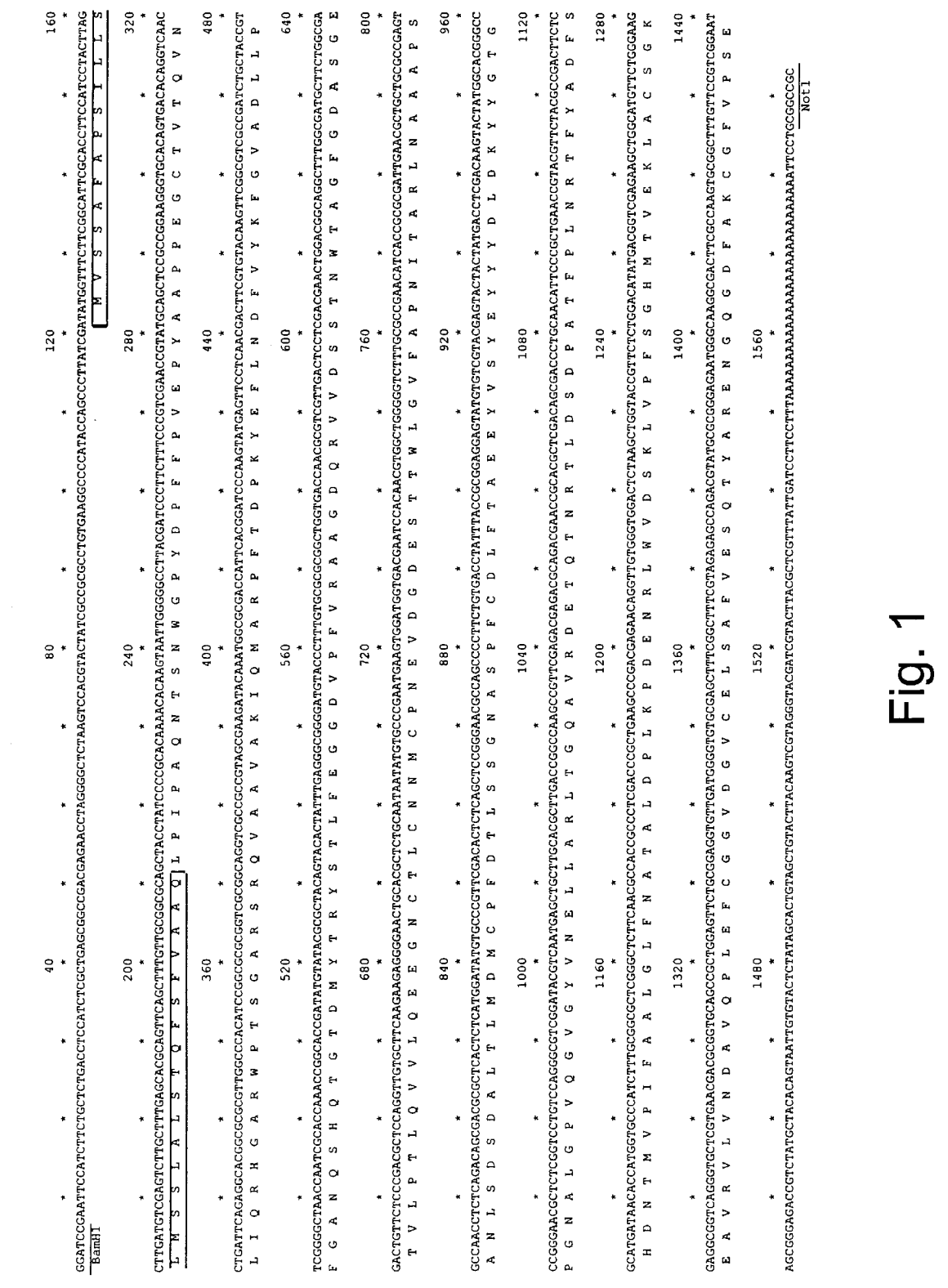

The primary structure of the phyA cDNA encoding PhyA of *Peniophora lycii* is shown in FIG. 1. The 1593 bp cDNA from pC1phy2 contains a 1320 bp open reading frame (ORF), coding for a 439 residue polypeptide with a calculated molecular weight of 47560. The phyA cDNA encodes an 30 amino acid signal peptide. The mature protein has a calculated molecular weight of 44473 and an isoelectric point of pI 4.15. The cDNA and amino acid sequences are included in the sequence listing, (SEQ ID NO: 23) and (SEQ ID NO: 24), respectively.

Figure 2:
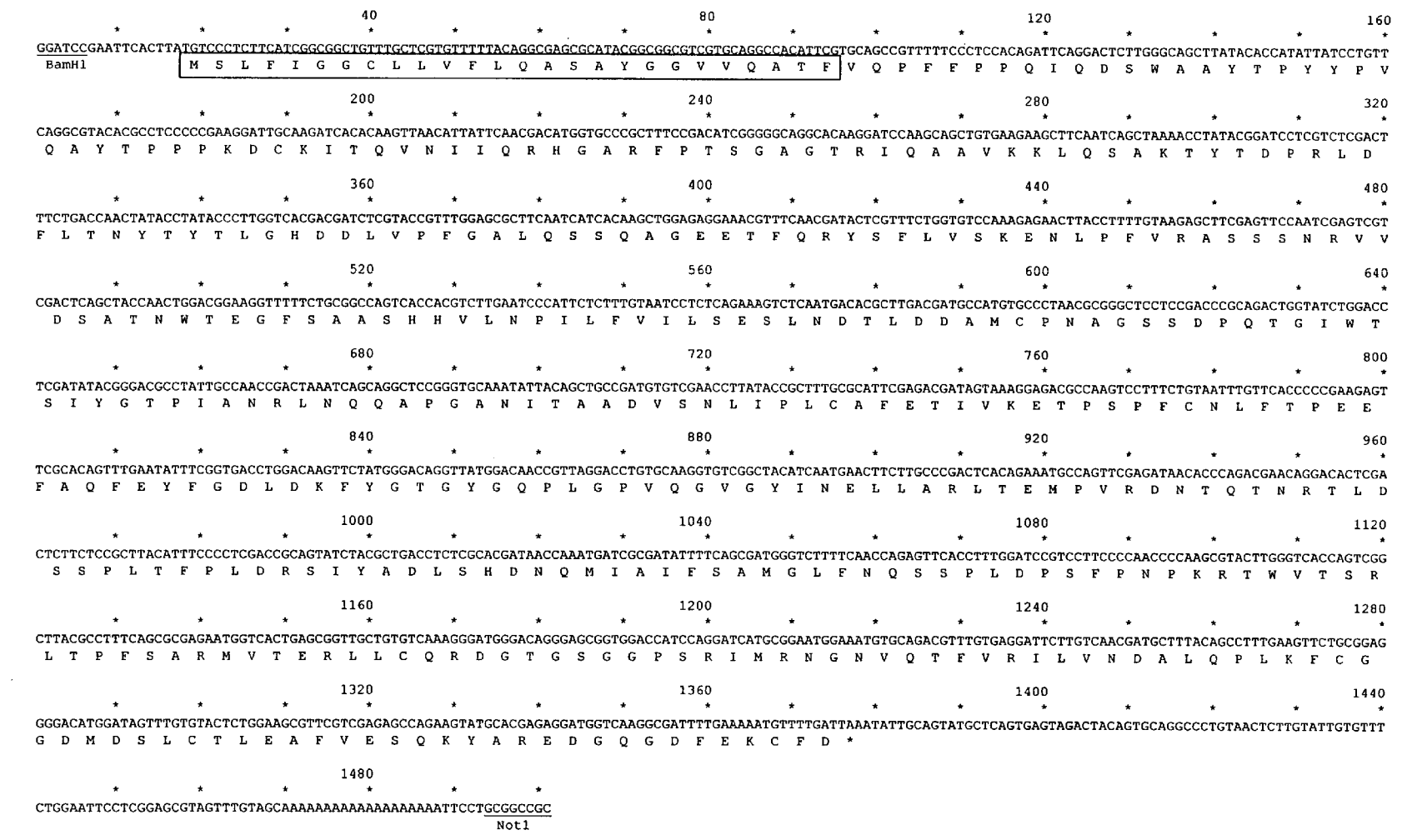

The phyA cDNA sequence and the deduced sequence of PHYA from *A. pediades* are presented in FIG. 2. The 1501 bp cDNA from pC1phy3 contains a 1362 ORF coding for a 453 residue polypeptide with a 31 amino acid long signal peptide. The 422 amino acid mature protein has a calculated molecular weight of 46781 and an isoelectric point of pI 4.82. The cDNA and amino acid sequences are included in the sequence listing as (SEQ ID NO: 21) and (SEQ ID NO: 22), respectively.

Figure 3:
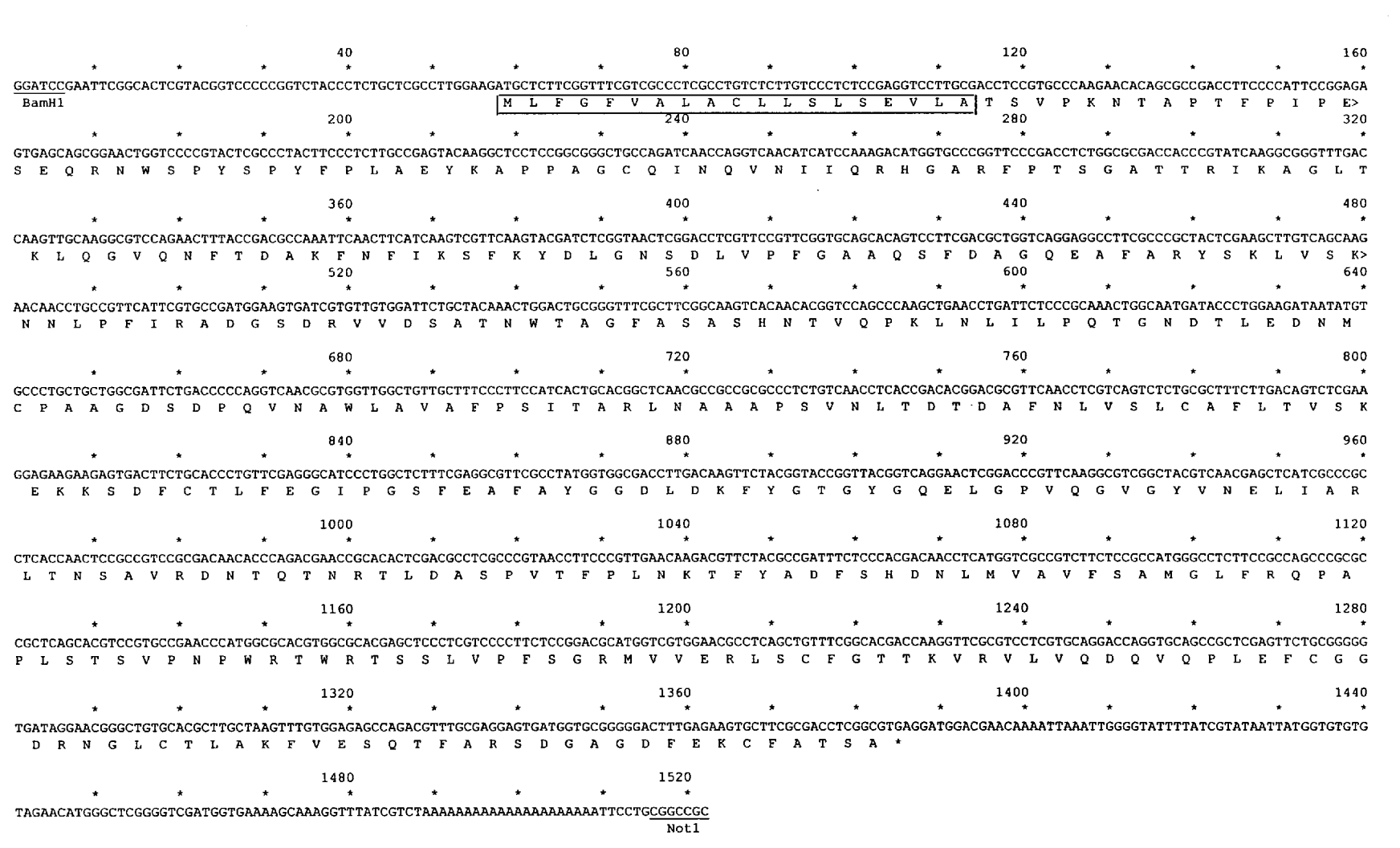
Figure 4:
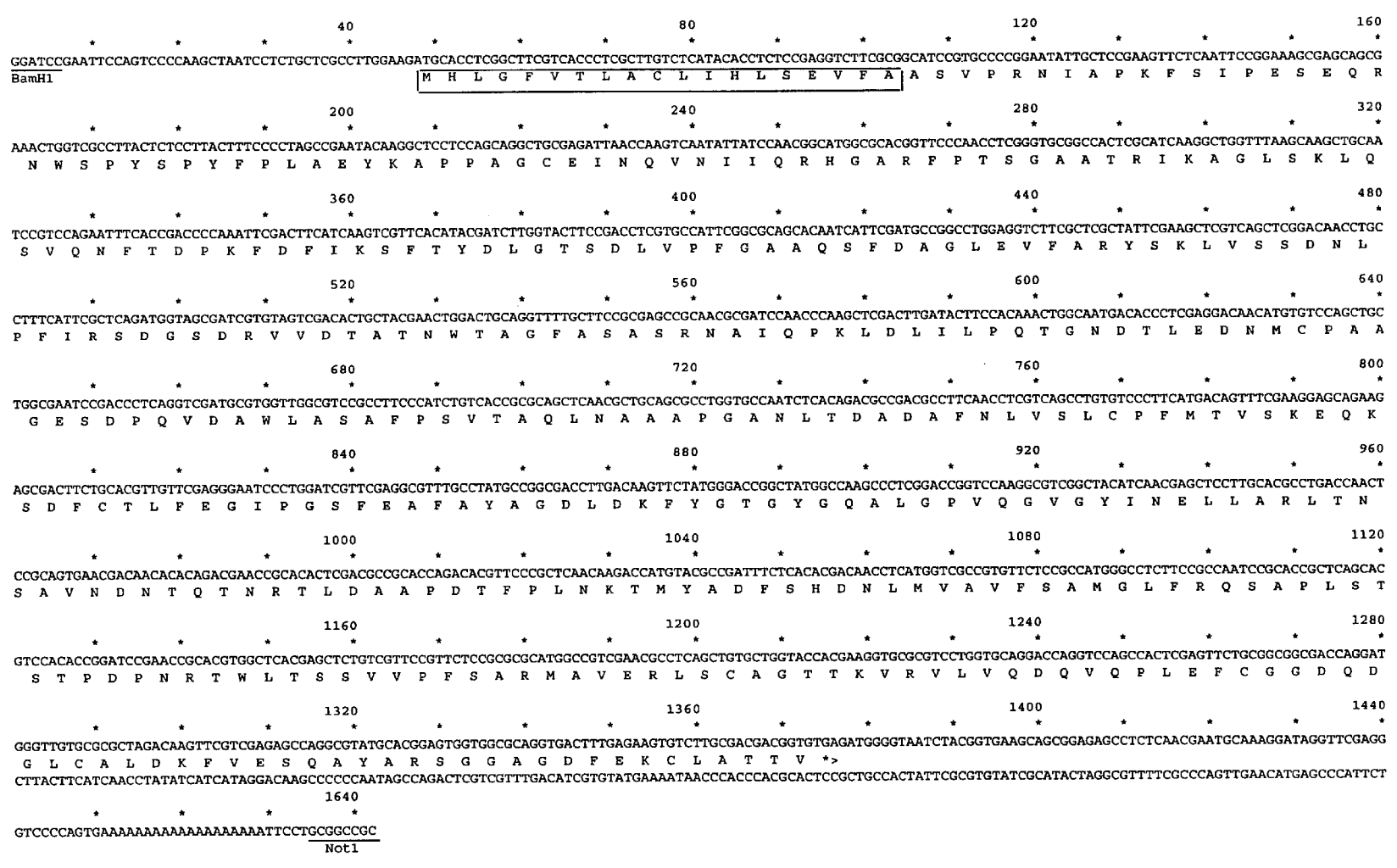

The nucleotide sequences of the phyA1 and the phyA2 cDNA cloned from *Paxilus involtus*, and the deduced sequences of PHY1 and PHY2, are shown in FIG. 3. and FIG. 4. respectively.

The 1522 bp insert in pC1phy5 (phyA1) contains a 1329 bp ORF coding for a 442 amino acid polypeptide. According to the SignalP V1.1 prediction (Henrik Nielsen, Jacob Engelbrecht, Stren Brunak and Gunnar von Heijne: "Identification of prokaryotic and eukaryotic signal peptides and prediction of their cleavage sites," Protein Engineering 10, 1–6 (1997)), the signal peptide consists of 19 amino acids. The mature protein therefore has a predicted molecular weight of 45932 and a pI of 6.39. The cDNA and amino acid sequences are included in the sequence listing as (SEQ ID NO: 25) and (SEQ ID NO: 26), respectively.

The plasmid pC1phy7 (phyA2) contains a 1642 bp insert with a 1329 bp ORF coding for a 442 residue polypeptide. The SignalP V1.1 program referred to above predicts a putative signal peptidase cleavage site between Ala-19 and Ala-20 in the phyA2 encoded preprotein and thus the predicted molecular weight of the mature protein is 45466 and the predicted isoelectric point is 4.50. The cDNA and amino acid sequences are included in the sequence listing as (SEQ ID NO: 27) and (SEQ ID NO: 28), respectively.

Figure 5:
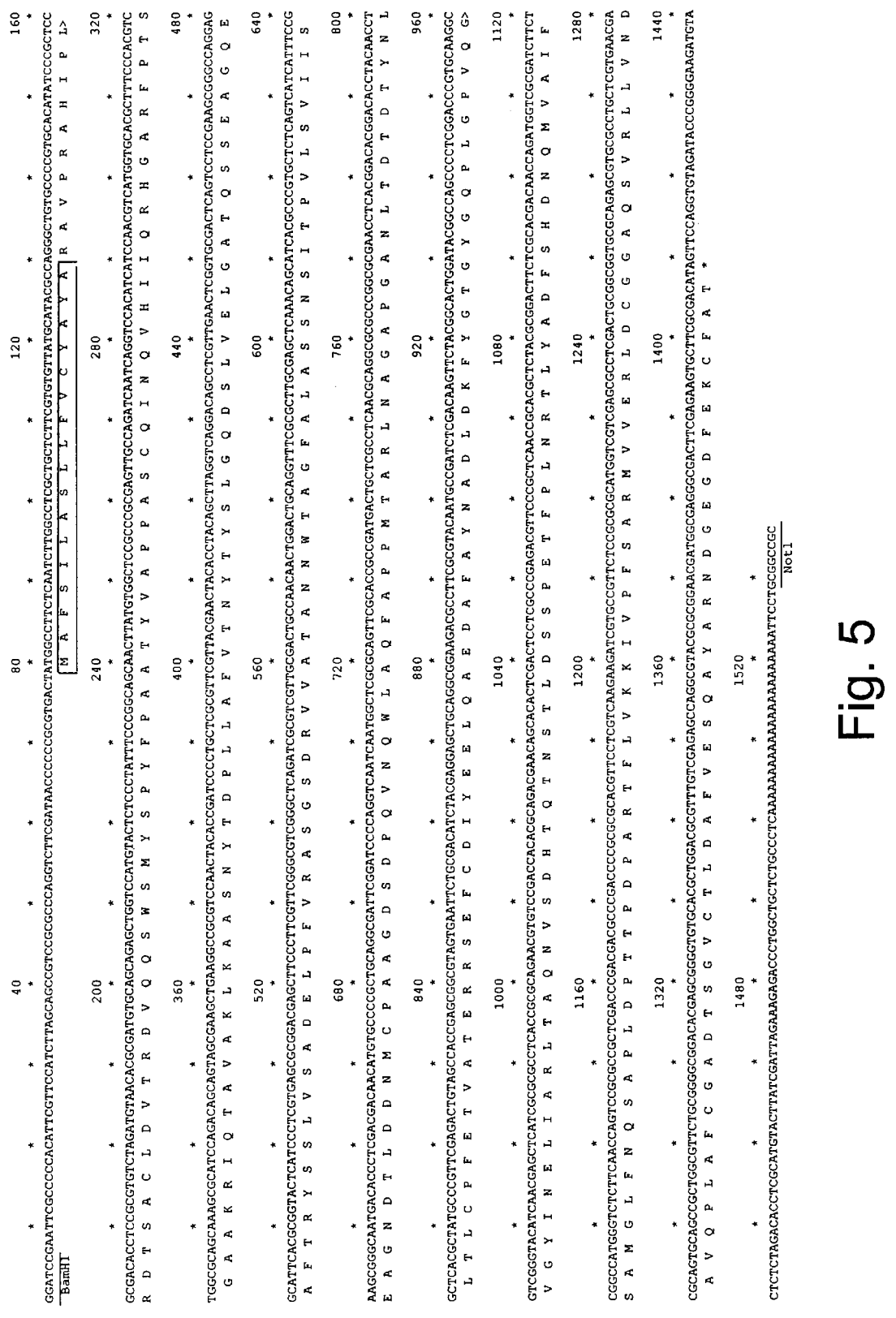

In FIG. 5. the phyA cDNA sequence and the deduced sequence of PHYA from *T. pubescens* are shown. The 1536 bp insert in pC1phy6 contains a 1332 bp ORF coding for a 443 residue polypeptide. According to the SignalP V1.1 prediction referred to above, the signal peptide consists of 17 residues. The mature protein therefore consists of 426 amino acids and has a predicted molecular weight of 45905 and a pI of 4.34. The cDNA and amino acid sequences are included in the sequence listing as (SEQ ID NO: 29) and (SEQ ID NO: 30), respectively.

Conserved Basidiomycete Phytase Regions

The overall identities between known phytases of the phyllum Ascomycota and phytases of the invention of the phyllum Basidiomycota and are shown in table 1 below ("X/Y" meaning "DNA/peptide" identity as determined by GAP GCGv8).

In this table, the first five phytases in the leftmost column are basidiomycete phytases, whereas the rest are ascomycete phytases.

TABLE 1

Homology of ascomycete and basidiomycete phytases (complete cDNA compared)

| | phyA1 P. involtus | phyA2 P. involtus | phyA T. pubescens | phyA A. pediades | phyA P. lycii | phyA A. fumigatus | phyA A. niger | phyA A. terreus | phyA T. lanuginosa | pyhA M. thermophila | phyA T. thermophilus | phyA E. nidulans |
|---|---|---|---|---|---|---|---|---|---|---|---|---|
| phyA1 P. involtus | | 81/85 | 66/62 | 58/58 | 56/56 | 50/40 | 51/40 | 52/41 | 49/40 | 54/41 | 48/37 | 49/40 |
| phyA2 P. involtus | 81/85 | | 66/63 | 59/58 | 57/53 | 49/39 | 50/38 | 51/39 | 48/39 | 54/40 | 50/36 | 49/39 |
| phyA T. pubescens | 66/62 | 66/63 | | 60/61 | 58/51 | 51/40 | 50/41 | 53/39 | 49/40 | 53/41 | 50/39 | 50/39 |
| phyA A. pediades | 58/58 | 59/58 | 60/61 | | 56/52 | 48/37 | 49/38 | 48/38 | 47/37 | 50/39 | 48/37 | 50/42 |
| phyA P. lycii | 56/56 | 57/53 | 58/51 | 56/52 | | 50/41 | 51/42 | 53/41 | 50/39 | 54/45 | 50/43 | 50/40 |
| phyA A. fumigatus | 50/40 | 49/39 | 51/40 | 48/37 | 50/41 | | 65/65 | 64/59 | 59/51 | 58/51 | 62/61 | 65/67 |
| phyA A. niger | 51/40 | 50/38 | 50/41 | 49/38 | 51/42 | 65/65 | | 64/61 | 58/52 | 58/48 | 61/61 | 64/63 |
| phyA A. terreus | 52/41 | 51/39 | 53/39 | 48/38 | 53/41 | 64/59 | 64/61 | | 56/49 | 62/47 | 62/57 | 63/57 |
| phyA T. lanuginosa | 49/40 | 48/39 | 49/40 | 47/37 | 50/39 | 59/52 | 58/53 | 56/49 | | 55/46 | 62/59 | 59/54 |
| phyA M. thermophila | 54/41 | 54/40 | 53/41 | 50/39 | 54/45 | 58/51 | 58/48 | 62/47 | 55/46 | | 57/48 | 57/51 |
| PhyA T. thermophilu | 48/37 | 50/36 | 50/39 | 48/37 | 50/43 | 62/61 | 61/61 | 62/57 | 62/59 | 57/48 | | 60/59 |
| phyA E. nidulans | 49/40 | 49/39 | 50/39 | 50/42 | 50/40 | 65/67 | 64/63 | 63/57 | 59/54 | 57/51 | 60/59 | |

In this experiment, the complete cDNA sequences were compared. According to table 1, the DNA-homology for phytases within the basidiomycetes group is in the range of from 81% to 56% identity, and within the ascomycetes group in the range of from about 65% to 55% identity. Accordingly, the internal group homology seems higher within the group of basidiomycetes phytases as compared to ascomycetes phytases.

The DNA homology of the basidiomycet phytases versus the ascomycet phytases, however, is only in the range of from about 54% to 48%. Accordingly, these two groups as such are more different from each other than the difference observed within each group (and this points towards the discrimination between ascomycete phytases and basidiomycete phytases being legitimate.

This relationship is also visualized in the alignments in FIG. 6. and FIG. 7.

For some of the phytases of Table 1, Table 2 below shows the results when comparing cDNA sequences of ORF and peptide sequences of the mature protein (signal peptide cleaved off).

In this table, peptide homologies are indicated in the upper right half of the table, whereas DNA homologies are indicated in the lower left half (both % identity according to GAP GCGv8).

From the alignments at FIGS. 6 and 7 it is apparent that several sequence motifs are conserved within the five basidiomycete phytases. Based on this alignment several conserved partial sequences have been derived (SEQ ID Nos: 1–14). Still further, some regions of deletions, which are also conserved in the basidiomycete phytases, have also been derived (see e.g claim 5).

Some examples of particularly highly conserved sequences are the so-called Consensus Sequences I, II and III below, the corresponding alignments of which are shown in Tables 3 and 4 below. In these tables, identical residues in at least nine of the sequences are indicated by a grey box and identical residues for the phytases from basidiomycetes are indicated by a white box.

Consensus Sequence I: I-Q-R-H-G-A-R-[F/W]-P-T-S-G-A-X-X-R
(SEQ ID NO: 3)
Consensus Sequence II: N-W-T-[A/E]-G-F-X-X-A-S
(SEQ ID NO: 5)
Consensus Sequence III:
F-V-E-S-Q-X- [Y/F]-A-R-X-X-G-X-G-D-F-[E/A]-K-C
(SEQ ID NO: 9)

TABLE 2

Homology of selected ascomycete and basidiomycete phytases
(ORF cDNA and mature polypeptide compared)

| | | | | | | % ID pep. | | | | |
|---|---|---|---|---|---|---|---|---|---|---|
| % ID DNA seq. | phyA1 P. involtus | phyA2 P. involtus | phyA T. pubescens | phyA A. pediades | phyA P. lycii | phyA A. fumigatus | phyA A. niger | phyA A. terreus | phyA T. lanuginosa | phyA M. thermophila |
| phyA1 P. involtus | | | | | | 40 | 41 | 41 | 40 | 41 |
| phyA2 P. involtus | | | | | | 39 | 39 | 39 | 40 | 41 |
| phyA T. pubescens | | | | | | 41 | 42 | 39 | 40 | 42 |
| phyA A. pediades | | | | | | 39 | 39 | 41 | 37 | 40 |
| phyA P. lycii | | | | | | 42 | 42 | 43 | 41 | 46 |
| phyA A. fumigatus | 50 | 49 | 51 | 48 | 50 | | | | | |
| phyA A. niger | 51 | 50 | 50 | 49 | 51 | | | | | |
| phyA A. terreus | 52 | 51 | 53 | 48 | 53 | | | | | |
| phyA T. lanuginosa | 49 | 48 | 49 | 47 | 50 | | | | | |
| phyA M. thermophila | 54 | 54 | 53 | 50 | 54 | | | | | |

TABLE 3

Partial alignments corresponding to consensus sequences I and II

| | AA pos. 68–83 in P. lycii | AA pos. 162–171 in P. lycii |
|---|---|---|
| phyA1 P. involtus | I Q ▓▓▓▓▓ F ▓▓ S G A T T R | N W T A ▓▓▓ A S ▓ - - - - - - - S |
| phyA2 P. involtus | I Q ▓▓▓▓▓ F ▓▓ S G A A T R | N W T A ▓▓▓ A S ▓ - - - - - - - S |
| phyA T. pubescens | I Q ▓▓▓▓▓ F ▓▓ S G A A K R | N W T A ▓▓▓ A L ▓ - - - - - - - S |
| phyA A. pediades | I Q ▓▓▓▓▓ F ▓▓ S G A G T R | N W T E ▓▓▓ S A ▓ - - - - - - - S |
| phyA P. lycii | I Q ▓▓▓▓▓ W ▓▓ S G A R S R | N W T A ▓▓▓ G D ▓ - - - - - - - S |
| phyA A. fumigatus | L S ▓▓▓▓▓ Y ▓▓ S S K S K K | K F I E ▓▓▓ Q Q ▓ K L A D P G A - |
| phyA A. niger | L S ▓▓▓▓▓ Y ▓▓ D S K G K K | K F I E ▓▓▓ Q S T K L K D P R A Q |
| phyA A. terreus | L A ▓▓▓▓▓ S ▓▓ H S K T K A | K F V E ▓▓▓ Q T ▓ R Q D D H H A N |
| phyA T. lanuginosa | L S ▓▓▓▓▓ Y ▓▓ A H K S E V | F F N R ▓▓▓ Q D ▓ K D R D P R S N |
| phyA M. thermophila | L S ▓▓▓▓▓ A ▓▓ L K R A A S | N F T Q ▓▓▓ H S ▓ L L A D R G S T |

TABLE 4

Partial alignments corresponding to consensus sequence III

| | AA pos. 415–433 in P. lycii |
|---|---|
| phyA1 P. involtus | ▓▓ E S Q T F ▓▓ S D G A ▓ D F E K ▓ |
| phyA2 P. involtus | ▓▓ E S Q A Y ▓▓ S G G A ▓ D F E K ▓ |
| phyA T. pubescens | ▓▓ E S Q A Y ▓▓ N D G E ▓ D F E K ▓ |
| phyA A. pediades | ▓▓ E S Q K Y ▓▓ E D G Q ▓ D F E K ▓ |
| phyA P. lycii | ▓▓ E S Q T Y ▓▓ E N G Q ▓ D F A K ▓ |
| phyA A. fumigatus | ▓▓ K G L S W ▓▓ S G - - ▓ N W G E ▓ |
| phyA A. niger | ▓▓ R G L S F ▓▓ S G - - ▓ D W A E ▓ |
| phyA A. terreus | ▓▓ A G L S F ▓ Q A G - - ▓ N W A D ▓ |
| phyA T. lanuginosa | W I K G L T F ▓▓ Q G - - ▓ H W D R ▓ |
| phyA M. thermophila | ▓ I E S M A F ▓▓ N N - - ▓ K W D L ▓ |

Table 5 below also shows some of the consensus sequences, viz. (SEQ ID NO: 2), (SEQ ID NO: 5) and (SEQ ID NO: 9), respectively, in an alignment as in FIG. 7.

TABLE 5

Basidiomycete phytase consensus sequences in alignment

| AA pos. P. lycii | 64 | | 70 | | 75 | | 80 |
|---|---|---|---|---|---|---|---|
| phyA1 P. involtus | | N I | ▓R H G A R▓ | F ▓▓ | | | |
| phyA2 P. involtus | | N I | ▓R H G A R▓ | F ▓▓ | | | |
| phyA T. pubescens | | H I | ▓R H G A R▓ | F ▓▓ | | | |
| phyA A. pediades | | N I | ▓R H G A R▓ | F ▓▓ | | | |
| phyA P. lycii | | N L | ▓R H G A R▓ | W ▓▓ | | | |
| phyA A. fumigatus | L V | Q V L | S▓R H G A R▓ | Y ▓▓ | S S K | | |
| phyA A. niger | F A | Q V L | S▓R H G A R▓ | Y ▓▓ | D S K | | |
| phyA A. terreus | F V | Q V L | A▓R H G A R▓ | S ▓▓ | H S K | | |
| phyA T. lanuginosa | F V | Q V L | S▓R H G A R▓ | Y ▓▓ | A H K | | |
| phyA M. thermophila | F A | Q V G | S▓R H G A R▓ | A ▓▓ | L K R | | |

TABLE 5-continued

Basidiomycete phytase consensus sequences in alignment

| AA pos. P. lycii | 162 | | 170 | | 171 |
|---|---|---|---|---|---|
| phyA1 P. involtus | | A ▓▓ | A S ▓ | - - - - - - | |
| phyA2 P. involtus | | A ▓▓ | A S ▓ | - - - - - - | |
| phyA T. pubescens | | A ▓▓ | A L ▓ | - - - - - - | |
| phyA A. pediades | | E ▓▓ | S A ▓ | - - - - - - | |
| phyA P. lycii | | A ▓▓ | G D ▓ | - - - - - - | |
| phyA A. fumigatus | K F I E | ▓▓ Q Q | ▓ K L A | D P G A - | |
| phyA A. niger | K F I E | ▓▓ Q S T K L K | D P R A Q | | |
| phyA A. terreus | K F V E | ▓▓ Q T | ▓ R Q D | D H H A N | |
| phyA T. lanuginosa | F F N R | ▓▓ Q D | ▓ K D R | D P R S N | |
| phyA M. thermophila | N F T Q | ▓▓ H S | ▓ L L A | D R G S T | |

| AA pos. P. lycii | 415 | | 423 | | 431 |
|---|---|---|---|---|---|
| phyA1 P. involtus | ▓▓ | T F ▓▓ S D | A ▓▓ | | E ▓ |
| phyA2 P. involtus | ▓▓ | A Y ▓▓ S G | A ▓▓ | | E ▓ |
| phyA T. pubescens | ▓▓ | A Y ▓▓ N D | E ▓▓ | | E ▓ |
| phyA A. pediades | ▓▓ | K Y ▓▓ E D | Q ▓▓ | | E ▓ |
| phyA P. lycii | ▓▓ | T Y ▓▓ E N | Q ▓▓ | | A ▓ |
| phyA A. fumigatus | ▓▓ K G L S W | ▓▓ S G - - | ▓▓ N W G E | | ▓ |
| phyA A. niger | ▓▓ R G L S F | ▓▓ S G - - | ▓▓ D W A E | | ▓ |
| phyA A. terreus | ▓▓ A G L S F | ▓ Q A G - - | ▓▓ N W A D | | ▓ |
| phyA T. lanuginosa | W I K G L T F | ▓ Q G - - | ▓▓ H W D R | | ▓ |
| phyA M. thermophila | ▓ I E S M A F | ▓▓ N N - - | ▓▓ K W D L | | ▓ |

Consensus Sequence I (SEQ ID NO: 3), residue position 68 to 83 with the numbering for PHYA *P. lycii* in FIG. 7., is around the active site, and all five basidiomycetes phytases have this consensus sequence I-Q-R-H-G-A-R-[F/W]-P-T-S-G-A-X-X-R with thirteen conserved residues. Still further, four of the five phytases have a fourteenth common residue F75. This is in contrast to the ascomycetes phytases which only have eight conserved residues in the same region (Table 3).

When Consensus Sequence II (SEQ ID NO: 5), AA position 162–171 in *P. lycii,* is compared to the ascomycete phytases it can be seen that the basidiomycete phytases lack six to seven residues between *P. lycii* F167 (*A. niger* F177) to *P. lycii* P177 (*A. niger* P194) (See FIG. 7) and that the basidiomycetes phytases overall have a much larger degree of conservation with seven identical residues out of ten (Table 3). The ascomycetes phytases have only three conserved residues out of seventeen in the same region.

Consensus Sequence III (SEQ ID NO: 9), AA pos. 415–433 in *P. lycii,* consists of nineteen residues with thirteen residues conserved in the basidiomycetes phytases. There are three residues in the consensus sequence that are conserved through all the fungal phytases. In the *P. lycii* sequence the residues are A422, G428, and C433 and for *A. niger* they are A454, G458, and C463. All the basidiomycete phytases have five residues between the conserved alanine and glycine while all the ascomycete phytases only have three (Table 4).

Expression of PHYA in *Aspergillus oryzae*

In order to obtain high level expression of the PHYA phytases in *Aspergillus oryzae* for further purification and characterization of the protein, the five phyA cDNAs from *A. pediades, P. lycii, P. involtus,* and *T. pubescens* were subcloned into pHD414, a fungal expression vector. The phyA cDNA is here inserted 3' to the TAKA-amylase promoter sequence and 5' to the polyA and terminator sequence from the *A. niger* glucoamylase gene. The pHD414 phyA constructs were transformed into *A. oryzae* by co-transformation with the amdS selection plasmid (see the section "Transformation of *Aspergillus oryzae* or *Aspergillus niger*" in Example 1). The transformants were screened for phytase activity in the supernatants, and the highest yielding transformants were selected for fermentation.

Conclusion

The high degree of conserved regions within this group of basidiomycete phytases indicate that they belong to their own subfamily within the group of fungal phytases.

Based on these regions PCR-primers specific for molecular screening of related phytases can be designed (Example 5).

Example 5

Molecular Screening (Primerset 522/538)

The following degenerate oligonucleotide primers coding for highly conserved regions within the five basidiomycete phytases have been designed for molecular screening:

522 sense primer:

5' - CCC AAG CTT AAY TGG ACN GMN GGN TT - 3'
(SEQ ID NO: 15)

corresponds to amino acids N-W-T-[A,E,D]-G-[F,L] with a CCC and HindIII site 5' tail;

537 sense primer:

5' - CCC AAG CTT GAY AAR TWY GGN AC - 3'
(SEQ ID NO: 16)

corresponds to amino acids D-K-[F,Y]-Y-G-T with a CCC and HindIII site 5' tail;

538 anti-sense primer:

5' - GCT CTA GAC RTA RWA YTT RTC NAR RTC - 3'
(SEQ ID NO: 17)

corresponds to amino acids D-[F,L]-D-K-[F,Y]-Y-G with a GC and XbaI site 5' tail;

525 anti-sense primer:

5' - GCT CTA GAC AYT TNK CRA ART CNC C - 3'
(SEQ ID NO: 18)

corresponds to amino acids G-D-F-[A,D,E]-K with a GC and XbaI site 5' tail;

539 sense primer:

5' - CCC AAG CTT CAR GTN MAY MTN ATH CA - 3'
(SEQ ID NO: 19)

corresponds to amino acids Q-V-[N,H]-[I,L,M]-I-[Q,H] with a CCC and HindIII site 5' tail (SEQ ID NO: 15);

540 anti-sense primer:

5' - GCT CTA GAC RAA NCC NKC NGT CCA RTT - 3'
(SEQ ID NO: 20)

corresponds to amino acids N-W-T-[A,D,E]-G-F with a GC and XbaI site 5' tail;
wherein N=A, C, G or T; R=A or G; Y=C or T; M=A or C; W=A or T.

The design of the primers is based on the alignment in FIG. 7.

For a general reference to the PCR reaction, reference can be had to e.g. Sambrook et al, Molecular Cloning, a Laboratory Manual, $2^{nd}$ edition; or Lubert Stryer: Biochemistry, $4^{th}$ edition, Freeman and Company, New York, 1995, e.g. pp. 132–134.

First, the 522/538 primerset is tested on genomic DNA from selected ascomycetes and basidiomycetes shown in Table 6 below.

The genomic DNA is isolated according to the following procedure:

Procedure for Isolation of Fungal Genomic DNA
1. Grind mycelia in liquid N2 in a morter
2. Transfer mycelia to an 2.0 ml Eppendorf tube up to the 0.5 ml mark
3. Add 1.0 ml lysis buffer and mix
4. Add 10 μl 4 mg/ml DNase free RNase A (New England Biolabs)
5. Incubate for 30 min. at 37° C.
6. Add 40 μl 16 mg/ml Protease K (New England Biolabs)
7. Incubate for 1 h. at 50° C. with gently shaking
8. Centrifuge for 15 minutes full speed in a microcentrifuge
9. Apply supernatant to a QIAprep-spin column. Spin for 1 min. and discard filtrate
10. Wash with 0.5 ml buffer PB, spin for 1 min. and discard filtrate
11. Wash with 0.75 ml buffer PE, spin for 1 min. and discard filtrate
12. Drain any existing PE buffer with a quick spin and let dry completely
13. Place spin column in a clean microfuge tube and elute by adding 125 μl H2O. Let sit for 5 min. and then spin for 3 min Lysis buffer:
100 mM EDTA
10 mM Tris pH. 8
1% Triton X-100

200 mM NaCl 500 mM Guanidine-HCl

For further information on QIAprep spin column, PB buffer and PE buffer please refer to the QIAprep™ Plasmid Handbook from QIAGEN GmbH.

Experimental Procedure

Approximately 100 to 200 ng genomic DNA or 10–20 ng doublestranded cDNA is used as template for PCR amplification in PCR buffer (10 mM Tris-HCl, pH 8.3, 50 mM KCl) containing 200 μM of each dNTP, 3.5 mM MgCl2, 2.5 Units AmpliTaq Gold™, and 100 pmol of each of the degenerate primers 522 and 538. The total volume is 50 μl. The PCR reaction is carried out in a Perkin-Elmer GeneAmp PCR System 2400. The PCR reaction is performed using a cycle profile of:

```
94° C. - 10 min; 1 cycle
94° C. - 1 min, 60° C. - 1 min, 72° C. - 30 sec; 2 cycles
94° C. - 1 min, 59° C. - 1 min, 72° C. - 30 sec; 2 cycles
94° C. - 1 min, 58° C. - 1 min, 72° C. - 30 sec; 2 cycles
    .
    .
    .
94° C. - 1 min, 52° C. - 1 min, 72° C. - 30 sec; 2 cycles
94° C. - 1 min, 50° C. - 1 min, 72° C. - 30 sec; 14 cycles
72° C. - 7 min; 1 cycles
```

5 μl aliquots of the amplification products are analyzed by electrophoresis in 1.5% agarose gels.

Table 6 below shows the results of the test of this primerset, viz. whether a specific PCR band was detected or not.

TABLE 6

Test of primerset 522/538 on genomic DNA from asco- and basidiomycetes

| Microorganism | Phyllum | Strain collection number | PCR band detected |
| --- | --- | --- | --- |
| Cladorinum sp. | Ascomycota | CBS 427.97 | No |
| Cytospora sp. | Ascomycota | CBS 424.97 | No |
| Cytospora sp. | Ascomycota | CBS 425.97 | No |
| Gelasinospora sp. | Ascomycota | NN 040455 | No |
| Agrocybe pediades | Basidiomycota | CBS 900.96 | Yes |
| Amylostereum Chailletii | Basidiomycota | NN strain collection | Yes |
| Bjerkandera adusta | Basidiomycota | CBS 580.95 | Yes |
| Bjerkandera sp. | Basidiomycota | NN strain collection | Yes |
| Bolbitius aleuritus | Basidiomycota | do | Yes |
| Cerrena unicolor | Basidiomycota | do | Yes |
| Coniophora arida | Basidiomycota | do | Yes |
| Conocybe sp. | Basidiomycota | do | Yes |
| Coprinus cinereus | Basidiomycota | IFO 30116 | Yes |
| Cystoderma carcharias | Basidiomycota | NN strain collection | Yes |
| Daedalea quercina | Basidiomycota | NN005877 | Yes |
| Exidia glandulosa | Basidiomycota | CBS 277.96 | Yes |
| Femsjonia sp. | Basidiomycota | NN strain collection | Yes |
| Fomes fomentarius | Basidiomycota | CBS 276.96 | Yes |
| Hygrophoropsis pallida | Basidiomycota | NN strain collection | Yes |
| Hyphoderma argillaceum | Basidiomycota | do | Yes |
| Hyphodontia pallidula | Basidiomycota | do | Yes |
| Hypholoma fasciculare | Basidiomycota | do | Yes |
| Irpex lacteus | Basidiomycota | do | Yes |
| Laetisaris arvalis | Basidiomycota | do | Yes |
| Lyophyllum sp. | Basidiomycota | do | Yes |
| Marasmiellus ramealis | Basidiomycota | do | Yes |
| Merismodes sp. | Basidiomycota | do | Yes |
| Merulius tremellosus | Basidiomycota | do | Yes |
| Oxyporus corticola | Basidiomycota | do | Yes |
| Oxyporus sp. | Basidiomycota | CBS 422.97 | Yes |
| Panaeolus semiovatus | Basidiomycota | CBS 819.95 | Yes |
| Paxillus involtus | Basidiomycota | CBS 100231 | Yes |
| Peniophora cinerea | Basidiomycota | NN007373 | Yes |
| Peniophora lycii | Basidiomycota | CBS 686.96 | Yes |
| Peniophora quercina | Basidiomycota | NN 009335 | Yes |
| Podaxis pistillaris | Basidiomycota | ATCC 38868 | Yes |
| Scizophyllum commune | Basidiomycota | NN strain collection | Yes |
| Scizophyllum sp. | Basidiomycota | CBS 443.97 | Yes |
| Sckeletocutis sp. | Basidiomycota | NN strain collection | Yes |
| Steccherinum ochraceum | Basidiomycota | do | Yes |
| Stereum subtomentosum | Basidiomycota | do | Yes |
| Strobilurus tenacellus | Basidiomycota | do | Yes |
| Stropharia cubensis | Basidiomycota | ATCC 13966 | Yes |
| Trametes hirsuta | Basidiomycota | DSM 2987 | Yes |
| Trametes pubescens | Basidiomycota | CBS 100232 | Yes |
| Trametes zonatella | Basidiomycota | NN strain collection | Yes |
| Trechispora farinaceae | Basidiomycota | do | Yes |
| Trichaptum fuscoviolaceum | Basidiomycota | do | Yes |
| Typhula setipes | Basidiomycota | do | Yes |
| Volvariella speciosa | Basidiomycota | do | Yes |

Example 6

Molecular Screening (Other Primersets)

Primersets 522/525, 539/540, 539/538, 539/525 and 537/525 are tested as described in Example 5 above, using 100 pmol of each of the sense and anti-sense degenerate primers. Touchdown PCR is used for amplification (ref: R. H. Don et al. (1991), Nucleic Acid Research, Vol. 19, No. 14) modified for the AmpliTaq Gold (TM). The PCR reaction is performed using a cycle profile of:

```
94° C. - 10 min; 1 cycle
94° C. - 1 min, 60° C. - 1 min, 72° C. - 1.5 min; 2 cycles
94° C. - 1 min, 59° C. - 1 min, 72° C. - 1.5 min; 2 cycles
94° C. - 1 min, 58° C. - 1 min, 72° C. - 1.5 min; 2 cycles
    .
    .
94° C. - 1 min, 52° C. - 1 min, 72° C. - 1.5 min; 2 cycles
94° C. - 1 min, 50° C. - 1 min, 72° C. - 1.5 min; 14 cycles
72° C. - 7 min; 1 cycle.
```

Example 7

Purification and Sequencing of PCR Bands

The PCR fragments can be purified and sequenced using the Jet sorb Gel extraction Kit (Genomed GmbH, Germany) according to the manufacturer's instructions. The nucleotide sequences of the amplified PCR fragments are determined directly on the purified PCR products using 200–300 ng as template, the Taq deoxy-terminal cycle sequencing kit (Perkin-Elmer, U.S.A.), flourescent labeled terminators and 5 pmol sequence primer on a ABI PRISMt 377 DNA Sequencer, Perkin Elmer.

The PCR fragments generated with primer set 522/538, and with approximately 10–20 ng of doublestranded cDNA from Schizophyllum sp. CBS 443.97 as template, was purified and sequenced as described above and the DNA sequence was deduced to (5'- to 3'-):

```
TCTGCCGCATCTGACGGTGTCTATAACCCCGTCCTCAACCTGAT
TATATCAGAAGAGCTTAACGACACCCTCGATGATGCGATGTGC
CCGAACGTCGGCGAATCGGACGCCCAAACGGACGAATGGACGT
CTATTTACGCAGCGCCCATCGCTGAGCGTCTGAACAACAACGCC
GTGGGCGCTAACCTGACCACCACGAACGTTTACAACCTCATGT
CTTTATGCCCCTTCGACACGCTTGCGAAGGAGACGCCGAGCCCC
TTCTGCGATCTCTTT (SEQ ID NO: 31)
``` and translated into amino acid sequence:

```
SAASDGVYNPVLNLIISEELNDTLDDAMCPNVGESDAQTDEWTSIY
AAPIAERLNNNAVGANLTTTNVYNLMSLCPFDTLAKETPSPECDLF
(SEQ ID NO: 32).
```

The doublestranded cDNA was synthesized as described in Example 1.

Example 8

Purification and Characterization of the Phytase From *Peniophora lycii* Expressed in *Aspergillus oryzae*

The *Peniophora lycii* phytase was expressed in and excreted from *Aspergillus oryzae* IFO 4177.

Filter aid was added to the culture broth which was filtered through a filtration cloth. This solution was further filtered through a Seitz depth filter plate resulting in a clear solution. The filtrate was concentrated by ultrafiltration on 3 kDa cut-off polyethersulphone membranes followed by diafiltration with distilled water to reduce the conductivity. The pH of the concentrated enzyme was adjusted to pH 7.5. The conductivity of the concentrated enzyme was 1.2 mS/cm.

The phytase was applied to a Q-sepharose FF column equilibrated in 20 mM Tris/$CH_3COOH$, pH 7.5 and the enzyme was eluted with an increasing linear NaCl gradient (0→0.5M). The phytase activity eluted as a single peak. This peak was pooled and $(NH_4)_2SO_4$ was added to 1.5M final concentration. A Phenyl Toyopearl 650S column was equilibrated in 1.5M $(NH_4)_2SO_4$, 10 mM succinic acid/NaOH, pH 6.0 and the phytase was applied to this column and eluted with a decreasing linear $(NH_4)_2SO_4$ gradient (1.5→0M). Phytase containing fractions were pooled and the buffer was exchanged for 20 mM Tris/$CH_3COOH$, pH 7.5 on a Sephadex G25 column. The G25 filtrate was applied to a Q-sepharose FF column equilibrated in 20 mM Tris/$CH_3COOH$, pH 7.5. After washing the column extensively with the equilibration buffer, the phytase was eluted with an increasing linear NaCl gradient (0→0.5M). The phytase activity was pooled and the buffer was exchanged for 20 mM Tris/$CH_3COOH$, pH 7.5 by dialysis. The dialysed phytase was applied to a SOURCE 30Q column equilibrated in 20 mM Tris/$CH_3COOH$, pH 7.5. After washing the column thoroughly with the equilibration buffer a phytase was eluted with an increasing linear NaCl gradient (0→0.3M). Fractions from the SOURCE 30Q column were analyzed by SDS-PAGE and pure phytase fractions were pooled.

The Peniophora phytase migrates in the gel as a band with $M_r$=67 kDa. N-terminal amino acid sequencing of the 67 kDa component was carried out following SDS-PAGE and electroblotting onto a PVDF-membrane. The following N-terminal amino acid sequence could be deduced:

Leu-Pro-Ile-Pro-Ala-Gln-Asn-

The sequence corresponds to amino acid residues 31–37 in the cDNA derived amino acid sequence.

Accordingly a mature amino acid sequence of the phytase when expressed in Aspergillus is supposed to be no. 31–439 of SEQ ID no 24.

Example 9

Further Characterization of the Purified Phytase of *Peniophora lycii*

The phytase of *Peniophora lycii* was expressed in Aspergillus and purified as described in Example 8.

The phytase activity is measured using the following assay: 10 μl diluted enzyme samples (diluted in 0.1 M sodium acetate, 0.01% Tween20, pH 5.5) were added into 250 μl 5 mM sodium phytate (Sigma) in 0.1 M sodium acetate, 0.01% Tween20, pH 5.5 (pH adjusted after dissolving the sodium phytate; the substrate was preheated) and incubated for 30 minutes at 37° C. The reaction was stopped by adding 250 μl 10% TCA and free phosphate was measured by adding 500 μl 7.3 g $FeSO_4$ in 100 ml molybdate reagent (2.5 g $(NH_4)_6Mo_7O_{24}\cdot 4H_2O$ in 8 ml $H_2SO_4$ diluted to 250 ml). The absorbance at 750 nm was measured on 200 μl samples in 96 well microtiter plates. Substrate and enzyme blanks were included. A phosphate standard curve was also included (0–2 mM phosphate). 1 FYT equals the amount of enzyme that releases 1 μmol phosphate/min at the given conditions.

Temperature profiles were obtained by running the assay at various temperatures (preheating the substrate).

Temperature stability was investigated by preincubating the phytases in 0.1 M sodium phosphate, pH 5.5 at various temperatures before measuring the residual activity.

The pH-stability was measured by incubating the enzyme at pH 3 (25 mM glycine-HCl), pH 4–5 (25 mM sodium acetate), pH 6 (25 mM MES), pH 7–9 (25 mM Tris-HCl) for 1 hour at 40° C., before measuring the residual activity.

The pH-profiles were obtained by running the assay at the various pH using the same buffer-systems (50 mM, pH was re-adjusted when dissolving the substrate).

The results of the above pH-profile, pH-stability, temperature-profile and temperature stability studies are shown in FIGS. 8, 9, 10 and 11, respectively. From FIG. 9 it appears that the phytase of Peniophora lycii is very stable (i.e. more than 80% of the maximum activity retained) for 1 hour at 40° C. in the whole range of pH 3–9. And as regards the temperature stability results shown at FIG. 11, it appears that at 60–80° C. some 50–60% of the residual activity still remains. This fact is contemplated to be due to the enzyme being surprisingly capable of refolding following its thermal denaturation. The degree of refolding will depend on the exact conditions (pH, enzyme concentration).

Figure 12:
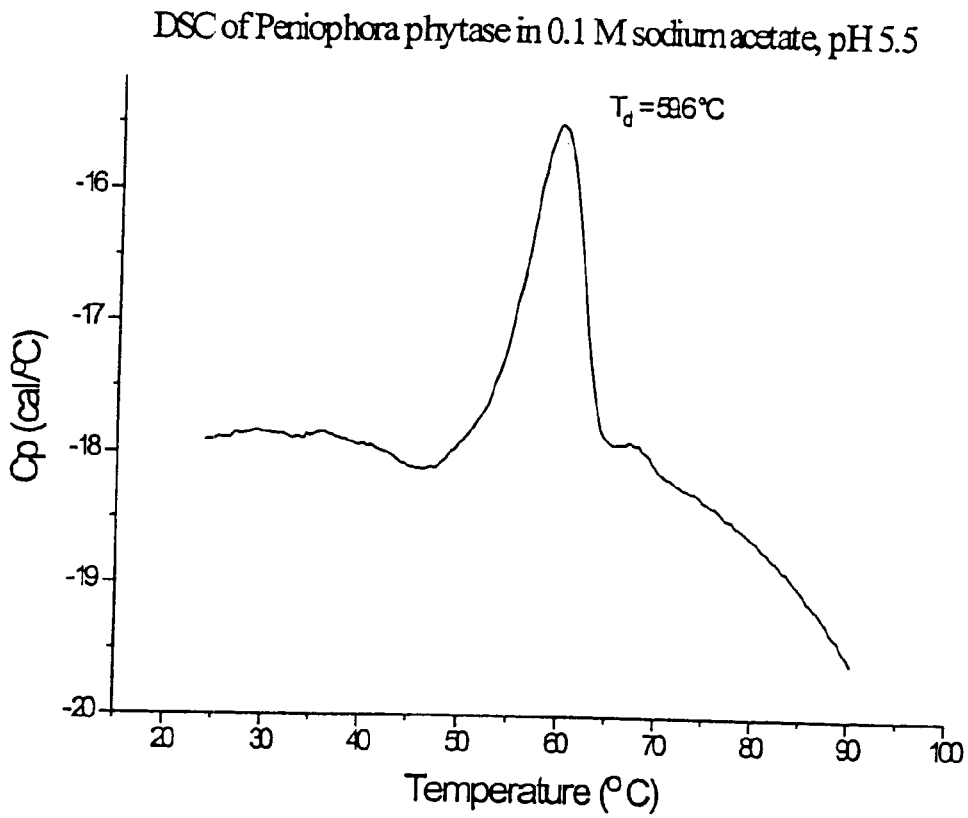
FIG. 12 a Differential Scanning Calorimetry (DSC) curve thereof.

FIG. 12 shows the result of differential scanning calorimetry (DSC) measurements on the Peniophora phytase. In DSC the heat consumed to keep a constant temperature increase in the sample-cell is measured relative to a reference cell. A constant heating rate is kept (e.g. 90° C./hour). An endothermal process (heat consuming process—e.g. the unfolding of an enzyme/protein) is observed as an increase in the heat transferred to the cell in order to keep the constant temperature increase. DSC was performed using the MC2-apparatus from MicroCal. Cells were equilibrated 20 minutes at 20° C. before scanning to 90° C. at a scan rate of 90°/h. Samples of around 2.5 mg/ml Peniophora phytase in 0.1 M sodium acetate, pH 5.5 were loaded.

Example 10

Determination of the Specific Activity of the Peniophora phytase

The specific activity is determined on a highly purified sample of the phytase (the purity was checked beforehand on an SDS poly acryl amide gel showing the presence of only one component).

The protein concentration in the phytase sample was determined by amino acid analysis as follows: An aliquot of the phytase sample was hydrolyzed in 6N HCl, 0.1% phenol for 16 h at 110 C. in an evacuated glass tube. The resulting amino acids were quantified using an Applied Biosystems 420A amino acid analysis system operated according to the manufacturers instructions. From the amounts of the amino acids the total mass—and thus also the concentration—of protein in the hydrolyzed aliquot can be calculated.

The activity is determined in the units of FYT. One FYT equals the amount of enzyme that liberates 1 micromol inorganic phosphate from phytate (5 mM phytate) per minute at pH 5.5, 37 C.; assay described e.g. in example 11.

The specific activity is calculated to 987 FYT/mg enzyme protein.

Example 11

Time-Resolved Product-Profiling of Phytase-Catalyzed Hydrolysis of Phytic Acid by $^1$H NMR Spectroscopy The hydrolysis of phytic acid (PA) catalyzed by the Peniophora phytase and by a commercial Aspergillus niger phytase (Phytase Novo®) was investigated (27 mM phytate, 1 FYT/ml, pH 5.5 and 3.5, and 27° C.) by $^1$H NMR profiling the product mixture in the course of 24 hours.

In the following (Ins(p,q,r, . . . )$P_n$ denotes myo-inositol carrying in total n phosphate groups attached to positions p, q, r, . . . For convenience Ins(1,2,3,4,5,6)$P_6$ (phytic acid) is abbreviated PA. Please refer, however, to the section "Nomenclature and position specificity of phytases" in the general part of this application.

The technique provide specific information about initial points of attack by the enzyme on the PA molecule, as well as information about the identity of the end product. On the other side the evolving patterns of peaks reflecting the composition of the intermediate product mixtures, provide a qualitative measure, a finger print, suitable for identification of similarities and differences between individual enzymes.

NMR, like most other analytical methods, can distinguish between stereo-isomers which are not mirror images (diastereomers), but not between a set of isomers, which are mirror-images (enantiomers), since they exhibit identical NMR spectra.

Thus, Ins(1,2,4,5,6)$P_5$ (3-phosphate removed) exhibits a NMR spectrum different from Ins(1,2,3,4,5)$P_5$ (6-phosphate removed) because the isomers are diastereomers.

However, the NMR spectra of Ins(1,2,4,5,6)$P_5$ and Ins(2, 3,4,5,6)$P_5$ (1-phosphate removed) are identical because the isomers are enantiomers. The same holds for the pair Ins(1, 2,3,4,5)$P_5$ and Ins(1,2,3,5,6)$P_5$ (4-phosphate removed).

Thus, by NMR it is not possible to distinguish between a 3- and a 1-phytase, and it is not possible to distinguish between a 6- and a 4-phytase (or a L-6- and a D-6-phytase using the lowest-locant rule).

Biased by the description of 3- and 6-phytases in the literature, we have used the terms 3- and 6-phytases for our enzymes, but, though unlikely, we do not actually know if we have a 1- and a 4-phytase instead.

Experimental

NMR spectra were recorded at 300 K (27° C.) on a Bruker DRX400 instrument equipped with a 5 mm selective inverse probe head. 16 scans preceded by 4 dummy scans were accumulated using a sweep width of 2003 Hz (5 ppm) covered by 8 K data points. Attenuation of the residual HOD resonance was achieved by a 3 seconds presaturation period. The spectra were referenced to the HOD signal (δ 4.70).

PA samples for NMR analysis were prepared as follows: PA (100 mg, Phytic acid dipotassium salt, Sigma P-5681) was dissolved in deionized water (4.0 ml) and pH adjusted to 5.5 or 3.5 by addition of aqueous NaOH (4 N). Deionized water was added (ad 5 ml) and 1 ml portions, each corresponding to 20 mg of phytic acid, were transferred to screw-cap vials and the solvent evaporated (vacuum centrifuge). The dry samples were dissolved in deuterium oxide (2 ml, Merck 99.5% D) and again evaporated to dryness (stored at −18° C. until use).

For NMR analysis one 20 mg phytic acid sample was dissolved in deuterium oxide (1.0 ml, Merck 99.95% D). The solution was transferred to a NMR tube and the $^1$H NMR spectrum recorded.

Enzyme solution (1 FTU, dissolved in/diluted, as appropriate, with deuterium oxide) was added followed by thorough mixing (1 minute). $^1$H NMR spectra were recorded immediately after addition of enzyme (t=0), then after 5, 10, 15, 20, 25, 30, 45, 60, 75, 90, 105, 120, 135 150, 165, 180, 195, 210 minutes (=3.5 hours), 4.5, 5.5 6.5, 7.5, 8.5, 9.5, 11.5, 13.5, 15.5, 17.5, 19.5, 21.5, and 23.5 hours. The pH in the NMR tube was measured. Additional spectra were acquired after 48 and 120 hours (5 days), where a portion of substrate (PA, 6 mg) was added to probe if the enzyme retained its catalytic activity.

By means of 2D NMR analysis of inositol phosphate mixtures obtained by partial digestion of PA, in conjunction with published NMR data (Scholz, P.; Bergmann, G., and Mayr, G. W.: *Methods in Inositide Research* (Ed. Irvine, R. F.), pp. 65–82, Raven Press, Ltd., New York (1990)), characteristic $^1$H NMR signals attributable to Ins(1,2,3,4,5,6)P$_6$ (PA), Ins(1,2,4,5,6)P$_5$, Ins(1,2,3,4,5)P$_5$, Ins(1,2,5,6)P$_4$, Ins (1,2,6)P$_3$, Ins(1,2)P$_2$, and Ins(2)P, were identified and permitted relative quantification of these species during the course of the reaction.

Figure 13:
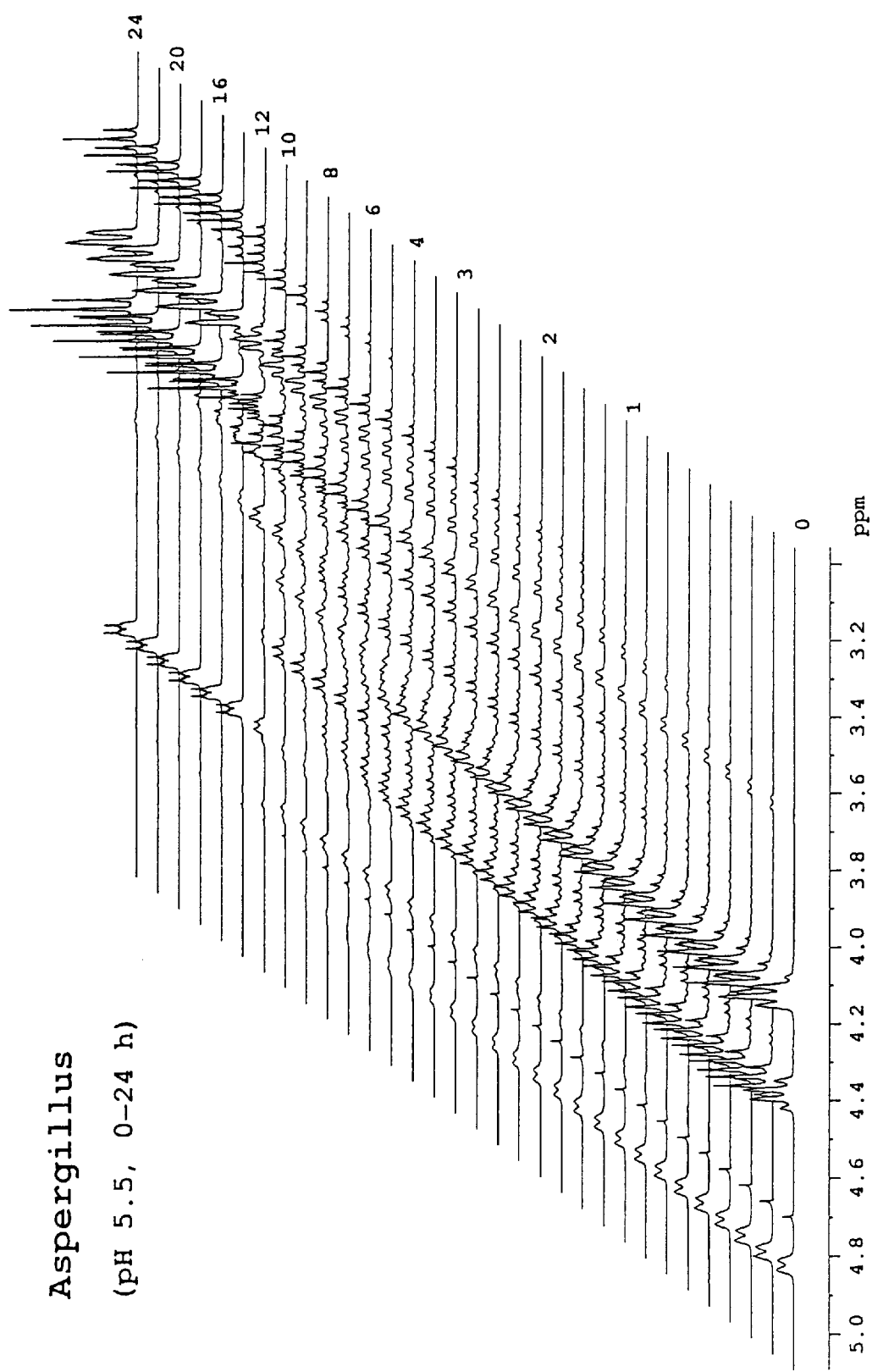
FIGS. 13–14 NMR spectra, stacked plots (up to 24 h), showing the product profiling of an *Aspergillus niger* and the Peniophora phytase, respectively.
Figure 14:
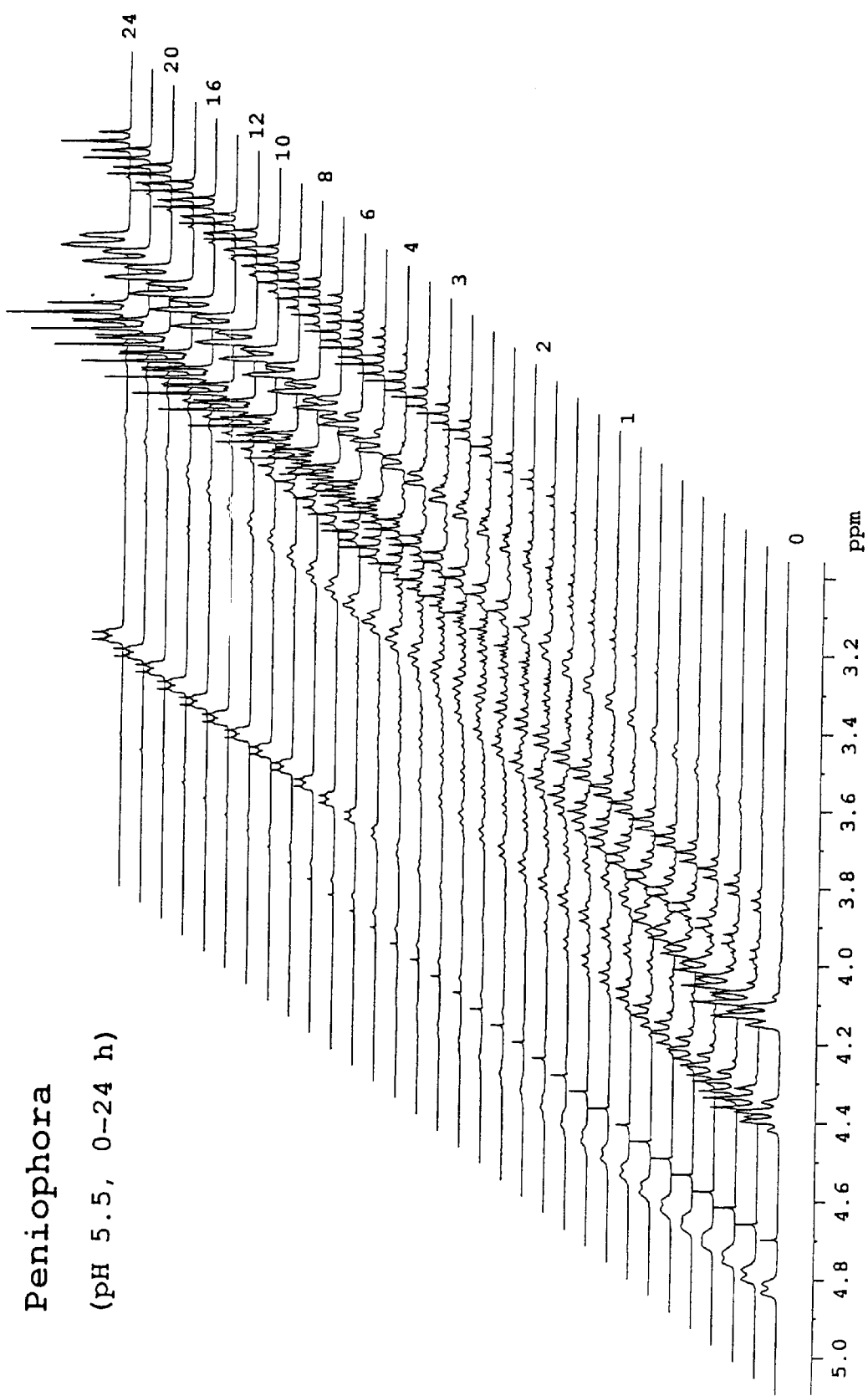

Stacked plots of product profiles for the Aspergillus phytase and the Peniophora phytase covering 24 hours of reaction time at pH 5.5 is presented in FIG. 13 and FIG. 14, respectively.

The signal at δ 3.25(t) represents H-5 in Ins(1,2)P$_2$ whereas the signal at δ 3.18(t) represents H-5 in Ins(2)P. Ins(1,2)P$_2$ starts accumulating after about 4 hours of reaction time with the Aspergillus phytase and after about 1 hours of reaction time with the Peniophora phytase. Ins(2)P is observed after about 10 hours of reaction with the Aspergillus phytase and after about 3 hours of reaction with the Peniophora phytase. After 24 hours of reaction the amount or level of Ins(1,2)P$_2$ is very low for both phytases, whereas the amount of Ins(2)P is maximum for both phytases after 24 hours.

Accordingly, the profiles observed after 24 hours of reaction time demonstrate that both phytases degrade PA to Ins(2)P.

For both enzymes the reaction mixture at 24 h comprised in addition to Ins(2)P minor amounts of Ins(1,2)P$_2$. Prolonged reaction times (several days) resulted in disappearance of the residual Ins(1,2)P$_2$, but the fully dephosphorylated species, inositol (Ins), was not observed at all. The observation is not explained by irreversible inhibition/denaturation of the enzyme, since the enzymes retained their catalytic activities for prolonged periods, as demonstrated by their ability to digest fresh portions of PA added to the NMR tubes after keeping them 5 days at room temperature.

Figure 15:
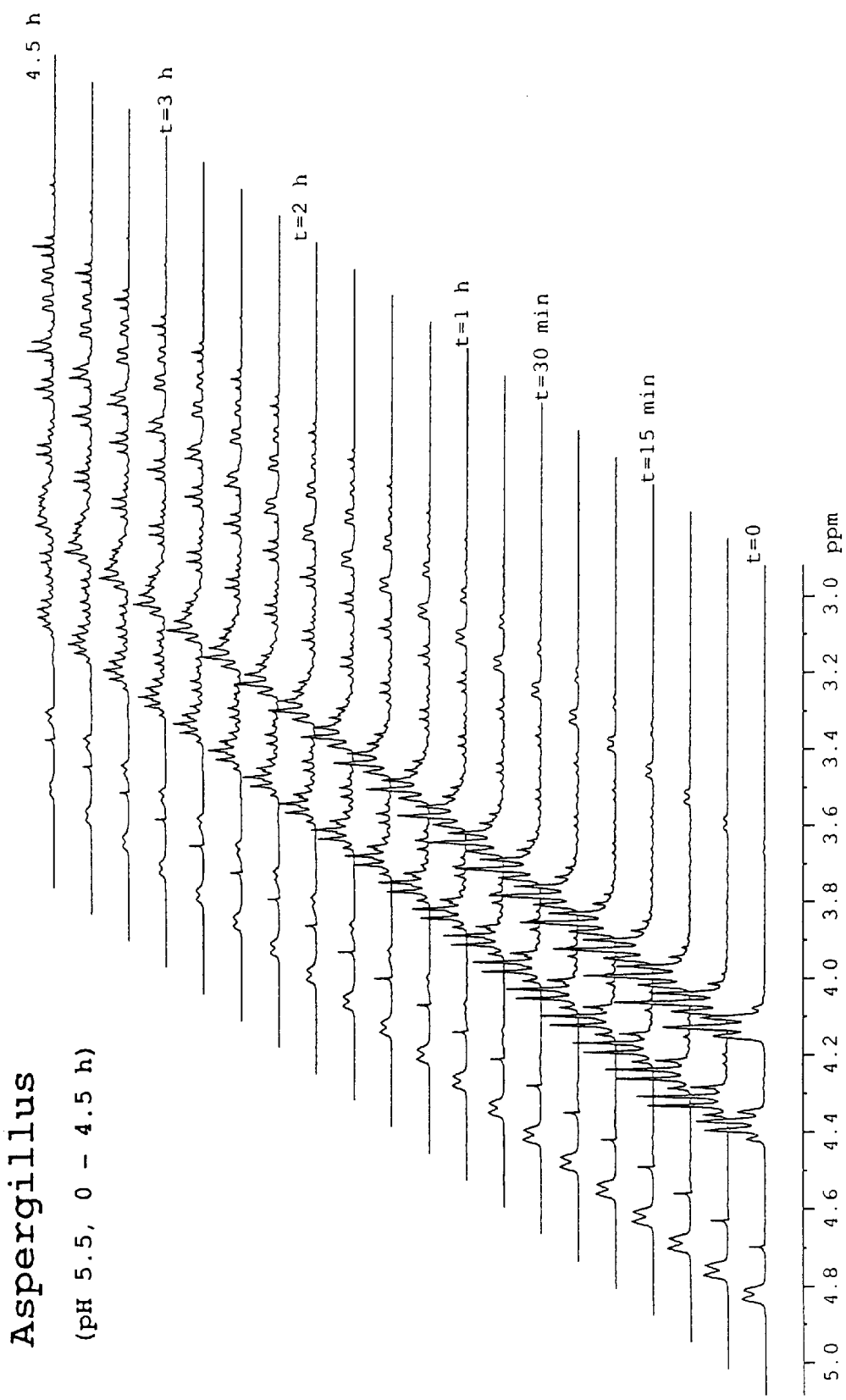
FIGS. 15–16 NMR spectra as above, but stacked plots up to 4.5 h.
Figure 16:
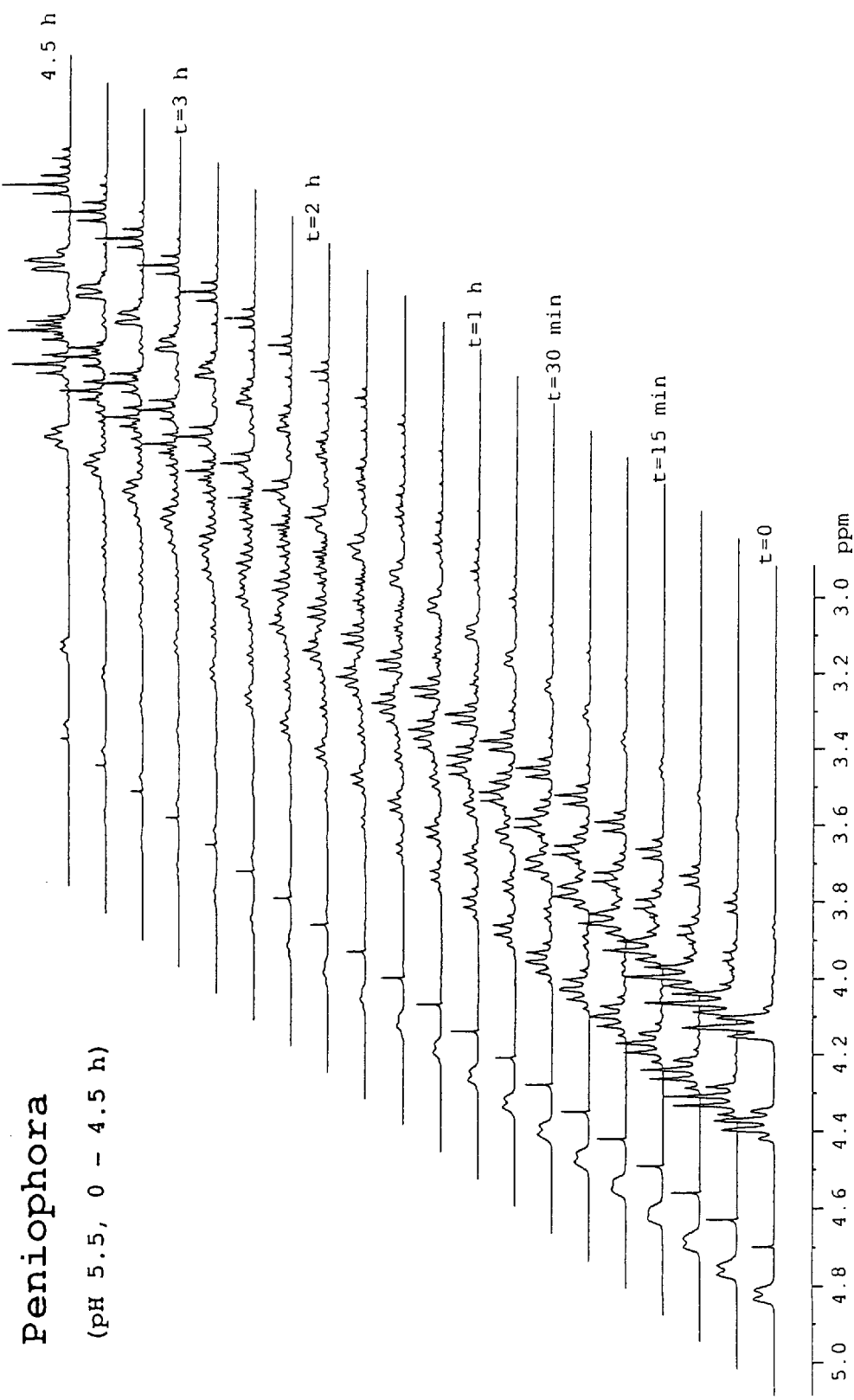

Turning now to FIGS. 15 and 16, these depict in more detail the profiles evolving at pH 5.5 during the initial 4.5 hours. It is inferred from FIG. 10 that H-3 in Ins(1,2,4,5,6)P$_5$ (designated A) shows a signal at δ 3.66(dd), H-6 in Ins(1, 2,3,4,5)P$_5$ (B) a signal at δ 3.87(t) and H-3 in Ins(1,2,5,6)P$_4$ (C) a signal at δ 3.56(dd). Now, compound A corresponds to phosphate in position 3 having been hydrolyzed, B position 6 and C position 3 and 4.

It is apparent from FIG. 15 that compound A appears as the major primary product (t=5 min) using the Aspergillus phytase, whereas compound B does not appear. Compound C appears after 20–25 minutes.

From FIG. 16 (the Peniophora phytase) one infers that compound B appears as the major primary product (t=5 min) using the Peniophora phytase.

The signals at δ 4.82(dt, H-2), 4.38 (q, H-4/H-6), 4.13(q, H-5) and 4.11(dt,H1/H3) are attributable to the substrate, phytic acid, PA. Comparing FIGS. 15 and 16 it is apparent, that these peaks diminish faster with the Peniophora phytase than with the Aspergillus phytase.

Figure 17:
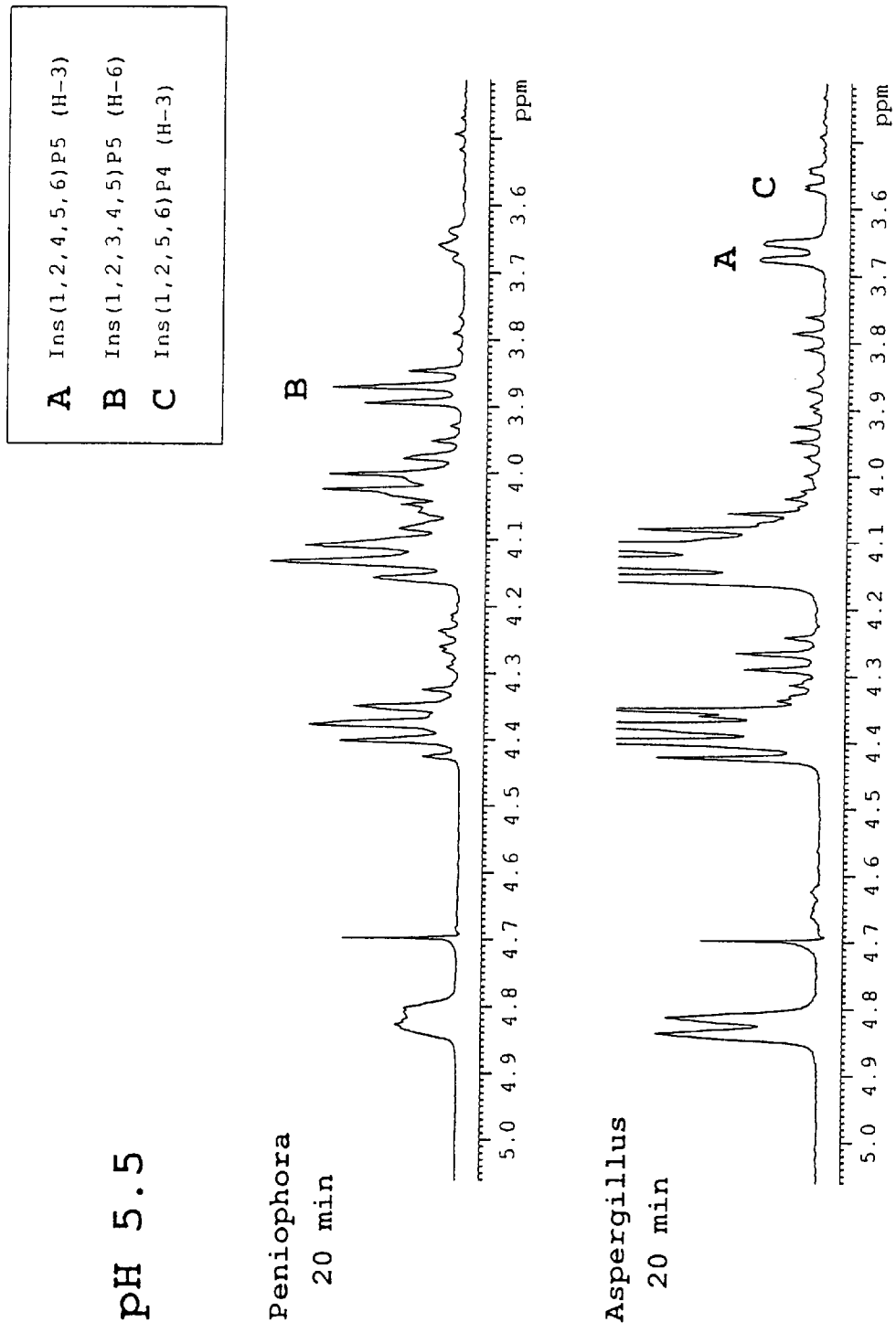
FIGS. 17–19 NMR profiles observed after 20 minutes (at pH 5.5), 24 hours (at pH 5.5) and 20 minutes (at pH 3.5), respectively.

These differences are highlighted in FIG. 17, which present the profiles observed after 20 min at pH 5.5 with the above indicated diagnostic signals (A,B,C) labelled.

Figure 18:
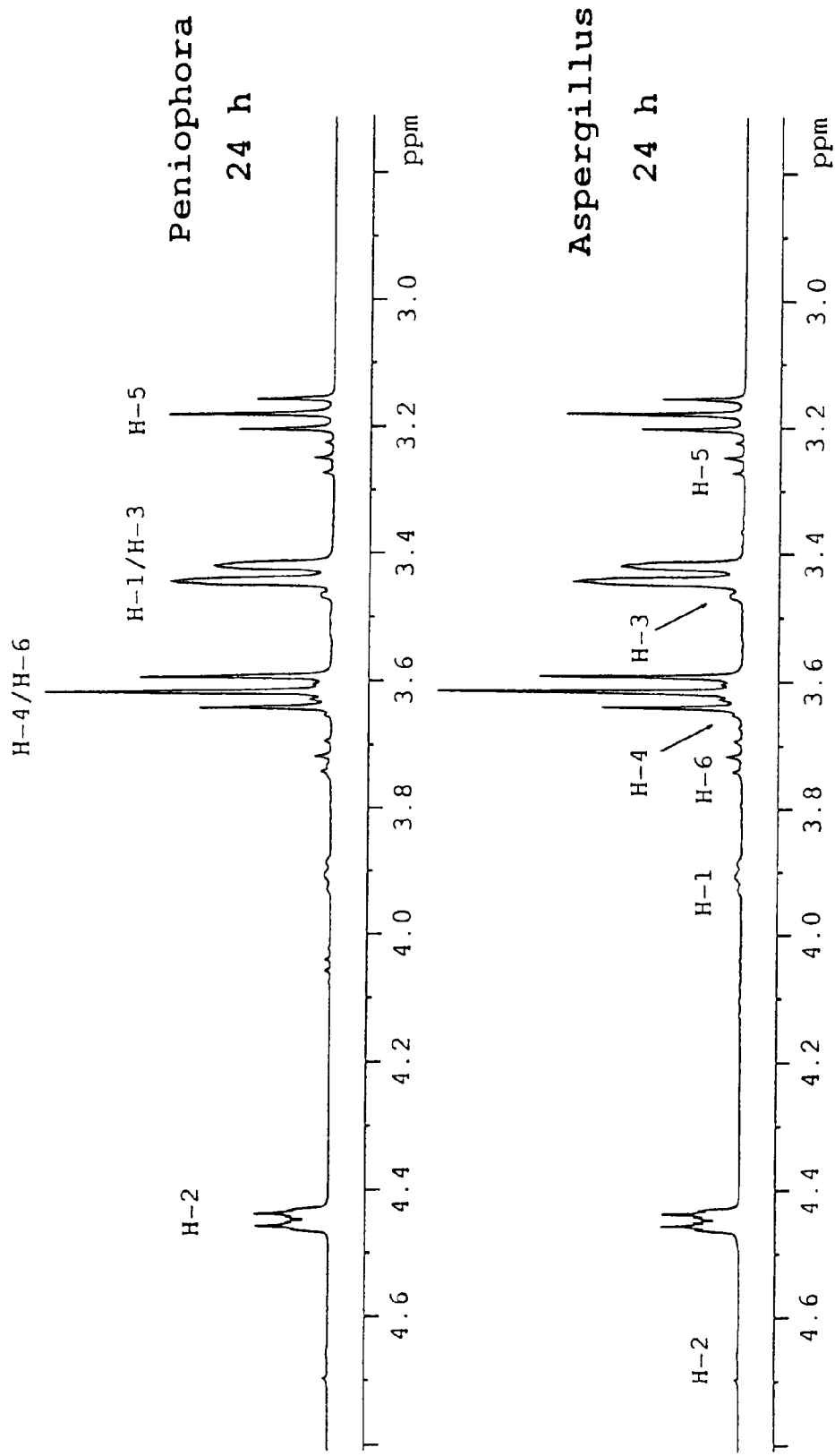

FIG. 18 shows the final result (under these conditions) of the hydrolysis of phytic acid at pH 5.5 (i.e. corresponding to the upper line of FIGS. 13 and 14). All signals labelled at the upper Peniophora embodiment represent the compound Ins (2)P, viz. the protons thereof, from the right to the left: H-5, H1 and H3, H4 and H6 and finally H-2. Relative intensity: 1:2:2:1. The corresponding signals are found in the bottom embodiment of Aspergillus. This means that the end product is in both embodiments Ins(2)P. However, a minor amount of Ins(1,2)P$_2$ is also detected in both embodiments, the corresponding peaks being indicated at the Aspergillus embodiment only.

Figure 11:
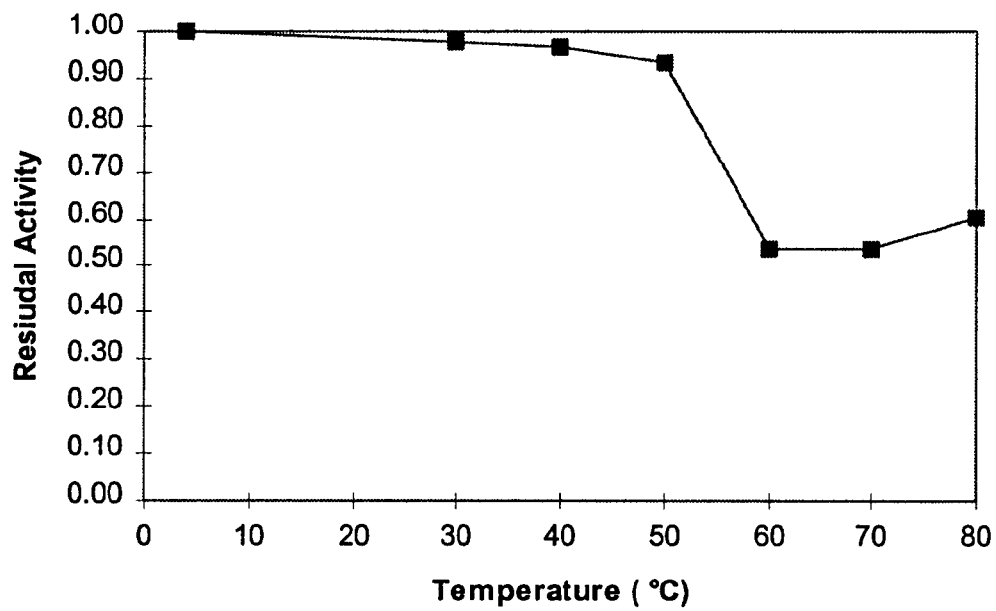
FIG. 11 a temperature-stability curve thereof.

Marked differences are observed:

Aspergillus: The initial major product was identified as Ins(1,2,4,5,6)P$_5$ (A) followed by appearance of Ins(1,2,5,6)P$_4$ (C) and Ins(1,2,6)P$_3$ (D) (H-3 at δ 3.49(dd) after 1½ hours) corresponding to consecutive removal of the phosphate groups in the 3-, 4- and 5-positions. The concentration of Ins(1,2)P$_2$ (E) builds up slowly starting at 4 hours and decreases very steeply between 12 and 14 hours with a concomitant rapid increase of the Ins(2)P (F) level. This is visualized in FIG. 11 representing the time dependent concentration of Ins(1,2)P$_2$ and Ins(2)P, respectively, determined by measuring the area under the signals corresponding to H-5 in Ins(1,2)P$_2$ (δ 3.25(t)) and Ins(2)P (δ 3.18 (t)), respectively, relative to the area under the signals corresponding to the substrates (t=0).

Peniophora: At pH 5.5 only the 6-position is initially attacked. A characteristic feature is that PA is digested at a faster rate compared to the Aspergillus phytase. Additional characteristic features are that the end product, Ins(2)P (F) appears very early (3 hours) and builds up slowly, in contrast to the very steep increase in the Ins(2)P-level towards the end of the reaction observed for the Aspergillus phytase.

Figure 19:
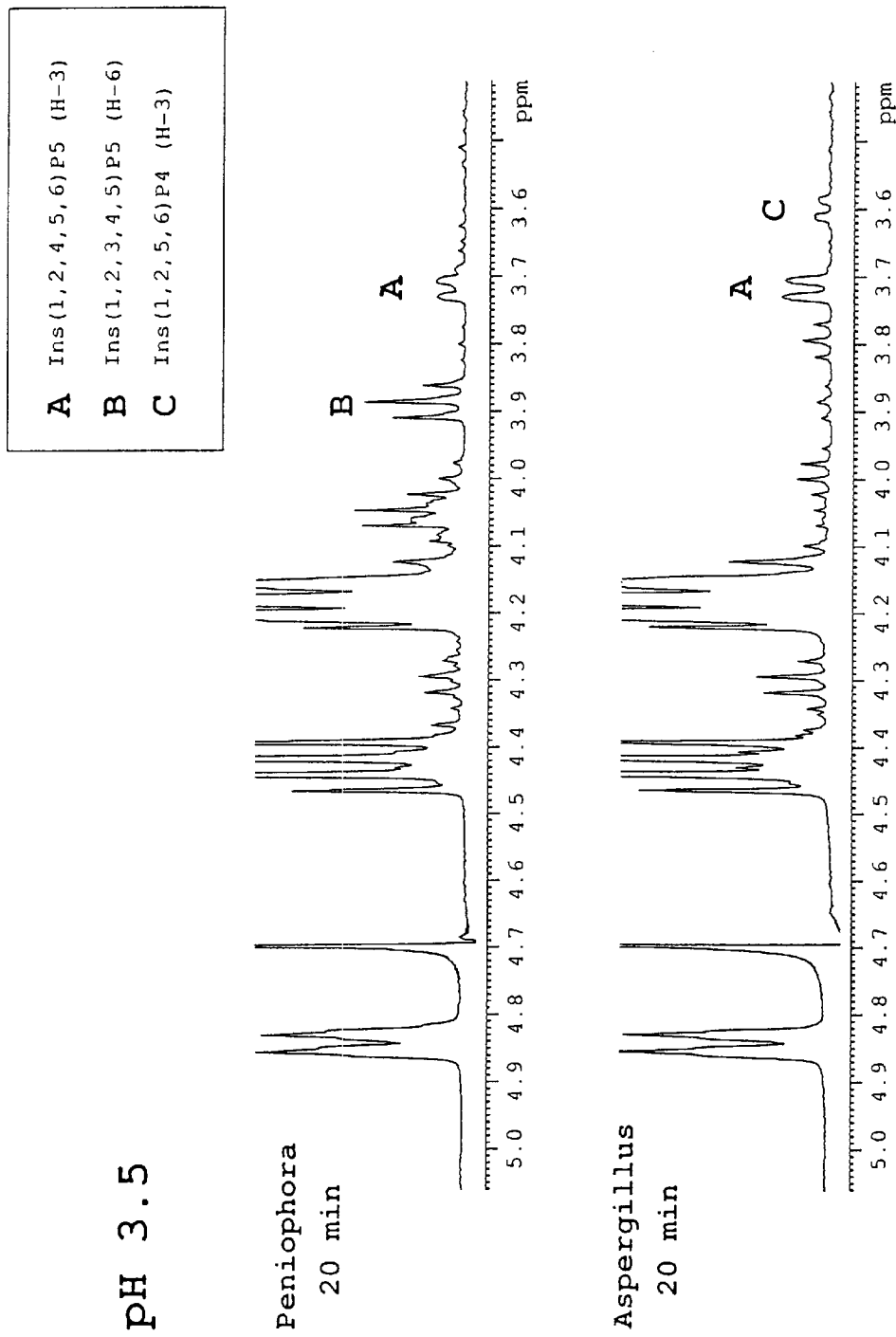

FIG. 19 is a plot similar to FIG. 17, but at pH 3.5. Surprisingly, at this pH the Peniophora phytase turns up to have high initial affinity to the 6- as well as the 3-position of PA (B as well as A are observed), probably with a slight preference for the 6-position.

The data generated permit i.a. the following conclusions:

At pH 5.5 as well as 3.5 the Aspergillus phytase attacks with a high degree of selectivity PA in the 3-position, whereas the Peniophora phytase at pH 5.5 with a high degree of selectivity attacks PA in the 6-position, at pH 3.5 however it seems to hydrolyze the phosphate groups at the 3- and 6-positions at comparable rates.

At pH 5.5, the Peniophora phytase digests PA at a faster rate compared to the Aspergillus phytase.

The end-product is, at pH 3.5 as well as 5.5, under the conditions applied, Ins(2)P (F).

Figure 20:
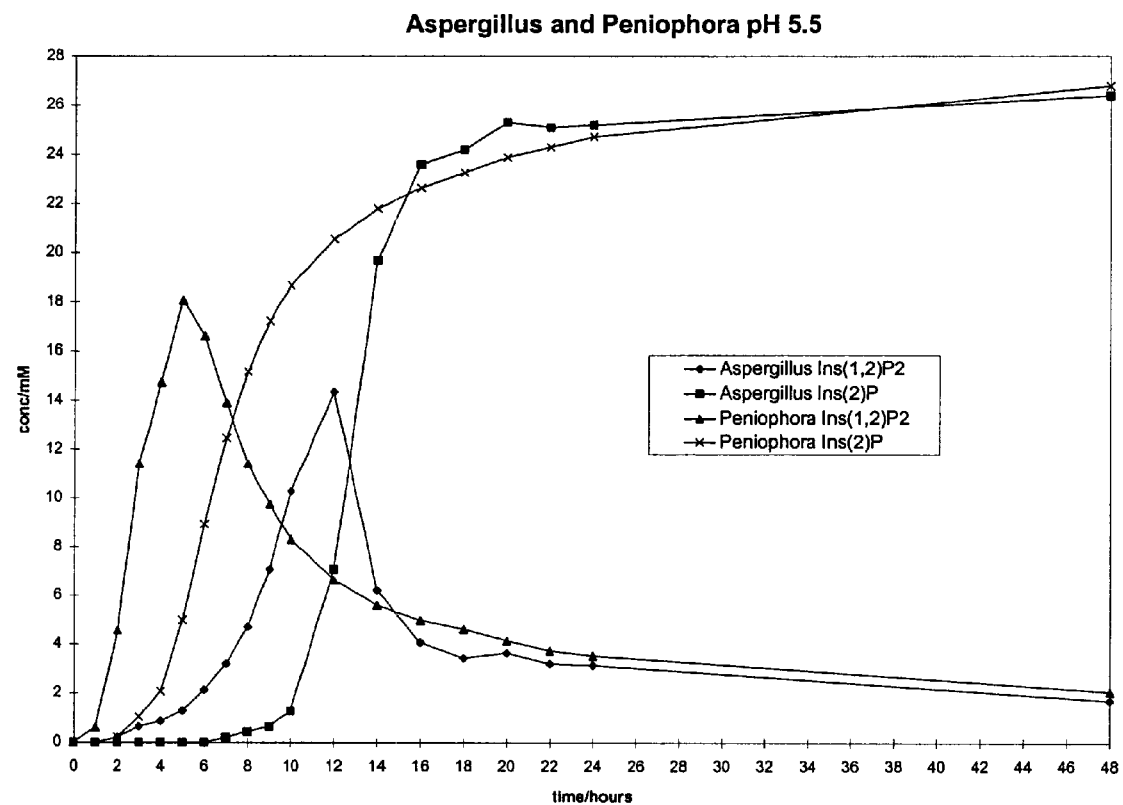
FIG. 20 curves showing concentration versus time of Ins(1,2)P2 and Ins(2)P, respectively.

The overall reaction rates (PA→Ins(2)P) were comparable, approximately 20 hours (FIG. 20; pH 5.5).

Accordingly, the Aspergillus phytase prove to be an essentially clean 3-phytase, whereas the Peniophora phytase at pH 5.5 appear to be an essentially clean 6-phytase and at pH 3.5 a phytase of a hitherto unknown type, viz a 3+6-phytase.

The exact configuration of myo-inositol tetrakisphosphate produced by partial hydrolysis af phytic acid with the Peniophora phytase could be determined as outlined below, also allowing us to conclude whether the Peniophora phytase is a D-, L- or a D/L-6-phytase.

Other ways of determining the exact specificity is by determining optical rotation or using a chiral HPLC column.
1. HPLC-isolation of myo-inositol tetrakisphosphate produced by partial degradation of phytic acid with the Peniophora phytase. Desalting (ion exchange, dialysis, (2), (4) and (9) and references herein)
2. NMR analysis to check purity (i), determine whether several diastereomer tetrakisphosphates are produced (ii), and determine which of these are produced (iii)
3. Synthesis of relevant polyols using reduction by boronhydrid (BH) of the corresponding carbonhydrates (10)
4. Disintegration using periodate, reduction by boronhydrid and dephosphorylation following (2). Identification of polyol using HPLC 5. Oxidation of polyol using L-iditol dehydrogenase and final identification of carbonhydrid using HPLC.

References:
(2) Van der Kaay et al, Biochem. J., 312 (1995), 907–910
(4) Irving et al, J. Bacteriology, 112 (1972), 434–438
(9) Stevens, L. R. in "Methods in Inositide Research" (Irvine, R. F. Ed.), 9–30 (1990), Raven Press, Ltd., New York.
(10) Stephens, L. et al, Biochem. J., 249 (1988), 271–282

Example 12

Comparative Assay, Aspergillus and Peniophora Phytase Release of Inorganic Phosphate From Corn The present example gives a simple assay for the phytase catalyzed liberation of phosphorous from corn at pH 3.5 and 5.5. Two parameters have been focused on—velocity and level of P-liberation.

Materials and Methods

Corn was obtained from North Carolina State University (sample No. R27), and ground at a mill (Buhler Universal) at point 6.8.

A corn-suspension (16.7% w/w) was prepared by weighing 20 g of ground corn into a 250 ml blue cap bottle and adding 100 ml of buffer.

The following buffer was used:
pH 5.5: 0.22 M acetate-buffer
The pH value of 3.5 was adjusted by 8N HCl/NaOH.

Enzymes tested: Two phytases was tested: A commercial phytase of *Aspergillus niger* (Phytase Novo®) and a Peniophora phytase of the invention, purified as described in example 2. Dosage: All enzymes were applied at 25 FYT/20 g corn (correspond to 1250 FYT/kg).

The bottles with the corn suspension were closed by caps, and immediately placed in a water bath at 37° C. and subjected to constant stirring. pH was measured at this stage and again after 24 hours. After 30 min of stirring a sample of 5 ml was collected.

Then the phytase enzymes were added at a dosage of 25 FYT/20 g of corn.

Samples were then collected 5, 10, 15, 20, 25, 30, 40, 50, 60 and 120 min after the addition of the phytases, and the content of released P determined as follows:

Phytase containing samples were diluted 1+4 in buffer. Then the samples were centrifuged at 3000 rpm for 5 min, and 1.0 ml of the supernatant was collected. 2.0 ml buffer and 2.0 ml MoV stop solution (cfr. the FYT assay of Example 6) was added. The samples were placed in a refrigerator at 3–5° C. until all samples could be measured at the spectrophotometer at 415 nm.

pH was measured at time 0 and 20 hours.

For the determinations a phosphate standard or stock solution of
50 mM was used prepared. 0.5, 1.0, 1.5 and 2.0 ml stock solution is diluted to a total volume of 50 ml using buffer. 3.0 ml of each solution is added 2.0 ml MoV stop solution.

Figure 21:
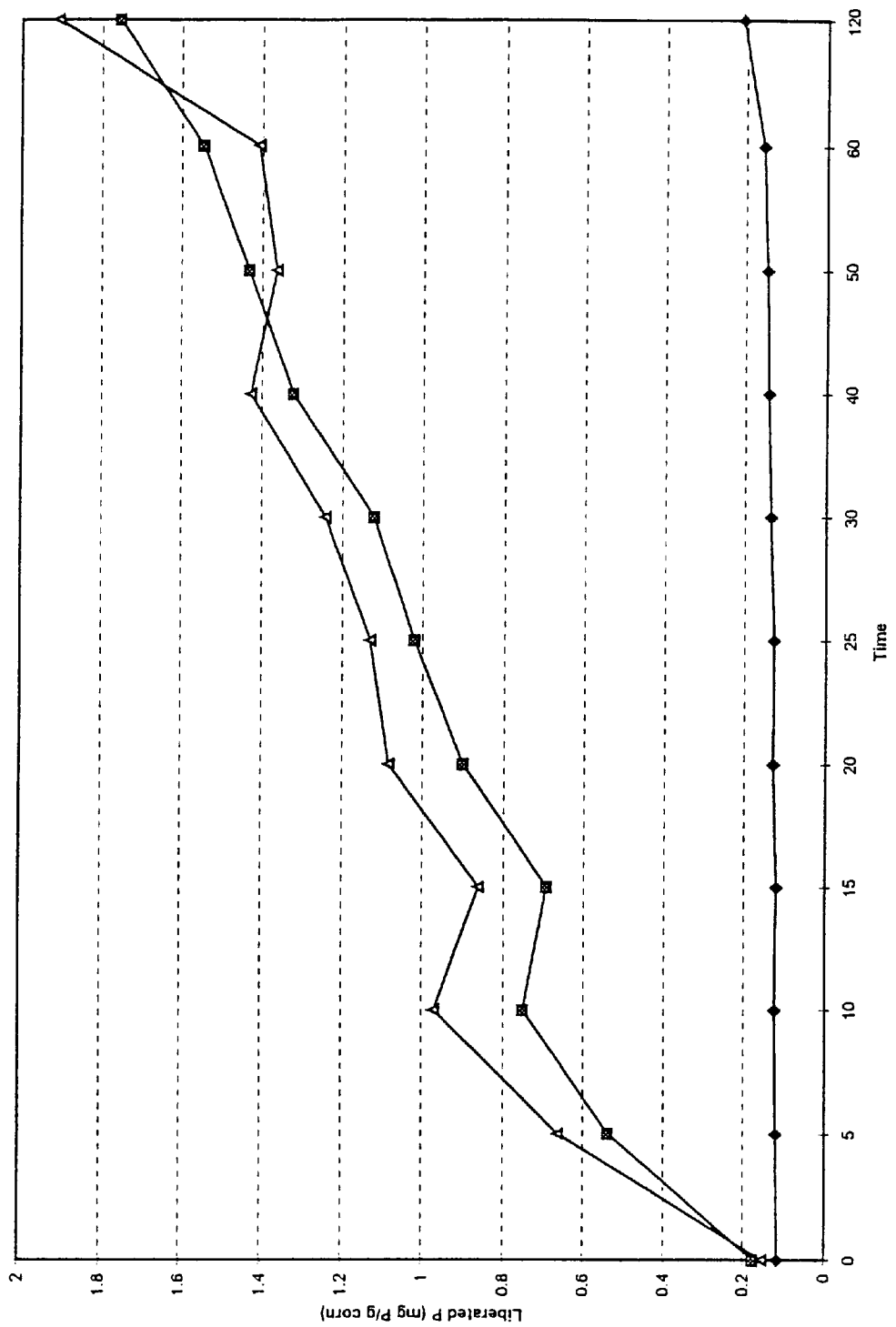
FIGS. 21–22 curves showing the release of inorganic phosphate versus time from corn at pH 5.5 and pH 3.5, respectively.
Figure 22:
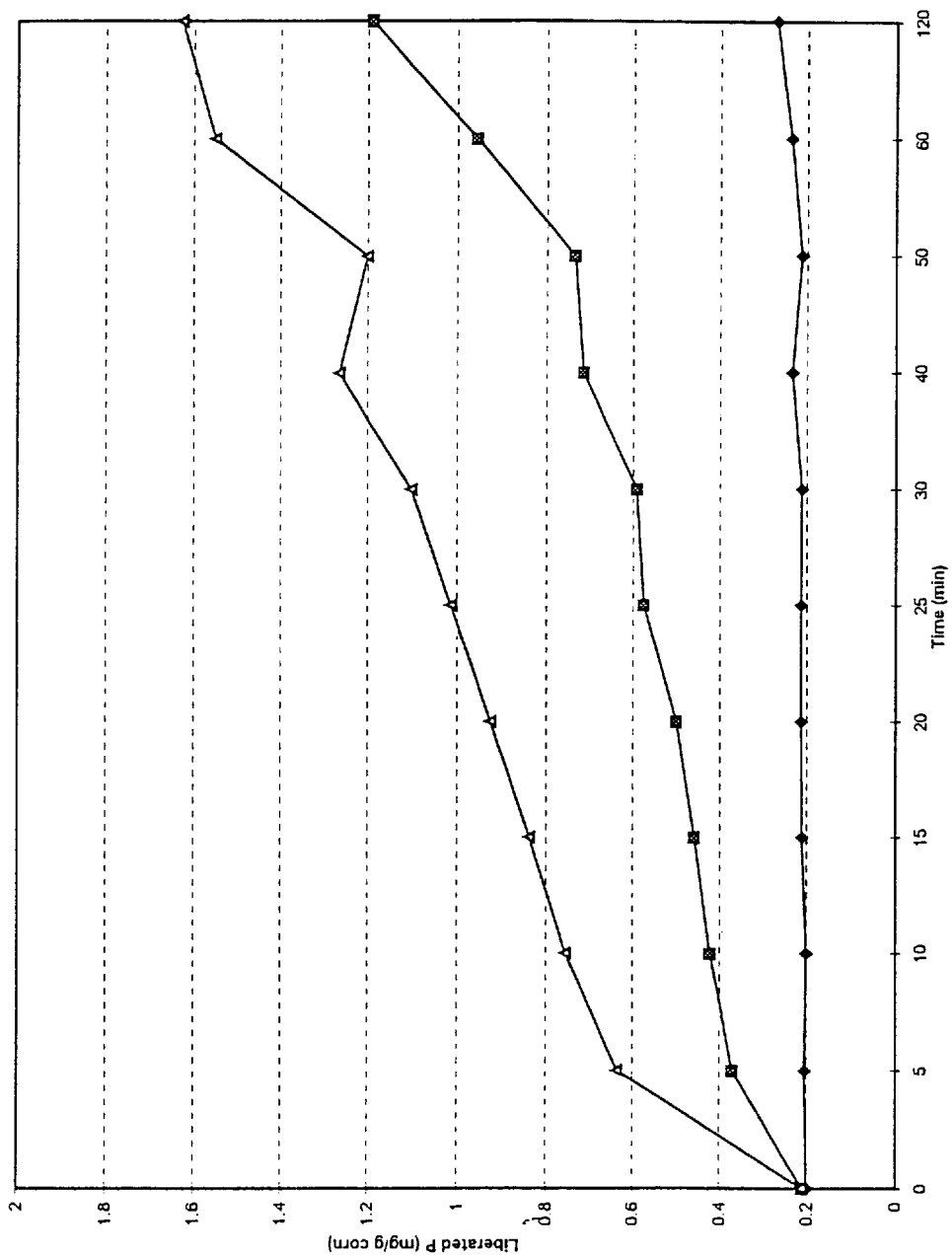

Two experiments were conducted: at pH 5.5 and at pH 3.5. The analysis results are shown at FIGS. 21 and 22 (pH 5.5 and 3.5, respectively). At these figures, symbol "♦" represents the control experiment, "▲" the Peniophora phytase and "■" the Aspergillus phytase.

Results and Discussion

FIG. 21 (pH 5.5) shows, that at this pH the Peniophora phytase liberates P from corn at significantly improved rate as compared to the Aspergillus phytase.

From FIG. 22 (pH 3.5) it is clearly apparent that at this pH the Peniophora phytase is much faster in the liberation of phosphorous from ground corn as compared to the Aspergillus phytase (0–120 minutes).

The passage time of the digestive system of for instance chickens/broilers is normally is of the order of magnitude of 30 minutes to 2 hours, so the observed difference is for sure important, whatever the pH. Nevertheless the pH value of 3.5 is more relevant in this respect than the pH 5.5 value.

This implies that the Peniophora enzyme is surprisingly more efficient than the known Aspergillus phytase as a P-liberator in the digestive system of e.g. broilers.

Example 13

Fermentation, Purification and Characterization of the Phytase of *Agrocybe pediades* Expressed in Yeast A seed culture is prepared by incubation of the yeast strain in 100 ml medium A at 250 rpm over night at 30° C. 100 ml medium B is inoculated with 2 ml seed culture and the strains incubate for 7 to 12 days at 30° C. 250 rpm.

*Agrocybe pediades* phytase was expressed in yeast as described in Example 2. The yeast clone comprises a cloned sequence encoding a phytase of the invention having the amino acid sequence shown in SEQ ID No 22.

Filter aid was added to the culture supernatant which was filtered through a filtration cloth. This solution was further filtered through a Seitz depth filter plate resulting in a clear solution. The filtrate was concentrated by ultrafiltration on 3 kDa cut-off polyethersulphone membranes and refiltered on a germ filter plate. The pH of the filtrate was adjusted to pH 7.5 and the conductivity was adjusted to 2 mS/cm by dilution with distilled water.

The phytase was applied to a Q-sepharose FF column equilibrated with 20 mM Tris/CH$_3$COOH, pH 7.5 and the enzyme was eluted with an increasing linear NaCl gradient (0→0.5M). The phytase containing fractions from the Q-sepharose column were pooled and (NH$_4$)$_2$SO$_4$ was added to 1.3M final concentration. A Phenyl Toyopearl 650S column was equilibrated with 1.3M (NH$_4$)$_2$SO$_4$, 10 mM succinic acid/NaOH, pH 6.0 and the phytase was applied to this column and eluted with a decreasing linear (NH$_4$)$_2$SO$_4$ gradient (1.3→0M). Phytase containing fractions were pooled and buffer was exchanged with 20 mM Tris/CH$_3$COOH, pH 7.5 on a Sephadex G25 column. Phytase was further purified on a SOURCE Q column equilibrated with 20 mM Tris/CH$_3$COOH, pH 7.5, and eluted with a linear NaCl gradient (0→0.5M). Finally, phytase containing fractions from the SOURCE Q column were pooled, concentrated on a 10 kDa cut-off regenerated cellulose membrane, and applied to a Superdex 200 column equilibrated in 25 mM CH$_3$COOH/NaOH, 100 mM NaCl, pH 5.0.

Fractions from the Superdex 200 column were analyzed by SDS-PAGE. The phytase migrates in the gel as a very broad and diffuse band with approx. Mr=150 kDa indicating that the enzyme was highly glycosylated.

N-terminal amino acid sequencing of the 150 kDa component was carried out following SDS-PAGE and elctroblotting onto a PVDF membrane.

Two N-terminal sequences could be deduced in the relative amounts of approximately 4:1 (upper sequence:lower sequence):

Val-Gln-Pro-Phe-Phe-Pro-Pro-Gln-Ile-Gln-Asp-Ser-Trp-Ala-Ala-Tyr-Thr-Pro-Tyr-Tyr-Pro-Val-Gln-
and
Thr-Phe-Val-Gln-Pro-Phe-Phe-Pro-Pro-Gln-Ile-Gln-Asp-Ser-Trp-Ala-Ala-Tyr-Thr-Pro-Tyr-Tyr-Pro- The two N-terminal amino acids "Val" and "Thr" are found in position 27 and 25, respectively, in SEQ ID NO 22. This indicates that the mature phytase enzyme of the invention, when expressed in yeast, starts at position 27 or 25 in SEQ ID No 22.

Accordingly the mature amino acid sequence of the phytase when expressed in yeast is supposed to be no. 27–453 or 25–453 of SEQ ID no 22.

Example 14

Purification and Characterization of the Phytase From *Agrocybe pediades* Expressed in *Aspergillus oryzae*

The *Agrocybe pediades* phytase was expressed in and excreted from *Aspergillus oryzae* IFO 4177.

Filter aid was added to the culture broth which was filtered through a filtration cloth. This solution was further filtered through a Seitz depth filter plate resulting in a clear solution. The filtrate was concentrated by ultrafiltration on 3 kDa cut-off polyethersulphone membranes followed by diafiltration with distilled water to reduce the conductivity. The pH of the concentrated enzyme was adjusted to pH 7.5.

The phytase was applied to a Q-sepharose FF column equilibrated in 20 mM Tris/$CH_3COOH$, pH 7.5 and the enzyme was eluted with an increasing linear NaCl gradient (0→0.5M). The phytase activity eluted as a single peak. This peak was pooled and $(NH_4)_2SO_4$ was added to 1.3M final concentration. A Phenyl Toyopearl 650S column was equilibrated in 1.3M $(NH_4)_2SO_4$, 10 mM succinic acid/NaOH, pH 6.0 and the phytase was applied to this column and eluted with a decreasing linear $(NH_4)_2SO_4$ gradient (1.3→0M). Phytase containing fractions were pooled and the buffer was exchanged for 20 mM Tris/$CH_3COOH$, pH 7.5 by dialysis. The phytase was applied to a SOURCE 30Q column equilibrated in 20 mM Tris/$CH_3COOH$, pH 7.5 and the enzyme was eluted with an increasing linear NaCl gradient (0→0.25M). The phytase activity was pooled and $(NH_4)_2SO_4$ was added to 1.6M final concentration. A SOURCE Phenyl column was equilibrated in 1.6M $(NH_4)_2SO_4$, 25 mM succinic acid/NaOH, pH 6.0 and the phytase was applied to this column and eluted with a decreasing linear $(NH_4)_2SO_4$ gradient (1.6→0M). Fractions from the SOURCE Phenyl column were analyzed by SDS-PAGE and pure phytase fractions were pooled. The phytase pool was dialysed against 20 mM Tris/$CH_3COOH$, pH 7.5, applied to a HighTrap Q column equilibrated in the same buffer, and stepeluted with 20 mM Tris/$CH_3COOH$, 0.5M NaCl, pH 7.5.

The Agrocybe phytase migrates on SDS-PAGE as a band with Mr=60 kDa.

N-terminal amino acid sequencing of the 60 kDa component was carried out following SDS-PAGE and electroblotting onto a PVDF-membrane. Two N-terminal amino acid sequences could be deduced in relative amounts of approximately 2:1 (upper sequence:lower sequence).

Phe-Pro-Pro-Gln-Ile-Gln-Asp-Ser-Trp-Ala-Ala-Tyr-Thr-Pro-Tyr-Tyr-Pro-Val -Gln-
and
Gln-Pro-Phe-Phe-Pro-Pro-Gln-Ile-Gln-Asp-Ser-Trp-Ala-Ala-Tyr-Thr-Pro-Tyr-Tyr- The upper sequence corresponds to amino acid residues 31–49 in the cDNA derived amino acid sequence while the lower sequence corresponds to amino acid residues 28–46.

Accordingly the mature amino acid sequence of the phytase when expressed in Aspergillus is supposed to be no. 31–453 or 28–453 of SEQ ID no 22.

Accordingly, summing up the results of example 13 and the present example, in SEQ ID NO 21, the following sequences are phytase encoding sub-sequences: position 79 to 1362, 73–1362, 91–1362 or 82–1362 (i.e. corresponding to amino acid positions 27–453, 25–453, 31–453 or 28–453, respectively, in SEQ ID NO 22).

Accordingly, there is a slight variability in the N-terminal sequence of the mature phytase enzyme. This variability is observed as well when the enzyme is expressed in a single strain, as when expressed in different strains. In yeast, the mature phytase enzyme starts at amino acid no. 27 or 25 (relative abundance about 80%:20%, respectively); in Aspergillus the mature phytase enzyme starts at amino acid no. 31 or 28 (relative abundance: about 65%:35%, respectively).

Example 15

Characterization of the Purified Phytase of *Agrocybe pediades*

The phytase of *Agrocybe pediades* was expressed in Aspergillus and purified as described in Example 14.

The phytase activity is measured using the following assay:

10 µl diluted enzyme samples (diluted in 0.1 M sodium acetate, 0.01% Tween20, pH 5.5) were added into 250 µl 5 mM sodium phytate (Sigma) in 0.1 M sodium acetate, 0.01% Tween20, pH 5.5 (pH adjusted after dissolving the sodium phytate; the substrate was preheated) and incubated for 30 minutes at 37° C. The reaction was stopped by adding 250 µl 10% TCA and free phosphate was measured by adding 500 µl 7.3 g $FeSO_4$ in 100 ml molybdate reagent (2.5 g $(NH_4)_6Mo_7O_{24}\cdot4H_2O$ in 8 ml $H_2SO_4$ diluted to 250 ml). The absorbance at 750 nm was measured on 200 µl samples in 96 well microtiter plates. Substrate and enzyme blanks were included. A phosphate standard curve was also included (0–2 mM phosphate). 1 FYT equals the amount of enzyme that releases 1 µmol phosphate/min at the given conditions.

Temperature profiles were obtained by running the assay at various temperatures (preheating the substrate).

Temperature stability was investigated by preincubating the phytases in 0.1 M sodium phosphate, pH 5.5 at various temperatures before measuring the residual activity.

The pH-stability was measured by incubating the enzyme at pH 3 (25 mM glycine-HCl), pH 4–5 (25 mM sodium acetate), pH 6 (25 mM MES), pH 7–9 (25 mM Tris-HCl) for 1 hour at 40° C., before measuring the residual activity.

The pH-profiles were obtained by running the assay at the various pH using the same buffer-systems (50 mM, pH was re-adjusted when dissolving the substrate).

The results of the above pH-profile, pH-stability, temperature-profile and temperature stability studies are shown in FIGS. 23, 24, 25 and 26, respectively.

Figure 23:
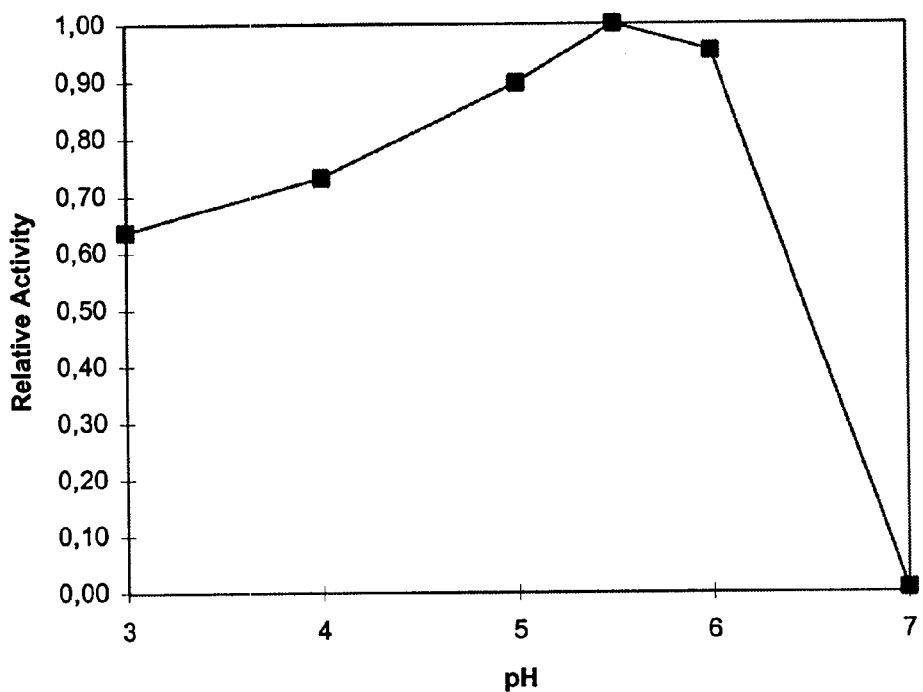
FIG. 23 is a pH-activity curve of the Agrocybe phytase.

From FIG. 23 it appears that the phytase of *Agrocybe pediades* has a reasonable activity at pH 3–6 (i.e. more than 50% of the maximum activity). At pH 4–6 more than 70% of the maximum activity is found, at pH 5–6 more than 90%. Optimum pH seems to be in the area of pH 5.5–6.

Figure 24:
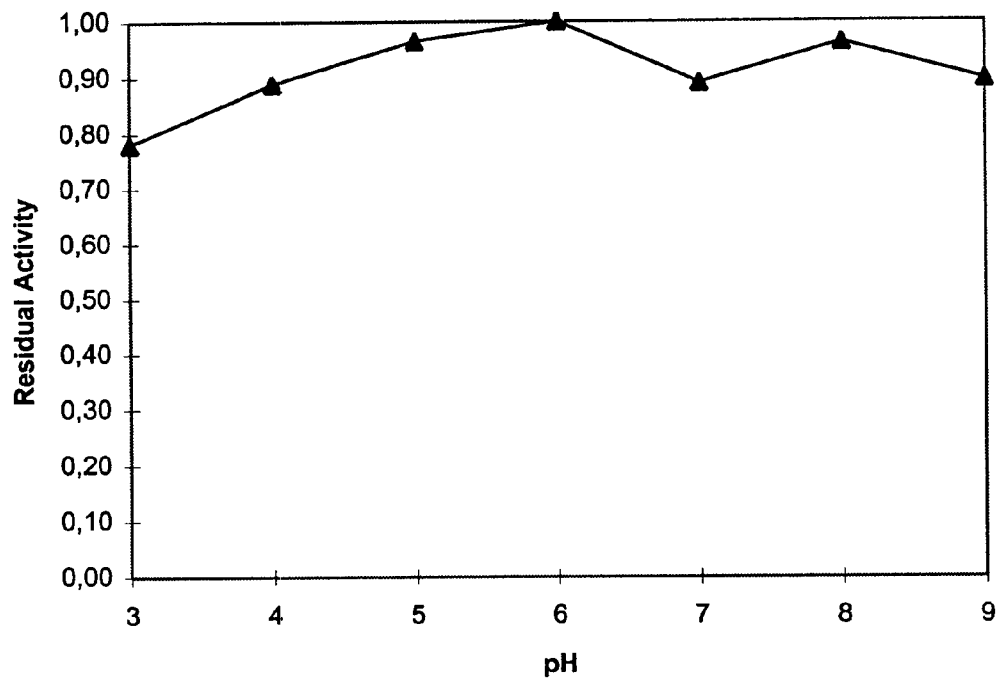
FIG. 24 a pH-stability curve thereof.

It is apparent from FIG. 24 that the phytase of *Agrocybe pediades* is very stable (i.e. more than 80% of the maximum activity retained) for 1 hour at 40° C. in the whole range of pH 3–9.

Figure 25:
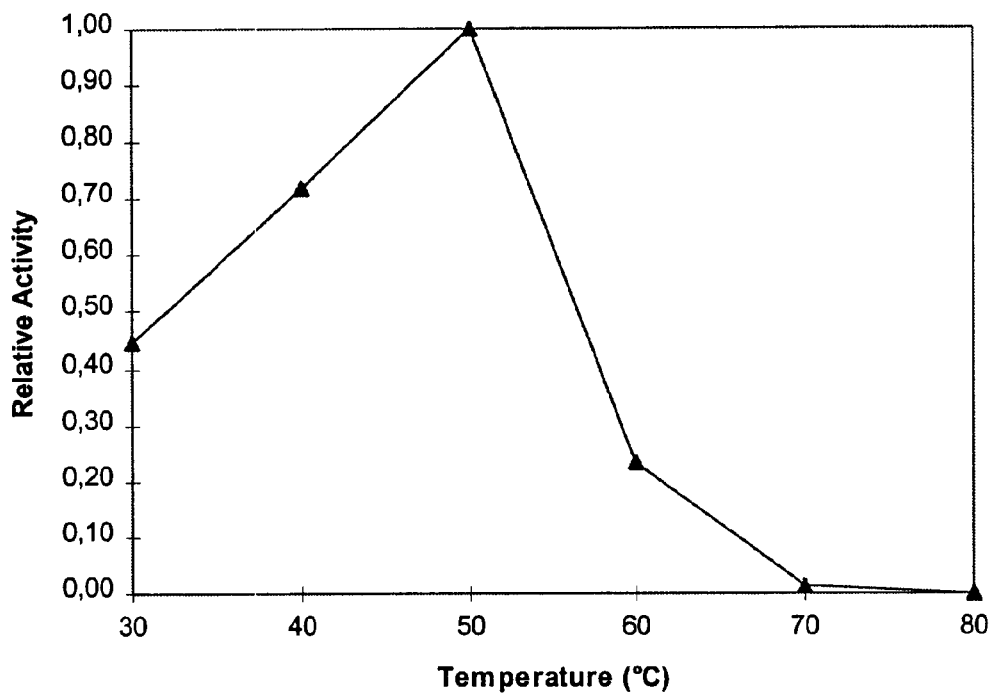
FIG. 25 a temperature-activity curve thereof.

As regards the temperature profile, it is apparent from FIG. 25, that the *Agrocybe pediades* phytase has a reasonable activity at temperatures of 35–55° C. (i.e. more than 60% of the maximum activity), whereas at temperatures of 40–52° C. the activity is more than 70% of the maximum activity, and the optimum temperature is close to 50° C.

Figure 26:
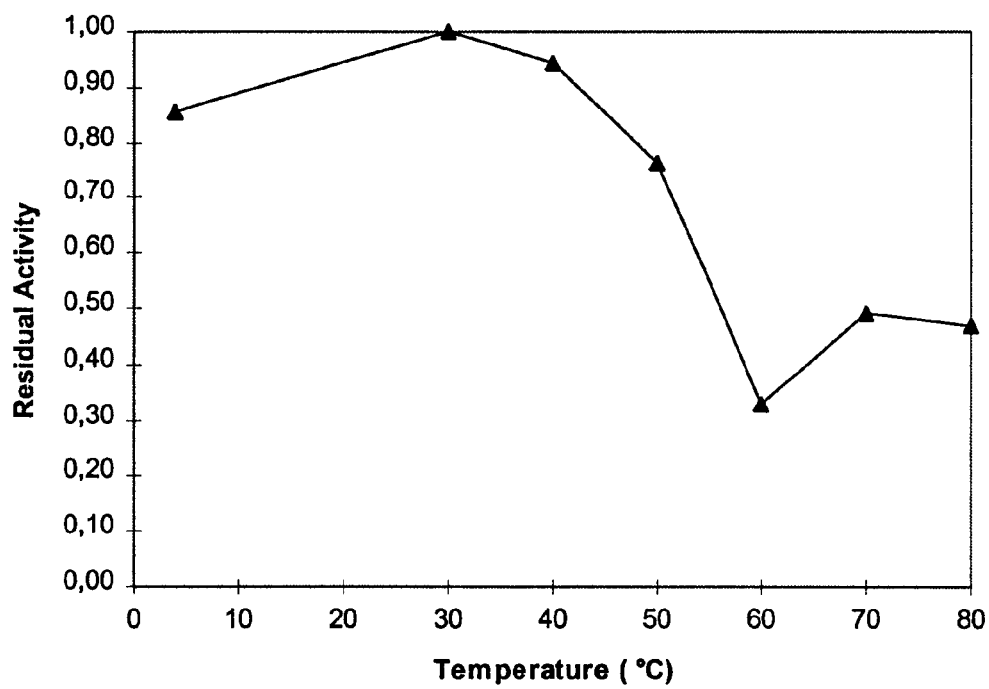
FIG. 26 a temperature-stability curve thereof.

And finally, as regards the temperature stability results shown at FIG. 26, the phytase is very stable at temperatures of 0 to about 55° C. (i.e. more than 60% residual activity). A sharp decline in residual activity is seen after preincubation at 60° C. Anyhow, at 60° C. at least 20%, preferably 25% and more preferably 30% of the residual activity still remains. Also at pre-incubation temperature above 60° C., e.g. at 70° C. and 80° C., a surprisingly high residual activity remains, viz. more than 20%, preferably more than 30%, especially more than 40% remains.

This fact is contemplated to be due to the enzyme being surprisingly capable of refolding following its thermal denaturation. The degree of refolding will depend on the exact conditions (pH, enzyme concentration).

Figure 27:
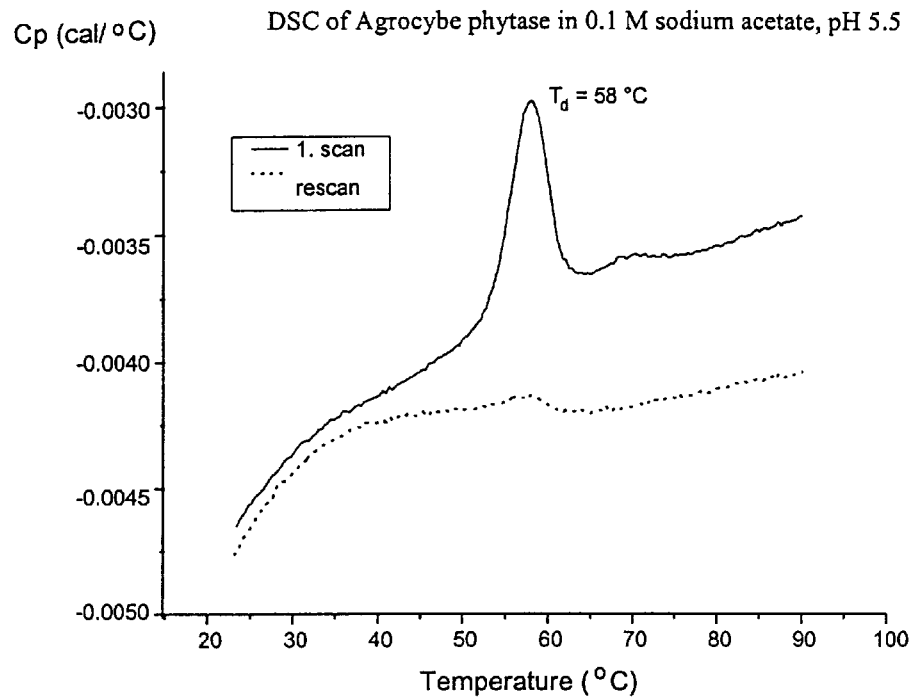
FIG. 27 a Differential Scanning Calorimetry (DSC) curve thereof.

FIG. 27 shows the result of differential scanning calorimetry (DSC) measurements on the Agrocybe phytase.

In DSC the heat consumed to keep a constant temperature increase in the sample-cell is measured relative to a reference cell. A constant heating rate is kept (e.g. 90° C./hour). An endothermal process (heat consuming process—e.g. the unfolding of an enzyme/protein) is observed as an increase in the heat transferred to the cell in order to keep the constant temperature increase.

DSC was performed using the MC2-apparatus from MicroCal. Cells were equilibrated 20 minutes at 20° C. before scanning to 90° C. at a scan rate of 90°/h. Samples of around 2.5 mg/ml Agrocybe phytase in 0.1 M sodium acetate, pH 5.5 were loaded.

The temperature stability studies were confirmed by DSC, since from FIG. 5 it is apparent that the Agrocybe phytase has a denaturation or "melting" temperature of about 58° C. at pH 5.5. The re-scan of the Agrocybe phytase shows a minor peak at 58° C., and this is also indicative of the fact that a fraction of the enzyme is actually refolded folding the thermal inactivation in the first scan.

Example 16

Time-Resolved Product-Profiling of Phytase-Catalyzed Hydrolysis of Phytic Acid by $^1$H NMR Spectroscopy The hydrolysis of phytic acid (PA) catalyzed by the Agrocybe phytase and by a commercial *Aspergillus niger* phytase (Phytase Novo®) was investigated (27 mM phytate, 1 FYT/ml, pH 5.5, and 27° C.) by $^1$H NMR profiling the product mixture in the course of 24 hours.

In the following (Ins(p,q,r, . . . )$P_n$ denotes myo-inositol carrying in total n phosphate groups attached to positions p, q, r, . . . For convenience Ins(1,2,3,4,5,6)$P_6$ (phytic acid) is abbreviated PA. Please refer, however, to the section "Nomenclature and position specificity of phytases" in the general part of this application.

The technique provide specific information about initial points of attack by the enzyme on the PA molecule, as well as information about the identity of the end product. On the other side the evolving patterns of peaks reflecting the composition of the intermediate product mixtures, provide a qualitative measure, a finger print, suitable for identification of similarities and differences between individual enzymes.

NMR, like most other analytical methods, can distinguish between stereo-isomers which are not mirror images (diastereomers), but not between a set of isomers, which are mirror-images (enantiomers), since they exhibit identical NMR spectra.

Thus, Ins(1,2,4,5,6)$P_5$ (3-phosphate removed) exhibits a NMR spectrum different from Ins(1,2,3,4,5)$P_5$ (6-phosphate removed) because the isomers are diastereomers.

However, the NMR spectra of Ins(1,2,4,5,6)$P_5$ and Ins(2,3,4,5,6)$P_5$ (1-phosphate removed) are identical because the isomers are enantiomers. The same holds for the pair Ins(1,2,3,4,5)$P_5$ and Ins(1,2,3,5,6)$P_5$ (4-phosphate removed).

Thus, by NMR it is not possible to distinguish between a 3- and a 1-phytase, and it is not possible to distinguish between a 6- and a 4-phytase (or a L-6- and a D-6-phytase using the lowest-locant rule).

Biased by the description of 3- and 6-phytases in the literature, we have used the terms 3- and 6-phytases for our enzymes, but, though unlikely, we do not actually know if we have a 1- and a 4-phytase instead.

Experimental

NMR spectra were recorded at 300 K (27° C.) on a Bruker DRX400 instrument equipped with a 5 mm selective inverse probe head. 16 scans preceded by 4 dummy scans were accumulated using a sweep width of 2003 Hz (5 ppm) covered by 8K data points. Attenuation of the residual HOD resonance was achieved by a 3 seconds presaturation period. The spectra were referenced to the HOD signal (δ 4.70).

PA samples for NMR analysis were prepared as follows: PA (100 mg, Phytic acid dipotassium salt, Sigma P-5681) was dissolved in deionized water (4.0 ml) and pH adjusted to 5.5 by addition of aqueous NaOH (4 N). Deionized water was added (ad 5 ml) and 1 ml portions, each corresponding to 20 mg of phytic acid, were transferred to screw-cap vials and the solvent evaporated (vacuum centrifuge). The dry samples were dissolved in deuterium oxide (2 ml, Merck 99.5% D) and again evaporated to dryness (stored at −18° C. until use).

For NMR analysis one 20 mg phytic acid sample was dissolved in deuterium oxide (1.0 ml, Merck 99.95% D). The solution was transferred to a NMR tube and the $^1$H NMR spectrum recorded. Enzyme solution (1 FTU, dissolved in/diluted, as appropriate, with deuterium oxide) was added followed by thorough mixing (1 minute). $^1$H NMR spectra were recorded immediately after addition of enzyme (t=0), then after 5, 10, 15, 20, 25, 30, 45, 60, 75, 90, 105, 120, 135 150, 165, 180, 195, 210 minutes (=3.5 hours), 4.5, 5.5 6.5, 7.5, 8.5, 9.5, 11.5, 13.5, 15.5, 17.5, 19.5, 21.5, and 23.5 hours. The pH in the NMR tube was measured. Additional spectra were acquired after 48 and 120 hours (5 days), where a portion of substrate (PA, 6 mg) was added to probe if the enzyme retained its catalytic activity.

By means of 2D NMR analysis of inositol phosphate mixtures obtained by partial digestion of PA, in conjunction with published NMR data (Scholz, P.; Bergmann, G., and Mayr, G. W.: Methods in Inositide Research (Ed. Irvine, R. F.), pp. 65–82, Raven Press, Ltd., New York (1990)), characteristic $^1$H NMR signals attributable to Ins(1,2,3,4,5,6)P$_6$ (PA), Ins(1,2,4,5,6)P$_5$, Ins(1,2,3,4,5)P$_5$, Ins(1,2,5,6)P$_4$, Ins (1,2,6)P$_3$, Ins(1,2)P$_2$, and Ins(2)P, were identified and permitted relative quantification of these species during the course of the reaction.

Figure 28:
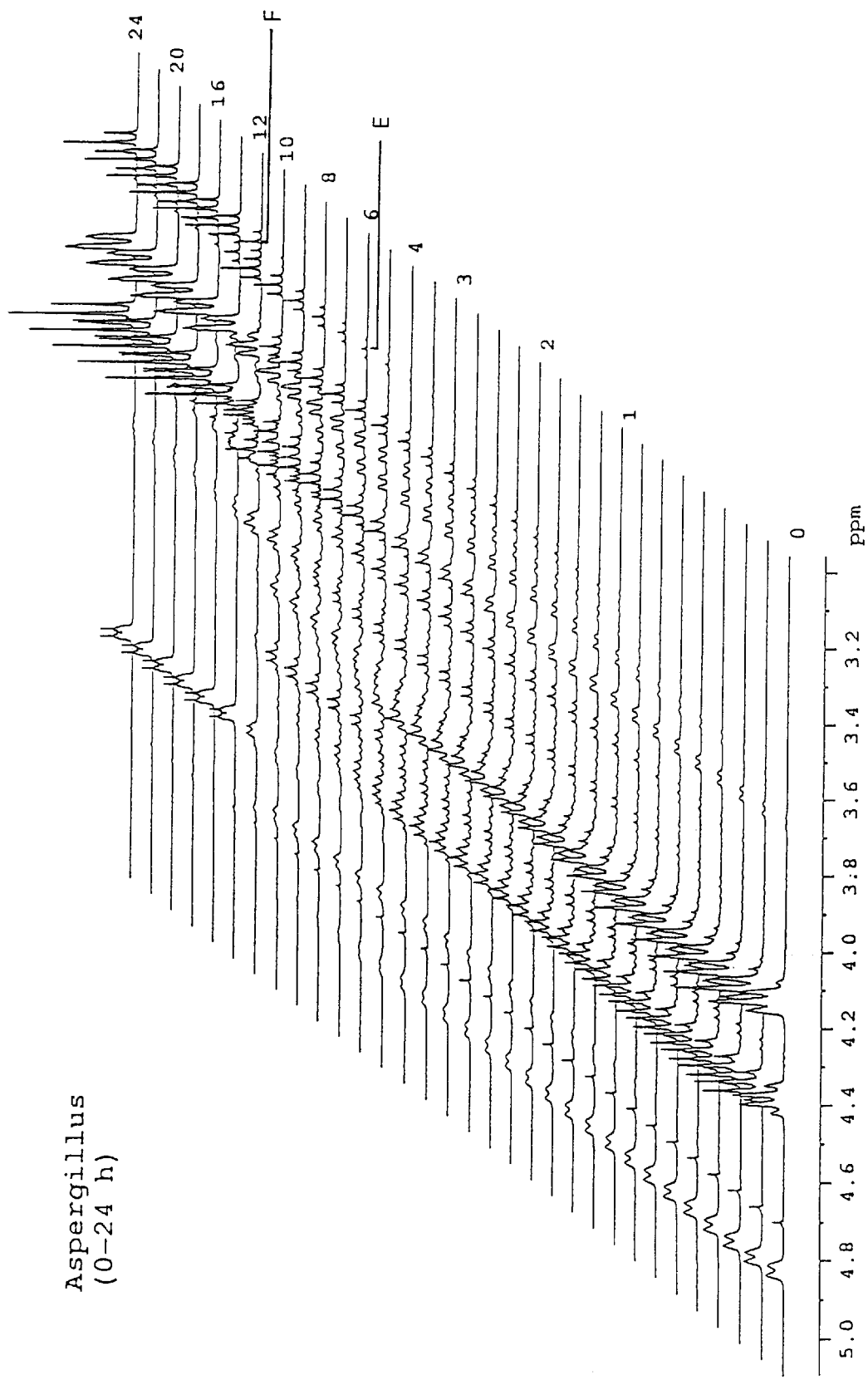
FIGS. 28–29 NMR spectra, stacked plots (up to 24 h), showing the product profiling of an *Aspergillus niger* and the Agrocybe phytase, respectively.
Figure 29:
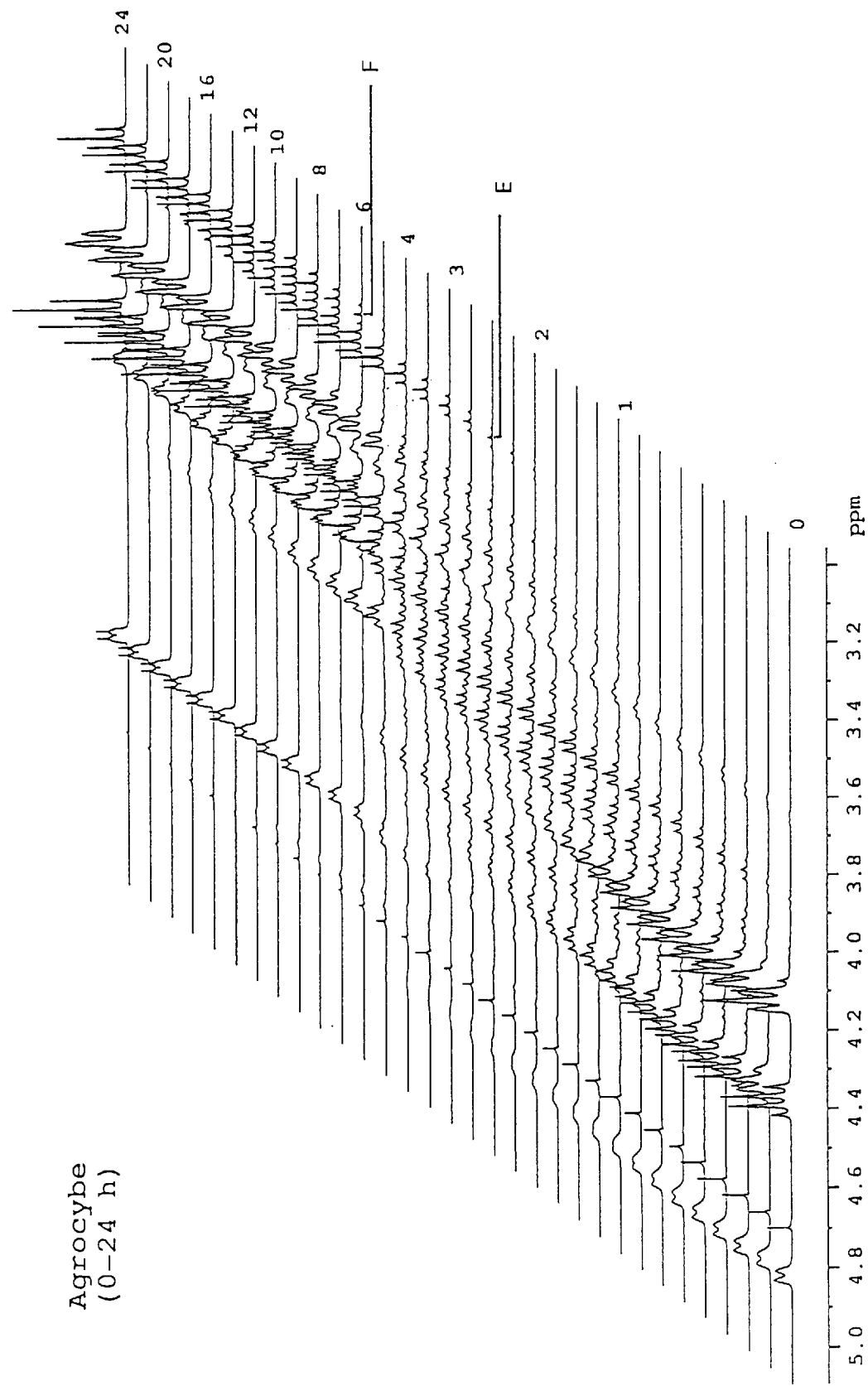

Stacked plots of product profiles for the Aspergillus phytase and the Agrocybe phytase covering 24 hours of reaction time is presented in FIG. 28 and FIG. 29, respectively.

The signal at δ 3.25(t) represents H-5 in Ins(1,2)P$_2$ whereas the signal at δ 3.18(t) represents H-5 in Ins(2)P. Ins(1,2)P$_2$ starts accumulating after about 4 hours of reaction time with the Aspergillus phytase and after about 2 hours of reaction time with the Agrocybe phytase. Ins(2)P is observed after about 10 hours of reaction with the Aspergillus phytase and after about 5 hours of reaction with the Agrocybe phytase. After 24 hours of reaction the amount or level of Ins(1,2)P$_2$ is very low for both phytases, whereas the amount of Ins(2)P is maximum for both phytases after 24 hours.

Accordingly, the profiles observed after 24 hours of reaction time demonstrate that both phytases degrade PA to Ins(2)P. The fully dephosphorylated species, inositol (Ins), was not observed at all.

For both enzymes the reaction mixture at 24 h comprised in addition to Ins(2)P minor amounts of Ins(1,2)P$_2$ Prolonged reaction times (several days) resulted in disappearance of the residual Ins(1,2)P$_2$, but the fully dephosphorylated species, inositol (Ins), was not observed at all. The observation is not explained by irreversible inhibition/denaturation of the enzyme, since the enzymes retained their catalytic activities for prolonged periods, as demonstrated by their ability to digest fresh portions of PA added to the NMR tubes after keeping them 5 days at room temperature.

Figure 30:
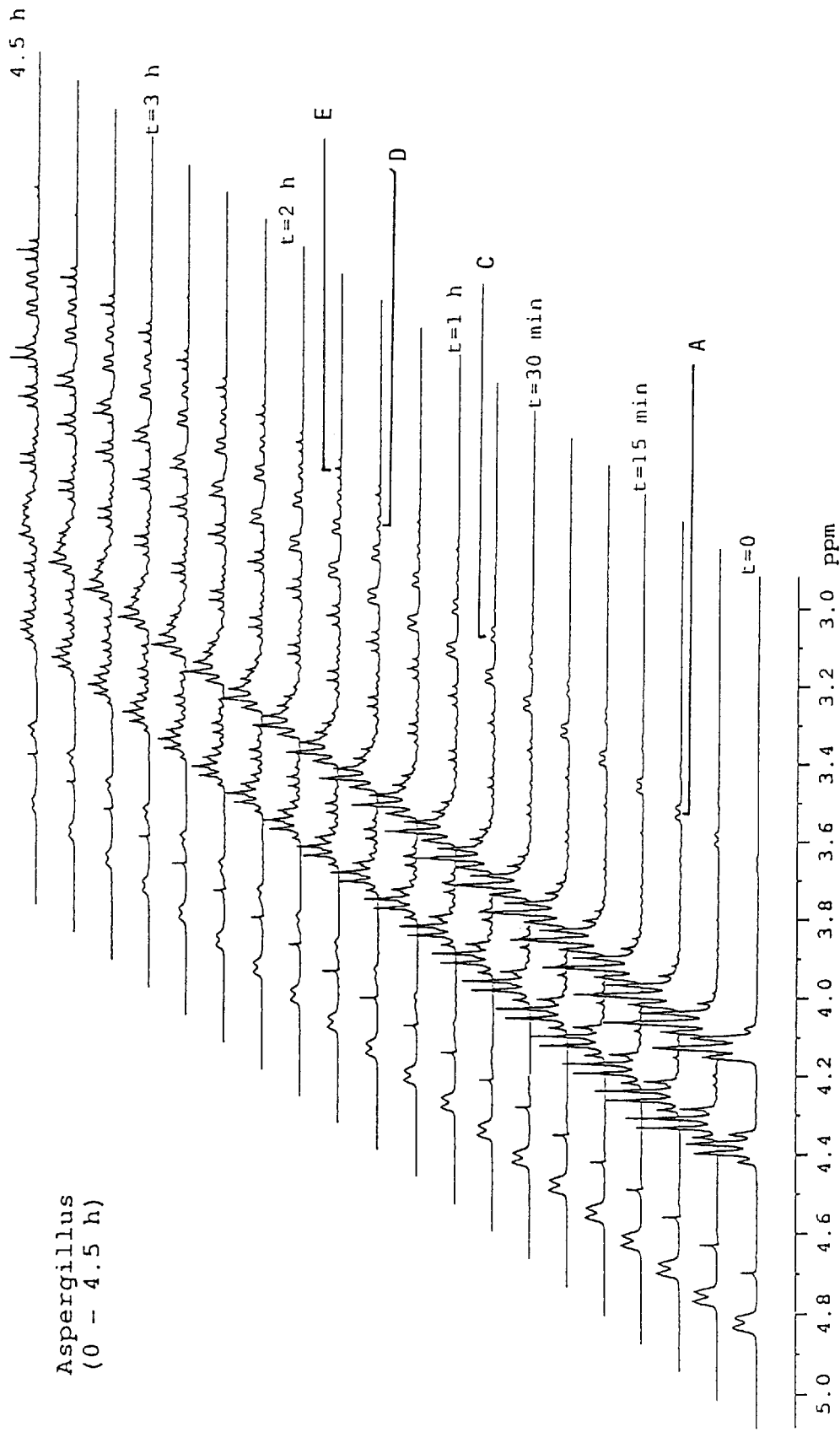
FIGS. 30–31 NMR spectra as above, but stacked plots up to 4.5 h.
Figure 31:
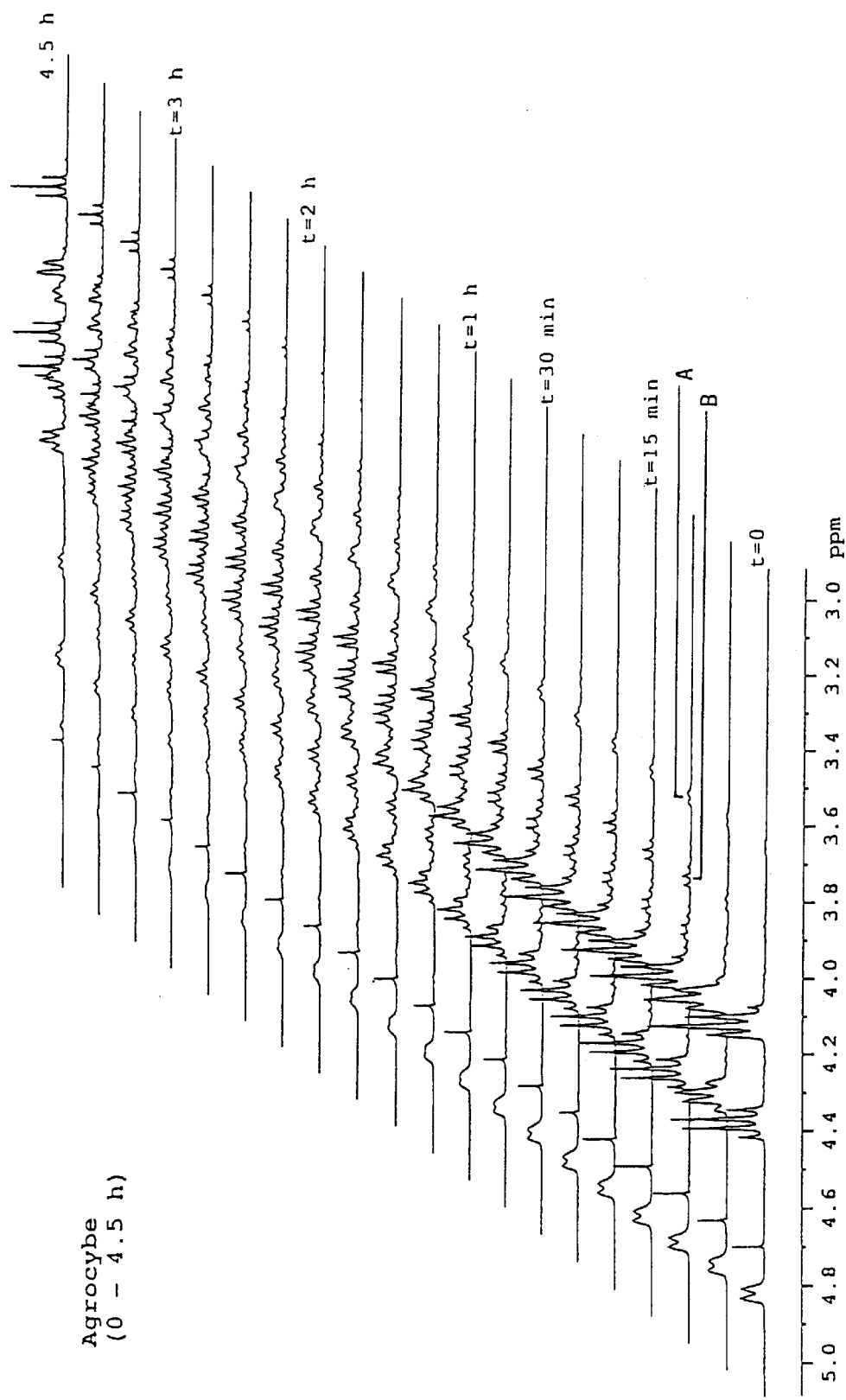

Turning now to FIGS. 30 and 31, these depict in more detail the profiles evolving during the initial 4.5 hours. It is inferred from FIG. 32 that H-3 in Ins(1,2,4,5,6)P$_5$ (designated A) shows a signal at δ 3.66(dd), H-6 in Ins(1, 2,3,4,5)P$_5$ (B) a signal at δ 3.87(t) and H-3 in Ins(1,2,5,6)P$_4$ (C) a signal at δ 3.56(dd). Now, compound A corresponds to phosphate in position 3 having been hydrolyzed, B position 6 and C position 3 and 4.

It is apparent from FIG. 30 that compound A appears as the major primary product (t=5 min) using the Aspergillus phytase, whereas compound B does not appear. Compound C appears after 20–25 minutes.

From FIG. 31 (the Agrocybe phytase) one infers that compound A as well as compound B appear very early, i.e. within the first 15 minutes, probably more of the compound B than A.

The signals at δ 4.82(dt, H-2), 4.38 (q, H-4/H-6), 4.13(q, H-5) and 4.11(dt,H1/H3) are attributable to the substrate, phytic acid, PA. Comparing FIGS. 30 and 31 it is apparent, that these peaks diminish much faster (i.e. within an hour) with the Agrocybe phytase than with the Aspergillus phytase.

Figure 32:
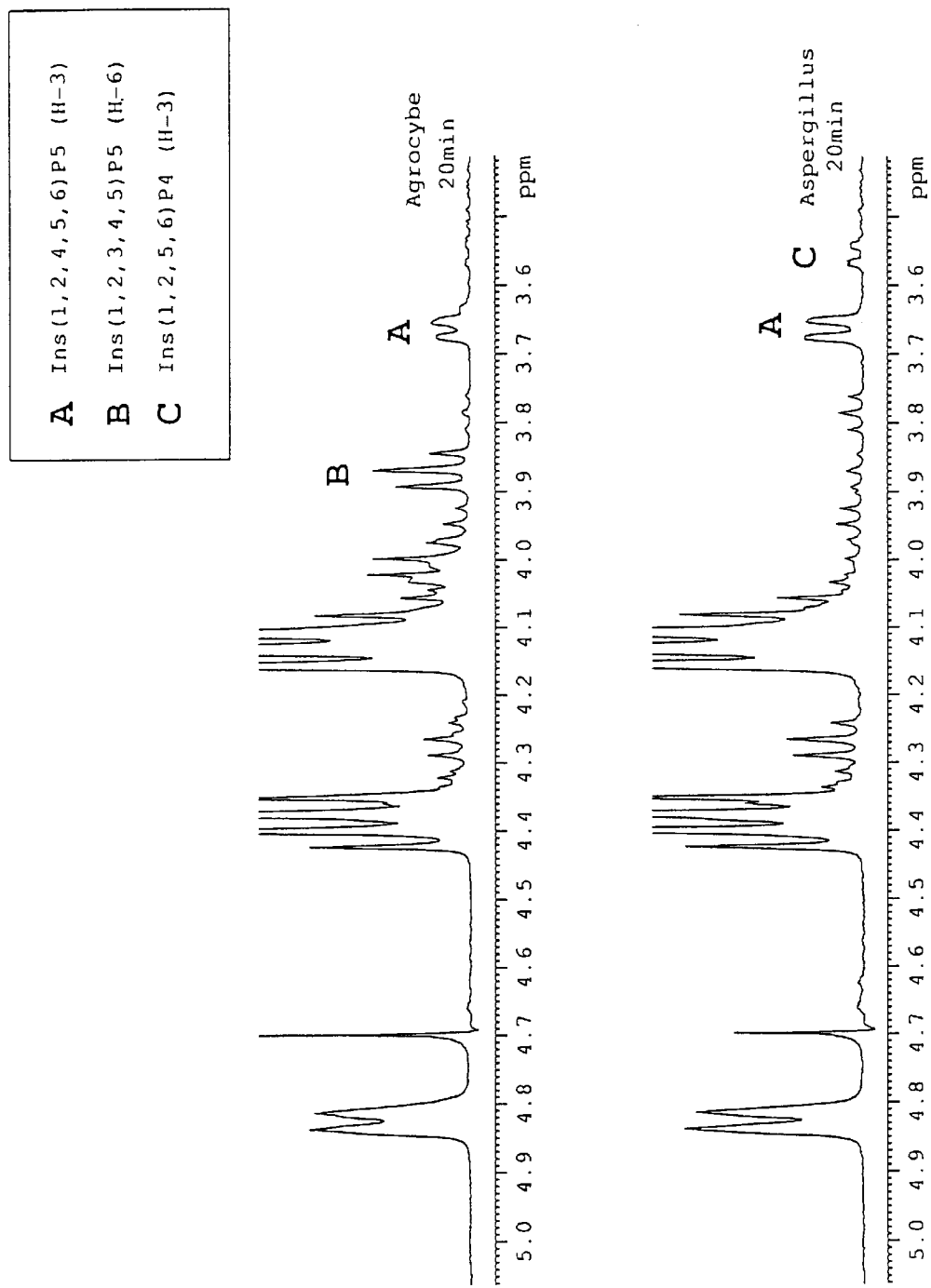
FIGS. 32–33 NMR profiles observed after 20 minutes and 24 hours, respectively.

These differences are highlighted in FIG. 32, which present the profiles observed after 20 min with the above indicated diagnostic signals (A,B,C) labelled.

Figure 33:
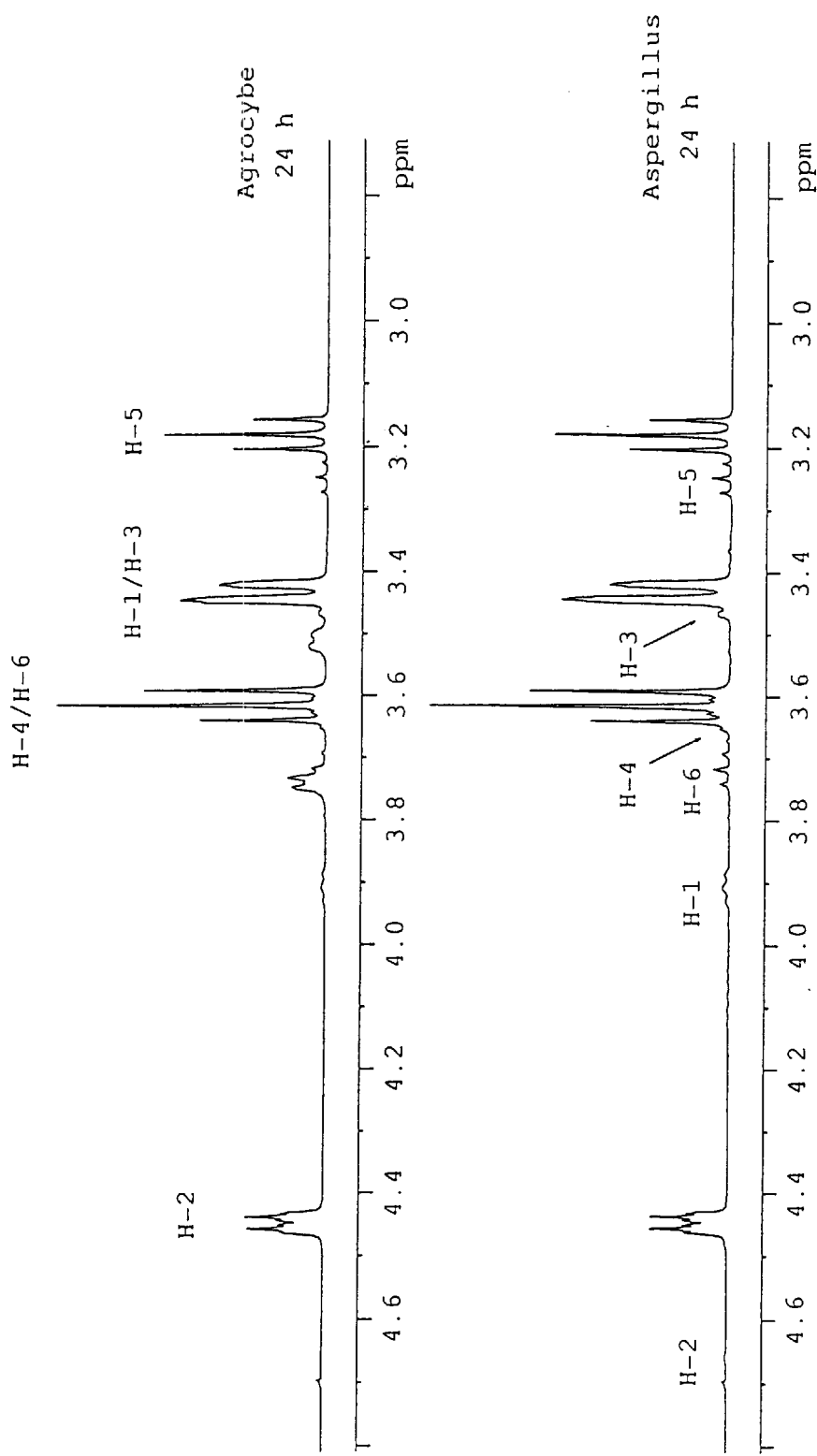

FIG. 33 shows the final result (under these conditions) of the hydrolysis of phytic acid (i.e. corresponding to the upper line of FIGS. 28 and 29). All signals labelled at the upper Agrocybe embodiment represent the compound Ins(2)P, viz. the protons thereof, from the right to the left: H-5, H1 and H3, H4 and H6 and finally H-2. Relative intensity: 1:2:2:1.

The corresponding signals are found in the bottom embodiment of Aspergillus. This means that the end product is in both embodiments Ins(2)P. However, a minor amount of Ins(1,2)P$_2$ is also detected in both embodiments, the corresponding peaks being indicated at the Aspergillus embodiment only.

Figure 34:
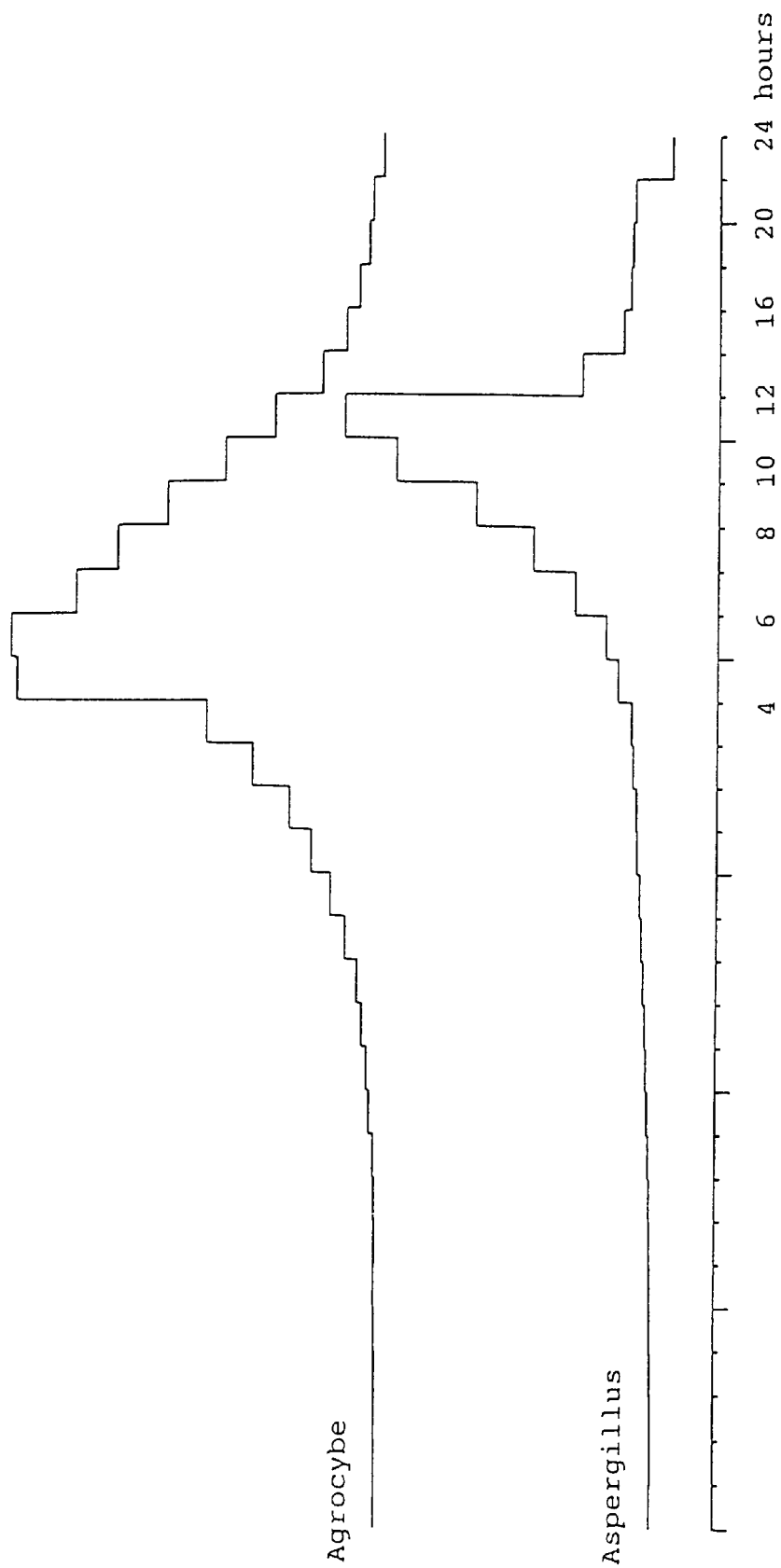
FIGS. 34–35 curves showing concentration versus time of Ins(1,2)P2 and Ins(2)P, respectively.
Figure 35:
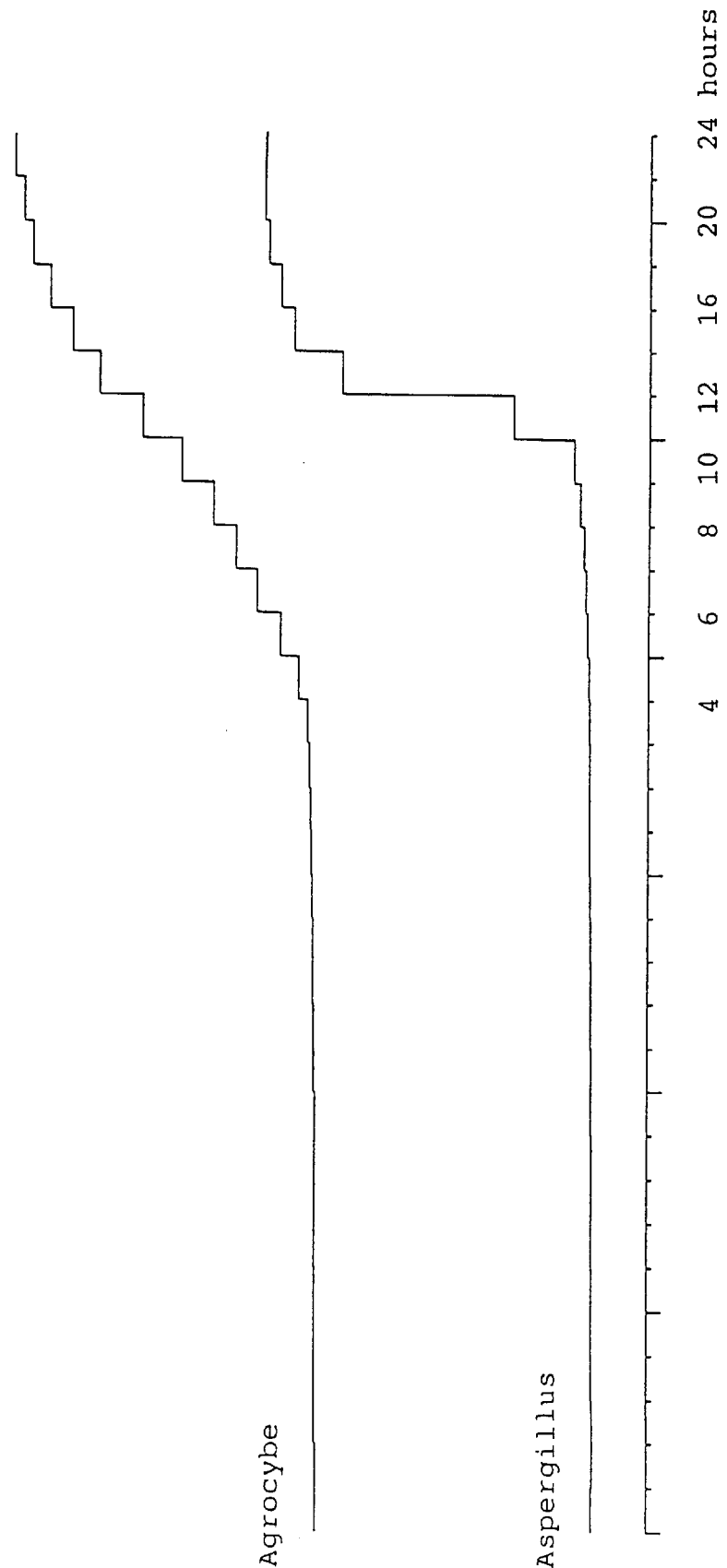

Marked differences are observed:

Aspergillus: The initial major product was identified as Ins(1,2,4,5,6)P$_5$ (A) followed by appearance of Ins(1,2,5,6) P$_4$ (C), and Ins(1,2,6)P$_3$ (D) (H-3 at δ 3.49(dd) after 1½ hours) corresponding to consecutive removal of the phosphate groups in the 3-, 4- and 5-positions. The concentration of Ins(1,2)P$_2$ (E) builds up slowly starting at 2 hours and decreases very steeply between 12 and 14 hours with a concomitant rapid increase of the Ins(2)P (F) level. This is visualized in FIG. 34 and 35, representing the time dependent concentration of Ins(1,2)P$_2$ and Ins(2)P, respectively, constructed from slices along the time-dimension in FIGS. 28–29 at the chemical shift values (δ) of H-5 in Ins(1,2)P$_2$ and Ins(2)P, respectively (note that the time scale is only linear in segments).

Agrocybe: Both the 3- and 6-positions are initially attacked, with some preference for the 6-position. A characteristic feature is that PA is digested at a faster rate compared to the Aspergillus phytase. Additional characteristic features are that the end product, Ins(2)P (F) appear very early (5 hours) and builds up slowly, in contrast to the very steep increase in the Ins(2)P-level towards the end of the reaction observed for the Aspergillus phytase.

The data generated permit i.a. the following conclusions:

The Aspergillus phytase attacks with a high degree of selectivity PA in the 3-position, whereas the Agrocybe phytase appear less specific.

The Agrocybe phytase digests PA at a faster rate compared to the Aspergillus phytase.

The end-product is in both cases, under the conditions applied, Ins(2)P (F).

The overall reaction rates (PA→Ins(2)P) were comparable, approximately 20 hours (FIG. 35).

Accordingly, the Aspergillus phytase prove to be an essentially clean 3-phytase, whereas the Agrocybe phytase appear to be less specific, however, with some preference for the 6-position.

By application of 2D-homo- and heteronuclear ($^1$H,$^{13}$C) correlation techniques, the latter circumventing problems with severely overlapping $^1$H-resonances by taking advantage of the larger chemical shift dispersion of the $^{13}$C-nuclei, in combination with suitable computer software, it would in principle be possible to identify and quantify intermediates present at any given time and thereby completely map out the reaction sequence. In other words, curves like those shown in FIGS. 34 and 35 representing concentration as a function of time, could in theory be constructed for other intermediate inositol phosphates.

Example 17

Comparative Assay, Aspergillus and Agrocybe Phytase Release of Inorganic Phosphate From Corn The present example gives a simple assay for the phytase catalyzed liberation of phosphorous from corn at pH 3.5 and 5.5. Two parameters have been focused on—velocity and level of P-liberation.

Materials and Methods

Corn was obtained from North Carolina State University (sample No. R27), and ground at a mill (Bühler Universal) at point 6.8.

A corn-suspension (16.7% w/w) was prepared by weighing 20 g of ground corn into a 250 ml blue cap bottle and adding 100 ml of buffer.

The following buffers were used:

pH 5.5: 0.22 M acetate-buffer pH 3.5: 0.05 M citrate-buffer.

Enzymes tested: Two phytases was tested: A commercial phytase of *Aspergillus niger* (Phytase Novo®) and an Agrocybe phytase of the invention, purified as described in example 3 and 4. Dosage: All enzymes were applied at 25 FYT/20 g corn (correspond to 1250 FYT/kg).

The bottles with the corn suspension were closed by caps, and immediately placed in a water bath at 37° C. and subjected to constant stirring. pH was measured at this stage and again after 24 hours. After 30 min of stirring a sample of 5 ml was collected.

Then the phytase enzymes were added at a dosage of 25 FYT/20 g of corn.

Samples were then collected 10, 20, 30, 40, 50, 60, 120 min, and approx. 20 hours after the addition of the phytases, and the content of release P determined as follows:

Phytase containing samples were diluted 1+4 in buffer. Then the samples were centrifuged at 3000 rpm for 5 min, and 1.0 ml of the supernatant was collected. 2.0 ml buffer and 2.0 ml MoV stop solution (cfr. the FYT assay of Example 15) was added. The samples were placed in a refrigerator at 3–5° C. until all samples could be measured at the spectrophotometer at 415 nm.

pH was measured at time 0 and 20 hours.

For the determinations a phosphate standard or stock solution of 50 mM was used prepared. 0.5, 1.0, 1.5 and 2.0 ml stock solution is diluted to a total volume of 50 ml using buffer. 3.0 ml of each solution is added 2.0 ml MoV stop solution.

Figure 36:
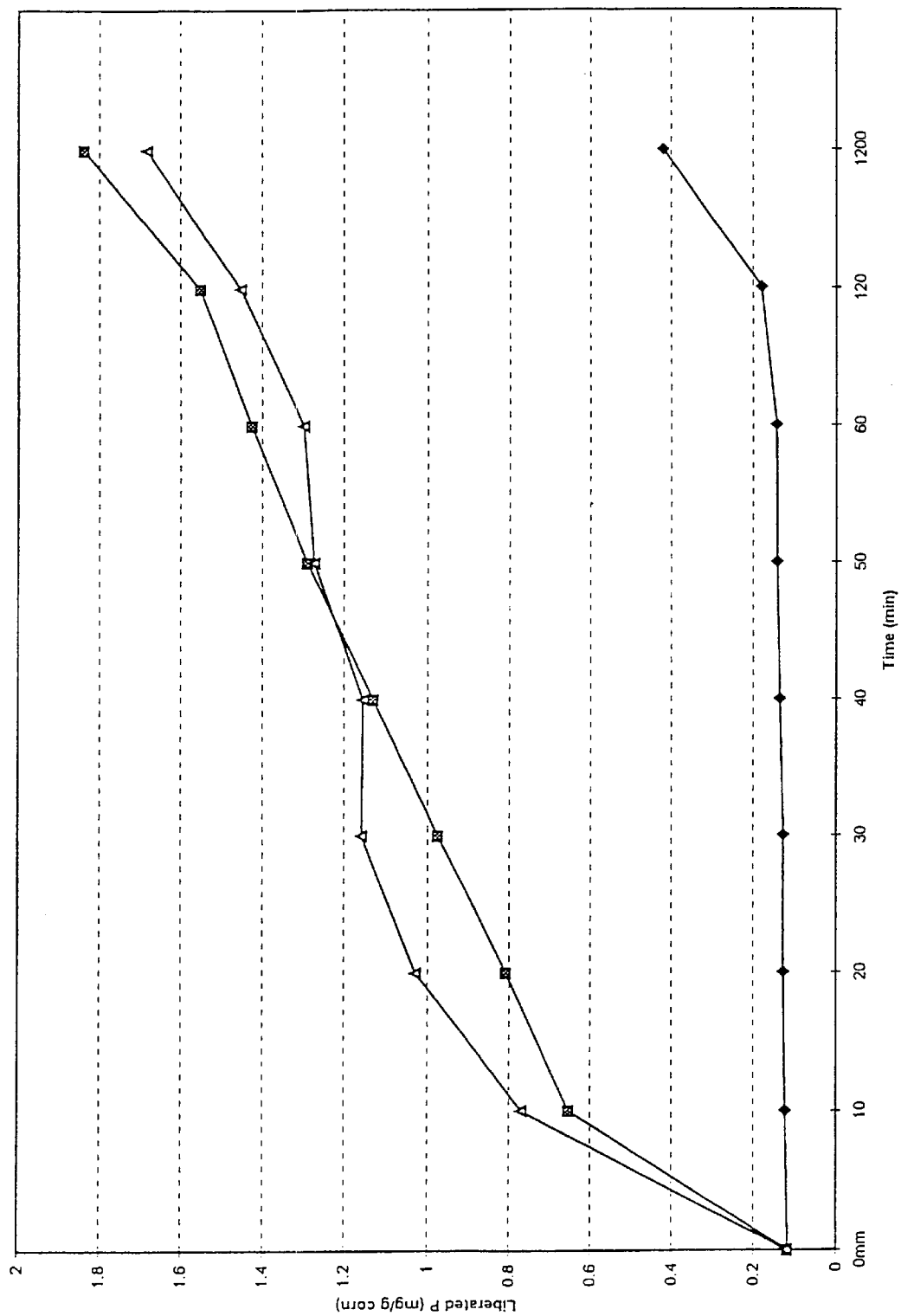
FIGS. 36–37 curves showing the release of inorganic phosphate versus time from corn at pH 5.5 and pH 3.5, respectively.
Figure 37:
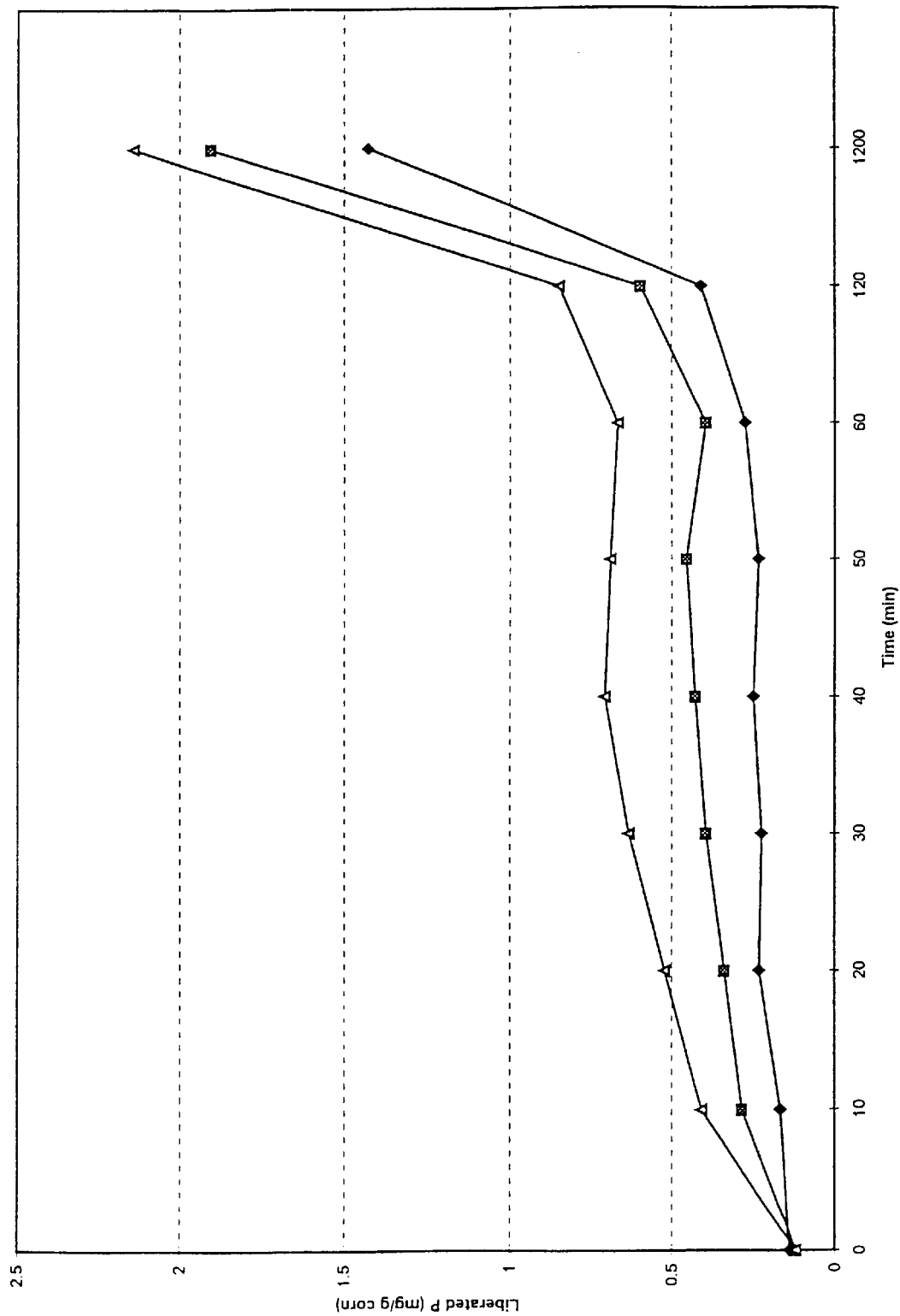
Figure 38:
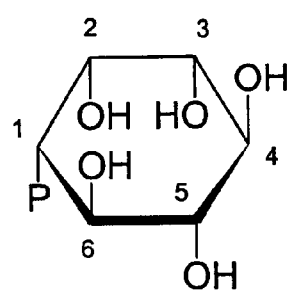
FIG. 38 the structure of 1D- and 1L-myo-inositol-1-phosphate ($P=\!\!-\!\!OPO_3^{-2}$).
Figure 38:
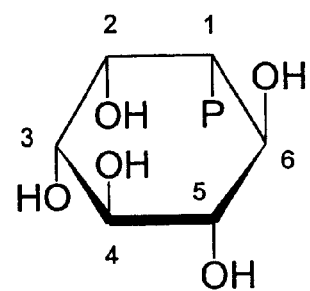

Two experiments were conducted: at pH 5.5 and at pH 3.5. The analysis results are shown at FIGS. 36 and 37 (pH 5.5 and 3.5, respectively). At these figures, symbol "♦" represents the control experiment, "▲" the Agrocybe phytase and "■" the Aspergillus phytase.

Results and Discussion

FIGS. 36 and 37 clearly show that the Agrocybe phytase initially liberates phosphorous from ground corn faster than the Aspergillus phytase at pH 5.5 and at pH 3.5.

However, after 40 min. at pH 5.5 (FIG. 36) and after 120 min. at pH 3.5 (FIG. 37), the Aspergillus phytase is approximately at the same level of released phosphate as is the Agrocybe phytase.

But considering the passage time of the digestive system of for instance chickens/broilers, which normally is of the order of magnitude of 30 minutes to 2 hours, this difference is for sure important. Besides, it should be mentioned, that the pH value of 3.5 is more relevant in this respect than the pH 5.5 value.

This implies that the Agrocybe enzyme is surprisingly more efficient than the known Aspergillus phytase as a P-liberator in the digestive system of e.g. broilers.

Example 18

Purification and Characterization of the Phytases From *Paxillus involtus* and *Trametes pubescens*

The PhyA1 Phytase From *Paxillus involtus*

The *Paxillus involtus* PhyA1 phytase was expressed in and excreted from *Aspergillus oryzae* IFO 4177 as described in Examples 3 and 1.

Filter aid was added to the culture broth which was filtered through a filtration cloth. This solution was further filtered through a Seitz depth filter plate resulting in a clear solution. The filtrate was concentrated by ultrafiltration on 3 kDa cut-off polyethersulphone membranes and the phytase was transferred to 10 mM succinic acid/NaOH, pH 6.0 on a Sephadex G25 column. The pH of the G25 filtrate was adjusted to pH 7.0.

The phytase was applied to a Q-sepharose FF column equilibrated in 20 mM HEPES/NaOH, pH 7.0. The enzyme turned out to be in the run-through from the column. $(NH_4)_2SO_4$ was added to the run-through to 2.0M final concentration. A Butyl Toyopearl 650S column was equilibrated in 2.0M $(NH_4)_2SO_4$, 10 mM $CH_3COOH$/NaOH, pH 5.5 and the phytase was applied to this column and eluted with a decreasing linear $(NH_4)_2SO_4$ gradient (2.0→0M). Phytase containing fractions were pooled and the buffer was exchanged for 20 mM HEPES/NaOH, pH 7.5 on a Sephadex G25 column. The G25 filtrate was applied to a Q-sepharose FF column equilibrated in 20 mM HEPES/NaOH, pH 7.5. After washing the column extensively with the equilibration buffer, the phytase was eluted with an increasing linear NaCl gradient (0→0.5M). The phytase activity was pooled and the buffer was exchanged for 20 mM Tris/$CH_3COOH$, pH 8.0 on a Sephadex G25 column. The G25 filtrate was applied to a SOURCE 30Q column equilibrated in 20 mM Tris/$CH_3COOH$, pH 8.0. After washing the column thoroughly with the equilibration buffer en phytase was eluted with an increasing linear NaCl gradient (0→0.3M). Phytase containing fractions were pooled and $(NH_4)_2SO_4$ was added to 2.0M final concentration. A Phenyl Toyopearl 650S column was equilibrated in 2.0M $(NH_4)_2SO_4$, 10 mM $CH_3COOH$/NaOH, pH 5.5 and the phytase was applied to this column and eluted with a decreasing linear $(NH_4)_2SO_4$ gradient (2.0→0M). Phytase containing fractions were pooled and reapplied to the same Phenyl Toyopearl column after adding $(NH_4)_2SO_4$ to 2.0M final concentration. Fractions from the second Phenyl Toyopearl column were analyzed by SDS-PAGE and pure phytase fractions were pooled.

The *Paxillus involtus* PhyA1 phytase migrates on SDS-PAGE as a band with Mr=65 kDa. N-terminal amino acid sequencing of the 65 kDa component was carried out following SDS-PAGE and electroblotting onto a PVDF-membrane. The following N-terminal amino acid sequence could be deduced.

Ser-Val-Pro-Lys-Asn-Thr-Ala-Pro-Thr-Phe-Pro-Ile-Pro

The sequence corresponds to amino acid residues 21–33 in the cDNA derived amino acid sequence.

Accordingly a mature amino acid sequence of the phytase when expressed in Aspergillus is supposed to be no. 21–442 of SEQ ID no. 26. Accordingly, the predicted signal peptide at FIG. 3 does not correspond with the actual signalpeptide when this phytase is expressed in Aspergillus. This is also so for the indications regarding mature peptide of the sequence listing under the headings SEQ ID NOs: 25 and 26.

The PhyA2 Phytase From *Paxillus involtus*

The *Paxillus involtus* PhyA2 phytase was expressed in and excreted from *Aspergillus oryzae* IFO 4177 as described in Examples 3 and 1.

Filter aid was added to the culture broth which was filtered through a filtration cloth. This solution was further filtered through a Seitz depth filter plate resulting in a clear solution. The filtrate was concentrated by ultrafiltration on 3 kDa cut-off polyethersulphone membranes and $(NH_4)_2SO_4$ was added to 2.0M final concentration.

The phytase was applied to a Phenyl sepharose FF column equilibrated in 2.0M $(NH_4)_2SO_4$, 20 mM $CH_3COOH$/NaOH, pH 5.5 and the enzyme was eluted with a decreasing linear $(NH_4)_2SO_4$ gradient (2.0→0M). The phytase activity eluted as a single peak. This peak was pooled and (NH$_4$)$_2$SO$_4$ was added to 2.0M final concentration. A Butyl Toyopearl 650S column was equilibrated in 2.0M (NH$_4$)$_2$SO$_4$, 10 mM CH$_3$COOH/NaOH, pH 5.5 and the phytase was applied to this column and eluted with a decreasing linear (NH$_4$)$_2$SO$_4$ gradient (2.0→0M). Phytase containing fractions were pooled and the buffer was exchanged for 20 mM HEPES/NaOH, pH 7.0 on a Sephadex G25 column. The G25 filtrate was applied to a Q-sepharose FF column equilibrated in 20 mM HEPES/NaOH, pH 7.0. After washing the column extensively with the equilibration buffer, the phytase was eluted with an increasing linear NaCl gradient (0→0.5M). The phytase activity was pooled and the buffer was exchanged for 20 mM HEPES/NaOH, pH 7.0 by dialysis. The dialysed phytase was applied to a SOURCE 30Q column equilibrated in 20 mM HEPES/NaOH, pH 7.0. After washing the column thoroughly with the equilibration buffer en phytase was eluted with an increasing linear NaCl gradient (0→0.3M). Fractions from the SOURCE 30Q column were analyzed by SDS-PAGE and pure phytase fractions were pooled.

The *Paxillus involtus* PhyA2 phytase migrates on SDS-PAGE as a band with M$_r$=52 kDa. N-terminal amino acid sequencing of the 52 kDa component was carried out following SDS-PAGE and electroblotting onto a PVDF-membrane. The following N-terminal amino acid sequence could be deduced.

Asn-Ile-Ala-Pro-Lys-Phe-

The sequence corresponds to amino acid residues 25–30 in the cDNA derived amino acid sequence.

Accordingly a mature amino acid sequence of the phytase when expressed in Aspergillus is supposed to be no. 25–442 of SEQ ID no. 28. Accordingly, the predicted signal peptide at FIG. 4 does not correspond with the actual signalpeptide when this phytase is expressed in Aspergillus. This is also so for the indications regarding mature peptide of the sequence listing under the headings SEQ ID NOs: 27 and 28.

The Phytase From *Trametes pubescens*

The *Trametes pubescens* phytase was expressed in and excreted from *Aspergillus oryzae* IFO 4177.

Filter aid was added to the culture broth which was filtered through a filtration cloth. This solution was further filtered through a Seitz depth filter plate resulting in a clear solution. The filtrate was concentrated by ultrafiltration on 10 kDa cut-off polyethersulphone membranes followed by diafiltration with distilled water to reduce the conductivity. The pH of the concentrated enzyme was adjusted to pH 6.0 and the conductivity was adjusted to that of 10 mM succinic acid/NaOH, pH 6.0 by dilution with deionised water.

The phytase was applied to a Q-sepharose FF column equilibrated in 10 mM succinic acid/NaOH, pH 6.0 and the enzyme was eluted with an increasing linear NaCl gradient (0→0.5M). The phytase activity eluted as a single peak. This peak was pooled and (NH$_4$)$_2$SO$_4$ was added to 2.0M final concentration.

A Butyl Toyopearl 650S column was equilibrated in 2.0M (NH$_4$)$_2$SO$_4$, 10 mM CH$_3$COOH/NaOH, pH 5.5 and the phytase was applied to this column and eluted with a decreasing linear (NH$_4$)$_2$SO$_4$ gradient (2.0→0M). Phytase containing fractions were pooled and the buffer was exchanged for 10 mM succinic acid/NaOH, pH 6.5 on a Sephadex G25 column. The G25 filtrate was applied to a Q-sepharose FF column equilibrated in 10 mM succinic acid/NaOH, pH 6.5. After washing the column extensively with the equilibration buffer, the phytase was eluted with an increasing linear NaCl gradient (0→0.3M). The phytase activity was pooled and the buffer was exchanged for 10 mM succinic acid/NaOH, pH 7.0 on a Sephadex G25 column. The G25 filtrate was applied to a SOURCE 30Q column equilibrated in 10 mM succinic acid/NaOH, pH 7.0. After washing the column thoroughly with the equilibration buffer en phytase was eluted with an increasing linear NaCl gradient (0→0.2M). Fractions from the SOURCE 30Q column were analyzed by SDS-PAGE and pure phytase fractions were pooled.

The *Trametes pubescens* phytase migrates on SDS-PAGE as a band with M$_r$=57 kDa. N-terminal amino acid sequencing of the 57 kDa component was carried out following SDS-PAGE and electroblotting onto a PVDF-membrane. The following N-terminal amino acid sequence could be deduced.

Xxx-Ala-Cys-Leu-Asp-Val-Thr-Arg-Asp-(Ala/Val)-Gln-

The sequence corresponds to amino acid residues 31–41 in the cDNA derived amino acid sequence.

Accordingly a mature amino acid sequence of the phytase when expressed in Aspergillus is supposed to be no. 31–443 of SEQ ID no. 30. Accordingly, the predicted signal peptide at FIG. 5 does not correspond with the actual signalpeptide when this phytase is expressed in Aspergillus. This is also so for the indications regarding mature peptide of the sequence listing under the headings SEQ ID NOs: 29 and 30.

The molecular weights (kDa) of the three phytases of *Trametes pubescens* and PhyA2 and PhyA1 of *Paxillus involtus* are 65, 55 and 65 kDa, respectively.

The pH profiles of these three phytases are similar to FIGS. 8 and 23 for the Peniophora and the Agrocybe phytases (optimum pH around 5–6; very little activity at pH above 7). As compared to the known phytase of *Aspergillus ficuum* (in this test having a temperature optimum of around 50° C.) PhyA1 of *Paxillus involtus* has a slightly higher temperature optimum around 60° C., while PhyA2 has a temperature optimum of around 40° C. The termostability of the PhyA1 phytase of *Paxillus involtus* is comparable to that of the *Aspergillus ficuum* phytase, and better than that of the PhyA2 phytase of *Paxillus involtus* and the phytase of *Trametes pubescens*. Following 60 minutes incubation at 70° C. and 80° C., respectively, the residual activity of PhyA1 is around 60% and 40%, respectively.

In DSC, Td's of around 48° C., 59° C. and 55° C. are found for the phytases PhyA2 and PhyA1 of *Paxillus involtus* and for the phytase of *Trametes pubescens,* respectively.

The specific activities are surprisingly high for all these phytases, viz. 1450, 1370 and 810 FYT/mg enzyme protein for the phytases of *Trametes pubescens, Paxillus involtus* PhyA2 and PhyA1, respectively (A$_{280}$ of 3.58; 5.72 and 3.08; FYT/ml of 5184, 7808 and 2497; assumed extinction coefficient of 1 l/(g×cm), respectively).

We claim:

1. An isolated polypeptide exhibiting phytase activity, said polypeptide comprising an amino acid sequence selected from the group consisting of:

P-[Y/F]-[F/Y]-P-X-X-X-Y-X-X-P-P; (SEQ ID NO: 1)

[Q-V-[N/H]-[I/L]-I-Q-R-H-G-A-R-[F/W]-P-T-S-G-A; (SEQ ID NO: 2)

[I-Q-R-H-G-A-R-[F/W]-P-T-S-G-A-X-X-R; (SEQ ID NO: 3)

[R-V-V-[D/A]-[S/T]-[A/S]-[T/N]-N-W-T-[A/E]-G-F; (SEQ ID NO: 4)

N-W-T-[A/E]-G-F-X-X-A-S; (SEQ ID NO: 5)

G-F-X-X-A-S-X-X-X-X-P; (SEQ ID NO: 6)

P-[N/D]-[P/E]-X-R-[T/L]-[W/F]-X-X-[SIK]-X-X-[V/T]-P-F-S; (SEQ ID NO: 7)

D-[Q/A]-[V/L]-Q-P-L-X-F-C-G-[G/A]; (SEQ ID NO: 8)

F-V-E-S-Q-X-[Y/F]-A-R-X-X-G-X-G-D-F-[E/A]-K-C; (SEQ ID NO: 9)

N-W-T-[A/E]-G-F; (SEQ ID NO: 10)

D-K-[F/Y]-Y-G-T; (SEQ ID NO: 11)

D-L-D-K-[F/Y]-Y-G; (SEQ ID NO: 12)

G-D-F-[A/E]-K; (SEQ ID NO: 13)

and

Q-V-[N/H]-[I/L]-I-Q (SEQ ID NO: 14)

wherein "X" denotes any amino acid.

2. The polypeptide according to claim 1, wherein said amino acid sequence is located in the polypeptide at a position corresponding to a position within phyA of *P. lycii* of:

SEQ ID NO: 1: position 46 to 57
SEQ ID NO: 2: position 64 to 80
SEQ ID NO: 3: position 68 to 83
SEQ ID NO: 4: position 155 to 167
SEQ ID NO: 5: position 162 to 171
SEQ ID NO: 6: position 166 to 177
SEQ ID NO: 7: position 358 to 373
SEQ ID NO: 8: position 395 to 405
SEQ ID NO: 9: position 415 to 433
SEQ ID NO: 10: position 162 to 167
SEQ ID NO: 11: position 273 to 278
SEQ ID NO: 12: position 271 to 277
SEQ ID NO: 13: position 428 to 432
SEQ ID NO: 14: position 64 to 69.

3. The polypeptide according to claim 2, said polypeptide comprising a set of amino acid sequences selected from the group consisting of:

SEQ ID NO: 10 and SEQ ID NO: 12;
SEQ ID NO: 10 and SEQ ID NO: 13;
SEQ ID NO: 14 and SEQ ID NO: 10;
SEQ ID NO: 14 and SEQ ID NO: 12;
SEQ ID NO: 14 and SEQ ID NO: 13; and
SEQ ID NO: 11 and SEQ ID NO: 13.

4. The polypeptide according to claim 1, wherein said polypeptide comprises (a) 10 amino acid residues in a sequence corresponding to residues P16 and P27 of SEQ ID NO:24;
(b) 9 amino acid residues between in a sequence corresponding to residues F137–P147 of SEQ ID NO:24;
(c) 10 amino acid residues between in a sequence corresponding to residues P147–N158 of SEQ ID NO:24;
(d) 6 amino acid residues between in a sequence corresponding to residues C166–D173 of SEQ ID NO:24; or
(e) 17 amino acid residues between in a sequence corresponding to residues L323–P341 of SEQ ID NO:24.

5. The polypeptide according to claim 1, which comprises a sequence selected from the group consisting of: (i) residues −26–427 of SEQ ID NO:22; (ii) residues −2–427 of SEQ ID NO:22; (iii) residues 1–427 of SEQ ID NO:22; (iv) residues 2–427 of SEQ ID NO:22; and (v) residues 5–427 of SEQ ID NO:22.

6. The polypeptide according to claim 1, which is encoded by
   (i) a nucleic acid selected from the group consisting of nucleotides 17–1375, 89–1375, 95–1375, 98–1375, and 107–1375 of SEQ ID NO:21; or
   (ii) the DNA sequence cloned into plasmid pYES 2.0 present in *Escherichia coli* DSM 11313.

7. The polypeptide according to claim 1, which comprises residues −19–423, 1–423, or 2–423 of SEQ ID NO:26.

8. The polypeptide according to claim 1, which is encoded by
   (i) a nucleic acid selected from the group consisting of nucleotides 58–1383, 115–1383, and 118–1383 of SEQ ID NO 25; or
   (ii) the DNA sequence cloned into plasmid pYES 2.0 present in *Escherichia coli* 11842.

9. The polypeptide according to claim 1, which comprises residues −19–423, 1–423, or 6–423 of SEQ ID NO 28.

10. The polypeptide according to claim 1 which is encoded by
    (i) a nucleic acid selected from the group consisting of nucleotides 48–1373, 105–1373, and 120–1373 of SEQ ID NO 27; or
    (ii) the DNA sequence cloned into plasmid pYES 2.0 present in *Escherichia coli* DSM 11843.

11. The polypeptide according to claim 1 which comprises residues −17–426, 1–426, or 14–426 of SEQ ID NO 30.

12. The polypeptide according to claim 1 which is encoded by
    (i) a nucleic acid selected from the group consisting of nucleotides 79–1407, 130–1407, and 169–1407 of SEQ ID NO 29; or
    (ii) the DNA sequence cloned into plasmid pYES 2.0 present in *Escherichia coli* DSM 11844.

13. A composition comprising at least one polypeptide according to claim 1.

14. The composition according to claim 13 which is an animal feed additive.

15. The composition according to claim 13, further comprising an enzyme selected from the group consisting of: α-galactosidases, β-galactosidases, other phytases, β-glucanases, cellulases, xylosidases, galactanases, endoglucanases, pectinases, pectinesterases, pectin lyases, polygalactuonases, arabinanases, rhamnogalacturonases, rhamnogalacturonan acetyl esterases, rhamnogalacturonan-α-rhamnosidase, pectate lyases, α-galacturonisidases, mannanases, β-mannosidases, mannan acetyl esterases, xylan acetyl esterases, proteases, xylanases, arabinoxylanases, lipases, phospholipases and cutinases.

* * * * *

SEQUENCE LISTING

<160> NUMBER OF SEQ ID NOS: 32

<210> SEQ ID NO 1
<211> LENGTH: 12
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa in position 2 is Tyr or Phe
      Xaa in position 3 is Phe or Tyr
      Xaa in all other positions is any amino acid

<400> SEQUENCE: 1

Pro Xaa Xaa Pro Xaa Xaa Xaa Tyr Xaa Xaa Pro Pro
 1               5                  10

<210> SEQ ID NO 2
<211> LENGTH: 17
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa in position 3 is Asn or His
      Xaa in position 4 is Ile or Leu
      Xaa in position 12 is Phe or Trp

<400> SEQUENCE: 2

Gln Val Xaa Xaa Ile Gln Arg His Gly Ala Arg Xaa Pro Thr Ser Gly
 1               5                  10                  15

Ala

<210> SEQ ID NO 3
<211> LENGTH: 16
<212> TYPE: PRT
<213> ORGANISM: P. lycii
<220> FEATURE:
<221> NAME/KEY: PEPTIDE
<222> LOCATION: (0)...(0)
<223> OTHER INFORMATION: Xaa in position 8 is Phe or Trp
      Xaa in all other positions is any amino acid

<400> SEQUENCE: 3

Ile Gln Arg His Gly Ala Arg Xaa Pro Thr Ser Gly Ala Xaa Xaa Arg
 1               5                  10                  15

<210> SEQ ID NO 4
<211> LENGTH: 13
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa in position 4 is Asp or Ala
      Xaa in position 5 is Ser or Thr
      Xaa in position 6 is Ala or Ser
      Xaa in position 7 is Thr or Asn
      Xaa in position 11 is Ala or Glu

<400> SEQUENCE: 4

Arg Val Val Xaa Xaa Xaa Xaa Asn Trp Thr Xaa Gly Phe
 1               5                  10

<210> SEQ ID NO 5
<211> LENGTH: 10
<212> TYPE: PRT

```
<213> ORGANISM: P. lycii
<220> FEATURE:
<221> NAME/KEY: PEPTIDE
<222> LOCATION: (0)...(0)
<223> OTHER INFORMATION: Xaa in position 4 is Ala or Glu
      Xaa in all other positions is any amino acid

<400> SEQUENCE: 5

Asn Trp Thr Xaa Gly Phe Xaa Xaa Ala Ser
1               5                   10

<210> SEQ ID NO 6
<211> LENGTH: 12
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa is any amino acid

<400> SEQUENCE: 6

Gly Phe Xaa Xaa Ala Ser Xaa Xaa Xaa Xaa Xaa Pro
1               5                   10

<210> SEQ ID NO 7
<211> LENGTH: 16
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa in position 2 is Asn or Asp
      Xaa in position 3 is Pro or Glu
      Xaa in position 6 is Thr or Leu
      Xaa in position 7 is Trp or Phe
      Xaa in position 10 is Ser or Lys
      Xaa in posiiton 13 is Val or Thr
      Xaa in all other positions is any amino acid

<400> SEQUENCE: 7

Pro Xaa Xaa Xaa Arg Xaa Xaa Xaa Xaa Xaa Xaa Xaa Xaa Pro Phe Ser
1               5                   10                  15

<210> SEQ ID NO 8
<211> LENGTH: 11
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa at position 2 is Gln or Ala
      Xaa at position 3 is Val or Leu
      Xaa at position 7 is any amino acid
      Xaa at position 11 is Gly or Ala

<400> SEQUENCE: 8

Asp Xaa Xaa Gln Pro Leu Xaa Phe Cys Gly Xaa
1               5                   10

<210> SEQ ID NO 9
<211> LENGTH: 19
<212> TYPE: PRT
<213> ORGANISM: P. lycii
<220> FEATURE:
<221> NAME/KEY: PEPTIDE
<222> LOCATION: (0)...(0)
<223> OTHER INFORMATION: Xaa at position 7 is Tyr or Phe
      Xaa at position 17 is Glu or Ala
      Xaa in all other positions is any amino acid

<400> SEQUENCE: 9
```

```
Phe Val Glu Ser Gln Xaa Xaa Ala Arg Xaa Xaa Gly Xaa Gly Asp Phe
 1               5                  10                  15

Xaa Lys Cys

<210> SEQ ID NO 10
<211> LENGTH: 6
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa is position 4 is Ala or Glu

<400> SEQUENCE: 10

Asn Trp Thr Xaa Gly Phe
 1               5

<210> SEQ ID NO 11
<211> LENGTH: 6
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa at position 3 is Phe or Tyr

<400> SEQUENCE: 11

Asp Lys Xaa Tyr Gly Thr
 1               5

<210> SEQ ID NO 12
<211> LENGTH: 7
<212> TYPE: PRT
<213> ORGANISM: Peniophora sp,
<220> FEATURE:
<221> NAME/KEY: PEPTIDE
<222> LOCATION: (0)...(0)
<223> OTHER INFORMATION: Xaa at position 5 is Phe or Tyr

<400> SEQUENCE: 12

Asp Leu Asp Lys Xaa Tyr Gly
 1               5

<210> SEQ ID NO 13
<211> LENGTH: 5
<212> TYPE: PRT
<213> ORGANISM: Peniophora sp.
<220> FEATURE:
<221> NAME/KEY: PEPTIDE
<222> LOCATION: (0)...(0)
<223> OTHER INFORMATION: Xaa in position 4 is Ala or Glu

<400> SEQUENCE: 13

Gly Asp Phe Xaa Lys
 1               5

<210> SEQ ID NO 14
<211> LENGTH: 6
<212> TYPE: PRT
<213> ORGANISM: Peniophora sp.
<220> FEATURE:
<223> OTHER INFORMATION: Xaa at position 3 is Asn or His
      Xaa at position 4 is Ile or Leu

<400> SEQUENCE: 14

Gln Val Xaa Xaa Ile Gln
 1               5
```

<210> SEQ ID NO 15
<211> LENGTH: 26
<212> TYPE: DNA
<213> ORGANISM: Peniophora sp.
<220> FEATURE:
<221> NAME/KEY: misc_feature
<222> LOCATION: (0)...(0)
<223> OTHER INFORMATION: n is a, c, g, t

<400> SEQUENCE: 15
cccaagctta aytggacngm nggntt                                        26

<210> SEQ ID NO 16
<211> LENGTH: 23
<212> TYPE: DNA
<213> ORGANISM: Peniophora sp.
<220> FEATURE:
<221> NAME/KEY: misc_feature
<222> LOCATION: (0)...(0)
<223> OTHER INFORMATION: n is a, c, g, t

<400> SEQUENCE: 16
cccaagcttg ayaartwygg nac                                           23

<210> SEQ ID NO 17
<211> LENGTH: 27
<212> TYPE: DNA
<213> ORGANISM: Peniophora sp.
<220> FEATURE:
<221> NAME/KEY: misc_feature
<222> LOCATION: (0)...(0)
<223> OTHER INFORMATION: n is a, c, g, t

<400> SEQUENCE: 17
gctctagacr tarwayttrt cnarrtc                                       27

<210> SEQ ID NO 18
<211> LENGTH: 25
<212> TYPE: DNA
<213> ORGANISM: Peniophora sp.
<220> FEATURE:
<221> NAME/KEY: misc_feature
<222> LOCATION: (0)...(0)
<223> OTHER INFORMATION: n is a, c, g, t

<400> SEQUENCE: 18
gctctagaca yttnkcraar tcncc                                         25

<210> SEQ ID NO 19
<211> LENGTH: 26
<212> TYPE: DNA
<213> ORGANISM: Peniophora sp.
<220> FEATURE:
<221> NAME/KEY: misc_feature
<222> LOCATION: (0)...(0)
<223> OTHER INFORMATION: n is a, c, g, t

<400> SEQUENCE: 19
cccaagcttc argtnmaymt nathca                                        26

<210> SEQ ID NO 20
<211> LENGTH: 27
<212> TYPE: DNA
<213> ORGANISM: Peniophora sp.
<220> FEATURE:
<221> NAME/KEY: misc_feature
<222> LOCATION: (0)...(0)

-continued

```
<223> OTHER INFORMATION: n is a, c, g, t

<400> SEQUENCE: 20
gctctagacr aanccnkcng tccartt                                              27

<210> SEQ ID NO 21
<211> LENGTH: 1501
<212> TYPE: DNA
<213> ORGANISM: Agrocybe pediades
<220> FEATURE:
<221> NAME/KEY: CDS
<222> LOCATION: (17)...(1375)
<223> OTHER INFORMATION:
<220> FEATURE:
<221> NAME/KEY: sig_peptide
<222> LOCATION: (17)...(94)
<221> NAME/KEY: mat_peptide
<222> LOCATION: (95)...(1375)

<400> SEQUENCE: 21
```

| | | | | | | | | | | | | |
|---|---|---|---|---|---|---|---|---|---|---|---|---|
| ggatccgaat tcactt | atg | tcc | ctc | ttc | atc | ggc | ggc | tgt | ttg | ctc | gtg | ttt | 52 |
| | Met | Ser | Leu | Phe | Ile | Gly | Gly | Cys | Leu | Leu | Val | Phe | |
| | −25 | | | | | −20 | | | | | −15 | | |

| tta | cag | gcg | agc | gca | tac | ggc | ggc | gtc | gtg | cag | gcc | aca | ttc | gtg | cag | 100 |
|---|---|---|---|---|---|---|---|---|---|---|---|---|---|---|---|---|
| Leu | Gln | Ala | Ser | Ala | Tyr | Gly | Gly | Val | Val | Gln | Ala | Thr | Phe | Val | Gln | |
| | −10 | | | | | −5 | | | | | | | | 1 | | |

| ccg | ttt | ttc | cct | cca | cag | att | cag | gac | tct | tgg | gca | gct | tat | aca | cca | 148 |
|---|---|---|---|---|---|---|---|---|---|---|---|---|---|---|---|---|
| Pro | Phe | Phe | Pro | Pro | Gln | Ile | Gln | Asp | Ser | Trp | Ala | Ala | Tyr | Thr | Pro | |
| | 5 | | | | | 10 | | | | | 15 | | | | | |

| tat | tat | cct | gtt | cag | gcg | tac | acg | cct | ccc | ccg | aag | gat | tgc | aag | atc | 196 |
|---|---|---|---|---|---|---|---|---|---|---|---|---|---|---|---|---|
| Tyr | Tyr | Pro | Val | Gln | Ala | Tyr | Thr | Pro | Pro | Pro | Lys | Asp | Cys | Lys | Ile | |
| | 20 | | | | | 25 | | | | | 30 | | | | | |

| aca | caa | gtt | aac | att | att | caa | cga | cat | ggt | gcc | cgc | ttt | ccg | aca | tcg | 244 |
|---|---|---|---|---|---|---|---|---|---|---|---|---|---|---|---|---|
| Thr | Gln | Val | Asn | Ile | Ile | Gln | Arg | His | Gly | Ala | Arg | Phe | Pro | Thr | Ser | |
| | 35 | | | | | 40 | | | | | 45 | | | | 50 | |

| ggg | gca | ggc | aca | agg | atc | caa | gca | gct | gtg | aag | aag | ctt | caa | tca | gct | 292 |
|---|---|---|---|---|---|---|---|---|---|---|---|---|---|---|---|---|
| Gly | Ala | Gly | Thr | Arg | Ile | Gln | Ala | Ala | Val | Lys | Lys | Leu | Gln | Ser | Ala | |
| | | | | 55 | | | | | 60 | | | | | 65 | | |

| aaa | acc | tat | acg | gat | cct | cgt | ctc | gac | ttt | ctg | acc | aac | tat | acc | tat | 340 |
|---|---|---|---|---|---|---|---|---|---|---|---|---|---|---|---|---|
| Lys | Thr | Tyr | Thr | Asp | Pro | Arg | Leu | Asp | Phe | Leu | Thr | Asn | Tyr | Thr | Tyr | |
| | | | 70 | | | | | 75 | | | | | 80 | | | |

| acc | ctt | ggt | cac | gac | gat | ctc | gta | ccg | ttt | gga | gcg | ctt | caa | tca | tca | 388 |
|---|---|---|---|---|---|---|---|---|---|---|---|---|---|---|---|---|
| Thr | Leu | Gly | His | Asp | Asp | Leu | Val | Pro | Phe | Gly | Ala | Leu | Gln | Ser | Ser | |
| | | 85 | | | | | 90 | | | | | 95 | | | | |

| caa | gct | gga | gag | gaa | acg | ttt | caa | cga | tac | tcg | ttt | ctg | gtg | tcc | aaa | 436 |
|---|---|---|---|---|---|---|---|---|---|---|---|---|---|---|---|---|
| Gln | Ala | Gly | Glu | Glu | Thr | Phe | Gln | Arg | Tyr | Ser | Phe | Leu | Val | Ser | Lys | |
| | | 100 | | | | | 105 | | | | | 110 | | | | |

| gag | aac | tta | cct | ttt | gta | aga | gct | tcg | agt | tcc | aat | cga | gtc | gtc | gac | 484 |
|---|---|---|---|---|---|---|---|---|---|---|---|---|---|---|---|---|
| Glu | Asn | Leu | Pro | Phe | Val | Arg | Ala | Ser | Ser | Ser | Asn | Arg | Val | Val | Asp | |
| 115 | | | | | 120 | | | | | 125 | | | | | 130 | |

| tca | gct | acc | aac | tgg | acg | gaa | ggt | ttt | tct | gcg | gcc | agt | cac | cac | gtc | 532 |
|---|---|---|---|---|---|---|---|---|---|---|---|---|---|---|---|---|
| Ser | Ala | Thr | Asn | Trp | Thr | Glu | Gly | Phe | Ser | Ala | Ala | Ser | His | His | Val | |
| | | | | 135 | | | | | 140 | | | | | 145 | | |

| ttg | aat | ccc | att | ctc | ttt | gta | atc | ctc | tca | gaa | agt | ctc | aat | gac | acg | 580 |
|---|---|---|---|---|---|---|---|---|---|---|---|---|---|---|---|---|
| Leu | Asn | Pro | Ile | Leu | Phe | Val | Ile | Leu | Ser | Glu | Ser | Leu | Asn | Asp | Thr | |
| | | | 150 | | | | | 155 | | | | | 160 | | | |

| ctt | gac | gat | gcc | atg | tgc | cct | aac | gcg | ggc | tcc | tcc | gac | ccg | cag | act | 628 |
|---|---|---|---|---|---|---|---|---|---|---|---|---|---|---|---|---|
| Leu | Asp | Asp | Ala | Met | Cys | Pro | Asn | Ala | Gly | Ser | Ser | Asp | Pro | Gln | Thr | |
| | | 165 | | | | | 170 | | | | | 175 | | | | |

| ggt | atc | tgg | acc | tcg | ata | tac | ggg | acg | cct | att | gcc | aac | cga | cta | aat | 676 |
|---|---|---|---|---|---|---|---|---|---|---|---|---|---|---|---|---|
| Gly | Ile | Trp | Thr | Ser | Ile | Tyr | Gly | Thr | Pro | Ile | Ala | Asn | Arg | Leu | Asn | |
| | | 180 | | | | | 185 | | | | | 190 | | | | |

| | | | | | | | | | | | | | |
|---|---|---|---|---|---|---|---|---|---|---|---|---|---|
| cag | cag | gct | ccg | ggt | gca | aat | att | aca | gct | gcc | gat | gtg | tcg | aac | ctt | 724 |
| Gln | Gln | Ala | Pro | Gly | Ala | Asn | Ile | Thr | Ala | Ala | Asp | Val | Ser | Asn | Leu |
| 195 | | | | 200 | | | | | 205 | | | | | 210 |

```
cag cag gct ccg ggt gca aat att aca gct gcc gat gtg tcg aac ctt      724
Gln Gln Ala Pro Gly Ala Asn Ile Thr Ala Ala Asp Val Ser Asn Leu
195             200                 205                 210 ata ccg ctt tgc gca ttc gag acg ata gta aag gag acg cca agt cct      772
Ile Pro Leu Cys Ala Phe Glu Thr Ile Val Lys Glu Thr Pro Ser Pro
            215                 220                 225 ttc tgt aat ttg ttc acc ccc gaa gag ttc gca cag ttt gaa tat ttc      820
Phe Cys Asn Leu Phe Thr Pro Glu Glu Phe Ala Gln Phe Glu Tyr Phe
        230                 235                 240 ggt gac ctg gac aag ttc tat ggg aca ggt tat gga caa ccg tta gga      868
Gly Asp Leu Asp Lys Phe Tyr Gly Thr Gly Tyr Gly Gln Pro Leu Gly
    245                 250                 255 cct gtg caa ggt gtc ggc tac atc aat gaa ctt ctt gcc cga ctc aca      916
Pro Val Gln Gly Val Gly Tyr Ile Asn Glu Leu Leu Ala Arg Leu Thr
260                 265                 270 gaa atg cca gtt cga gat aac acc cag acg aac agg aca ctc gac tct      964
Glu Met Pro Val Arg Asp Asn Thr Gln Thr Asn Arg Thr Leu Asp Ser
275                 280                 285                 290 tct ccg ctt aca ttt ccc ctc gac cgc agt atc tac gct gac ctc tcg     1012
Ser Pro Leu Thr Phe Pro Leu Asp Arg Ser Ile Tyr Ala Asp Leu Ser
            295                 300                 305 cac gat aac caa atg atc gcg ata ttt tca gcg atg ggt ctt ttc aac     1060
His Asp Asn Gln Met Ile Ala Ile Phe Ser Ala Met Gly Leu Phe Asn
        310                 315                 320 cag agt tca cct ttg gat ccg tcc ttc ccc aac ccc aag cgt act tgg     1108
Gln Ser Ser Pro Leu Asp Pro Ser Phe Pro Asn Pro Lys Arg Thr Trp
    325                 330                 335 gtc acc agt cgg ctt acg cct ttc agc gcg aga atg gtc act gag cgg     1156
Val Thr Ser Arg Leu Thr Pro Phe Ser Ala Arg Met Val Thr Glu Arg
340                 345                 350 ttg ctg tgt caa agg gat ggg aca ggg agc ggt gga cca tcc agg atc     1204
Leu Leu Cys Gln Arg Asp Gly Thr Gly Ser Gly Gly Pro Ser Arg Ile
355                 360                 365                 370 atg cgg aat gga aat gtg cag acg ttt gtg agg att ctt gtc aac gat     1252
Met Arg Asn Gly Asn Val Gln Thr Phe Val Arg Ile Leu Val Asn Asp
            375                 380                 385 gct tta cag cct ttg aag ttc tgc gga ggg gac atg gat agt ttg tgt     1300
Ala Leu Gln Pro Leu Lys Phe Cys Gly Gly Asp Met Asp Ser Leu Cys
        390                 395                 400 act ctg gaa gcg ttc gtc gag agc cag aag tat gca cga gag gat ggt     1348
Thr Leu Glu Ala Phe Val Glu Ser Gln Lys Tyr Ala Arg Glu Asp Gly
    405                 410                 415 caa ggc gat ttt gaa aaa tgt ttt gat taaatattgc agtatgctca           1395
Gln Gly Asp Phe Glu Lys Cys Phe Asp
    420                 425 gtgagtagac tacagtgcag gccctgtaac tcttgtattg tgtttctgga attcctcgga   1455
gcgtagtttg tagcaaaaaa aaaaaaaaaa aaattcctgc ggccgc                  1501

<210> SEQ ID NO 22
<211> LENGTH: 453
<212> TYPE: PRT
<213> ORGANISM: Agrocybe pediades
<220> FEATURE:
<221> NAME/KEY: SIGNAL
<222> LOCATION: (1)...(26)

<400> SEQUENCE: 22

Met Ser Leu Phe Ile Gly Gly Cys Leu Leu Val Phe Leu Gln Ala Ser
    -25                 -20                 -15
```

-continued

```
Ala Tyr Gly Gly Val Val Gln Ala Thr Phe Val Gln Pro Phe Phe Pro
-10                  -5                   1                    5

Pro Gln Ile Gln Asp Ser Trp Ala Ala Tyr Thr Pro Tyr Tyr Pro Val
         10                  15                  20

Gln Ala Tyr Thr Pro Pro Lys Asp Cys Lys Ile Thr Gln Val Asn
         25                  30              35

Ile Ile Gln Arg His Gly Ala Arg Phe Pro Thr Ser Gly Ala Gly Thr
        40                  45              50

Arg Ile Gln Ala Ala Val Lys Lys Leu Gln Ser Ala Lys Thr Tyr Thr
55                  60              65                  70

Asp Pro Arg Leu Asp Phe Leu Thr Asn Tyr Thr Tyr Thr Leu Gly His
            75              80                  85

Asp Asp Leu Val Pro Phe Gly Ala Leu Gln Ser Ser Gln Ala Gly Glu
            90              95              100

Glu Thr Phe Gln Arg Tyr Ser Phe Leu Val Ser Lys Glu Asn Leu Pro
        105             110             115

Phe Val Arg Ala Ser Ser Asn Arg Val Val Asp Ser Ala Thr Asn
        120             125             130

Trp Thr Glu Gly Phe Ser Ala Ala Ser His His Val Leu Asn Pro Ile
135             140             145             150

Leu Phe Val Ile Leu Ser Glu Ser Leu Asn Asp Thr Leu Asp Asp Ala
                155             160             165

Met Cys Pro Asn Ala Gly Ser Ser Asp Pro Gln Thr Gly Ile Trp Thr
            170             175             180

Ser Ile Tyr Gly Thr Pro Ile Ala Asn Arg Leu Asn Gln Gln Ala Pro
        185             190             195

Gly Ala Asn Ile Thr Ala Ala Asp Val Ser Asn Leu Ile Pro Leu Cys
        200             205             210

Ala Phe Glu Thr Ile Val Lys Glu Thr Pro Ser Pro Phe Cys Asn Leu
215             220             225             230

Phe Thr Pro Glu Glu Phe Ala Gln Phe Glu Tyr Phe Gly Asp Leu Asp
            235             240             245

Lys Phe Tyr Gly Thr Gly Tyr Gly Gln Pro Leu Gly Pro Val Gln Gly
            250             255             260

Val Gly Tyr Ile Asn Glu Leu Leu Ala Arg Leu Thr Glu Met Pro Val
        265             270             275

Arg Asp Asn Thr Gln Thr Asn Arg Thr Leu Asp Ser Ser Pro Leu Thr
280             285             290

Phe Pro Leu Asp Arg Ser Ile Tyr Ala Asp Leu Ser His Asp Asn Gln
295             300             305             310

Met Ile Ala Ile Phe Ser Ala Met Gly Leu Phe Asn Gln Ser Ser Pro
            315             320             325

Leu Asp Pro Ser Phe Pro Asn Pro Lys Arg Thr Trp Val Thr Ser Arg
        330             335             340

Leu Thr Pro Phe Ser Ala Arg Met Val Thr Glu Arg Leu Leu Cys Gln
        345             350             355

Arg Asp Gly Thr Gly Ser Gly Gly Pro Ser Arg Ile Met Arg Asn Gly
        360             365             370

Asn Val Gln Thr Phe Val Arg Ile Leu Val Asn Asp Ala Leu Gln Pro
375             380             385             390

Leu Lys Phe Cys Gly Gly Asp Met Asp Ser Leu Cys Thr Leu Glu Ala
            395             400             405

Phe Val Glu Ser Gln Lys Tyr Ala Arg Glu Asp Gly Gln Gly Asp Phe
```

Glu Lys Cys Phe Asp
        425

<210> SEQ ID NO 23
<211> LENGTH: 1593
<212> TYPE: DNA
<213> ORGANISM: Peniophora lycii
<220> FEATURE:
<221> NAME/KEY: CDS
<222> LOCATION: (123)...(1439)
<221> NAME/KEY: sig_peptide
<222> LOCATION: (123)...(212)
<221> NAME/KEY: mat_peptide
<222> LOCATION: (213)...(1439)

<400> SEQUENCE: 23
ggatccgaat tccatcttct gctctgacct ccatctcgct gagcggccga cgagaaccta      60
ggggctctaa gtccacgtac tatcgccgcg cctgtgaagg ccccatacca gcccttatcg     120 at atg gtt tct tcg gca ttc gca cct tcc atc cta ctt agc ttg atg       167
   Met Val Ser Ser Ala Phe Ala Pro Ser Ile Leu Leu Ser Leu Met
   -30                 -25                 -20 tcg agt ctt gct ttg agc acg cag ttc agc ttt gtt gcg gcg cag cta       215
Ser Ser Leu Ala Leu Ser Thr Gln Phe Ser Phe Val Ala Ala Gln Leu
-15                 -10                 -5                   1 cct atc ccc gca caa aac aca agt aat tgg ggg cct tac gat ccc ttc       263
Pro Ile Pro Ala Gln Asn Thr Ser Asn Trp Gly Pro Tyr Asp Pro Phe
             5                  10                  15 ttt ccc gtc gaa ccg tat gca gct ccg ccg gaa ggg tgc aca gtg aca       311
Phe Pro Val Glu Pro Tyr Ala Ala Pro Pro Glu Gly Cys Thr Val Thr
        20                  25                  30 cag gtc aac ctg att cag agg cac ggc gcg cgt tgg ccc aca tcc ggc       359
Gln Val Asn Leu Ile Gln Arg His Gly Ala Arg Trp Pro Thr Ser Gly
 35                  40                  45 gcg cgg tcg cgg cag gtc gcc gcc gta gcg aag ata caa atg gcg cga       407
Ala Arg Ser Arg Gln Val Ala Ala Val Ala Lys Ile Gln Met Ala Arg
 50                  55                  60                  65 cca ttc acg gat ccc aag tat gag ttc ctc aac gac ttc gtg tac aag       455
Pro Phe Thr Asp Pro Lys Tyr Glu Phe Leu Asn Asp Phe Val Tyr Lys
                 70                  75                  80 ttc ggc gtc gcc gat ctg cta ccg ttc ggg gct aac caa tcg cac caa       503
Phe Gly Val Ala Asp Leu Leu Pro Phe Gly Ala Asn Gln Ser His Gln
             85                  90                  95 acc ggc acc gat atg tat acg cgc tac agt aca cta ttt gag ggc ggg       551
Thr Gly Thr Asp Met Tyr Thr Arg Tyr Ser Thr Leu Phe Glu Gly Gly
        100                 105                 110 gat gta ccc ttt gtg cgc gcg gct ggt gac caa cgc gtc gtt gac tcc       599
Asp Val Pro Phe Val Arg Ala Ala Gly Asp Gln Arg Val Val Asp Ser
    115                 120                 125 tcg acg aac tgg acg gca ggc ttt ggc gat gct tct ggc gag act gtt       647
Ser Thr Asn Trp Thr Ala Gly Phe Gly Asp Ala Ser Gly Glu Thr Val
130                 135                 140                 145 ctc ccg acg ctc cag gtt gtg ctt caa gaa gag ggg aac tgc acg ctc       695
Leu Pro Thr Leu Gln Val Val Leu Gln Glu Glu Gly Asn Cys Thr Leu
                150                 155                 160 tgc aat aat atg tgc ccg aat gaa gtg gat ggt gac gaa tcc aca acg       743
Cys Asn Asn Met Cys Pro Asn Glu Val Asp Gly Asp Glu Ser Thr Thr
            165                 170                 175 tgg ctg ggg gtc ttt gcg ccg aac atc acc gcg cga ttg aac gct gct       791
Trp Leu Gly Val Phe Ala Pro Asn Ile Thr Ala Arg Leu Asn Ala Ala
        180                 185                 190

-continued

```
gcg ccg agt gcc aac ctc tca gac agc gac gcg ctc act ctc atg gat    839
Ala Pro Ser Ala Asn Leu Ser Asp Ser Asp Ala Leu Thr Leu Met Asp
    195                 200                 205 atg tgc ccg ttc gac act ctc agc tcc ggg aac gcc agc ccc ttc tgt    887
Met Cys Pro Phe Asp Thr Leu Ser Ser Gly Asn Ala Ser Pro Phe Cys
210                 215                 220                 225 gac cta ttt acc gcg gag gag tat gtg tcg tac gag tac tac tat gac    935
Asp Leu Phe Thr Ala Glu Glu Tyr Val Ser Tyr Glu Tyr Tyr Tyr Asp
                230                 235                 240 ctc gac aag tac tat ggc acg ggc ccc ggg aac gct ctc ggt cct gtc    983
Leu Asp Lys Tyr Tyr Gly Thr Gly Pro Gly Asn Ala Leu Gly Pro Val
            245                 250                 255 cag ggc gtc gga tac gtc aat gag ctg ctt gca cgc ttg acc ggc caa   1031
Gln Gly Val Gly Tyr Val Asn Glu Leu Leu Ala Arg Leu Thr Gly Gln
        260                 265                 270 gcc gtt cga gac gag acg cag acg aac cgc acg ctc gac agc gac cct   1079
Ala Val Arg Asp Glu Thr Gln Thr Asn Arg Thr Leu Asp Ser Asp Pro
    275                 280                 285 gca aca ttc ccg ctg aac cgt acg ttc tac gcc gac ttc tcg cat gat   1127
Ala Thr Phe Pro Leu Asn Arg Thr Phe Tyr Ala Asp Phe Ser His Asp
290                 295                 300                 305 aac acc atg gtg ccc atc ttt gcg gcg ctc ggg ctc ttc aac gcc acc   1175
Asn Thr Met Val Pro Ile Phe Ala Ala Leu Gly Leu Phe Asn Ala Thr
                310                 315                 320 gcc ctc gac ccg ctg aag ccc gac gag aac agg ttg tgg gtg gac tct   1223
Ala Leu Asp Pro Leu Lys Pro Asp Glu Asn Arg Leu Trp Val Asp Ser
            325                 330                 335 aag ctg gta ccg ttc tct gga cat atg acg gtc gag aag ctg gca tgt   1271
Lys Leu Val Pro Phe Ser Gly His Met Thr Val Glu Lys Leu Ala Cys
        340                 345                 350 tct ggg aag gag gcg gtc agg gtg ctc gtg aac gac gcg gtg cag ccg   1319
Ser Gly Lys Glu Ala Val Arg Val Leu Val Asn Asp Ala Val Gln Pro
    355                 360                 365 ctg gag ttc tgc gga ggt gtt gat ggg gtg tgc gag ctt tcg gct ttc   1367
Leu Glu Phe Cys Gly Gly Val Asp Gly Val Cys Glu Leu Ser Ala Phe
370                 375                 380                 385 gta gag agc cag acg tat gcg cgg gag aat ggg caa ggc gac ttc gcc   1415
Val Glu Ser Gln Thr Tyr Ala Arg Glu Asn Gly Gln Gly Asp Phe Ala
                390                 395                 400 aag tgc ggc ttt gtt ccg tcg gaa tagcgggaga ccgtctatgc tacacagtaa   1469
Lys Cys Gly Phe Val Pro Ser Glu
            405 ttgtgtactc tatagcactg tagctgtact tacaagtcgt agggtacgat cgtacttacg   1529 ctcgtttatt gatccttcct ttaaaaaaaa aaaaaaaaaa aaaaaaaaaa attcctgcgg   1589 ccgc                                                               1593

<210> SEQ ID NO 24
<211> LENGTH: 439
<212> TYPE: PRT
<213> ORGANISM: Peniophora lycii
<220> FEATURE:
<221> NAME/KEY: SIGNAL
<222> LOCATION: (1)...(30)

<400> SEQUENCE: 24

Met Val Ser Ser Ala Phe Ala Pro Ser Ile Leu Leu Ser Leu Met Ser
-30                 -25                 -20                 -15

Ser Leu Ala Leu Ser Thr Gln Phe Ser Phe Val Ala Ala Gln Leu Pro
```

```
                    -10              -5              1
Ile Pro Ala Gln Asn Thr Ser Asn Trp Gly Pro Tyr Asp Pro Phe Phe
            5               10              15

Pro Val Glu Pro Tyr Ala Ala Pro Pro Glu Gly Cys Thr Val Thr Gln
    20              25              30

Val Asn Leu Ile Gln Arg His Gly Ala Arg Trp Pro Thr Ser Gly Ala
35              40              45              50

Arg Ser Arg Gln Val Ala Ala Val Ala Lys Ile Gln Met Ala Arg Pro
            55              60              65

Phe Thr Asp Pro Lys Tyr Glu Phe Leu Asn Asp Phe Val Tyr Lys Phe
            70              75              80

Gly Val Ala Asp Leu Leu Pro Phe Gly Ala Asn Gln Ser His Gln Thr
            85              90              95

Gly Thr Asp Met Tyr Thr Arg Tyr Ser Thr Leu Phe Glu Gly Gly Asp
            100             105             110

Val Pro Phe Val Arg Ala Ala Gly Asp Gln Arg Val Val Asp Ser Ser
115             120             125             130

Thr Asn Trp Thr Ala Gly Phe Gly Asp Ala Ser Gly Glu Thr Val Leu
            135             140             145

Pro Thr Leu Gln Val Val Leu Gln Glu Gly Asn Cys Thr Leu Cys
            150             155             160

Asn Asn Met Cys Pro Asn Glu Val Asp Gly Asp Glu Ser Thr Thr Trp
            165             170             175

Leu Gly Val Phe Ala Pro Asn Ile Thr Ala Arg Leu Asn Ala Ala Ala
            180             185             190

Pro Ser Ala Asn Leu Ser Asp Ser Asp Ala Leu Thr Leu Met Asp Met
195             200             205             210

Cys Pro Phe Asp Thr Leu Ser Ser Gly Asn Ala Ser Pro Phe Cys Asp
            215             220             225

Leu Phe Thr Ala Glu Glu Tyr Val Ser Tyr Glu Tyr Tyr Asp Leu
            230             235             240

Asp Lys Tyr Tyr Gly Thr Gly Pro Gly Asn Ala Leu Gly Pro Val Gln
            245             250             255

Gly Val Gly Tyr Val Asn Glu Leu Leu Ala Arg Leu Thr Gly Gln Ala
260             265             270

Val Arg Asp Glu Thr Gln Thr Asn Arg Thr Leu Asp Ser Asp Pro Ala
275             280             285             290

Thr Phe Pro Leu Asn Arg Thr Phe Tyr Ala Asp Phe Ser His Asp Asn
            295             300             305

Thr Met Val Pro Ile Phe Ala Ala Leu Gly Leu Phe Asn Ala Thr Ala
            310             315             320

Leu Asp Pro Leu Lys Pro Asp Glu Asn Arg Leu Trp Val Asp Ser Lys
            325             330             335

Leu Val Pro Phe Ser Gly His Met Thr Val Glu Lys Leu Ala Cys Ser
            340             345             350

Gly Lys Glu Ala Val Arg Val Leu Val Asn Asp Ala Val Gln Pro Leu
355             360             365             370

Glu Phe Cys Gly Gly Val Asp Gly Val Cys Glu Leu Ser Ala Phe Val
            375             380             385

Glu Ser Gln Thr Tyr Ala Arg Glu Asn Gly Gln Gly Asp Phe Ala Lys
            390             395             400

Cys Gly Phe Val Pro Ser Glu
            405
```

```
<210> SEQ ID NO 25
<211> LENGTH: 1522
<212> TYPE: DNA
<213> ORGANISM: Paxillus involtus
<220> FEATURE:
<221> NAME/KEY: CDS
<222> LOCATION: (58)...(1383)
<221> NAME/KEY: sig_peptide
<222> LOCATION: (58)...(114)
<221> NAME/KEY: mat_peptide
<222> LOCATION: (115)...(1383)

<400> SEQUENCE: 25
ggatccgaat tcggcactcg tacggtcccc cggtctaccc tctgctcgcc ttggaag atg    60
                                                                Met ctc ttc ggt ttc gtc gcc ctc gcc tgt ctc ttg tcc ctc tcc gag gtc      108
Leu Phe Gly Phe Val Ala Leu Ala Cys Leu Leu Ser Leu Ser Glu Val
        -15                 -10                 -5 ctt gcg acc tcc gtg ccc aag aac aca gcg ccg acc ttc ccc att ccg      156
Leu Ala Thr Ser Val Pro Lys Asn Thr Ala Pro Thr Phe Pro Ile Pro
  1               5                  10 gag agt gag cag cgg aac tgg tcc ccg tac tcg ccc tac ttc cct ctt      204
Glu Ser Glu Gln Arg Asn Trp Ser Pro Tyr Ser Pro Tyr Phe Pro Leu
 15              20                  25                  30 gcc gag tac aag gct cct ccg gcg ggc tgc cag atc aac cag gtc aac      252
Ala Glu Tyr Lys Ala Pro Pro Ala Gly Cys Gln Ile Asn Gln Val Asn
              35                  40                  45 atc atc caa aga cat ggt gcc cgg ttc ccg acc tct ggc gcg acc acc      300
Ile Ile Gln Arg His Gly Ala Arg Phe Pro Thr Ser Gly Ala Thr Thr
         50                  55                  60 cgt atc aag gcg ggt ttg acc aag ttg caa ggc gtc cag aac ttt acc      348
Arg Ile Lys Ala Gly Leu Thr Lys Leu Gln Gly Val Gln Asn Phe Thr
     65                  70                  75 gac gcc aaa ttc aac ttc atc aag tcg ttc aag tac gat ctc ggt aac      396
Asp Ala Lys Phe Asn Phe Ile Lys Ser Phe Lys Tyr Asp Leu Gly Asn
 80                  85                  90 tcg gac ctc gtt ccg ttc ggt gca gca cag tcc ttc gac gct ggt cag      444
Ser Asp Leu Val Pro Phe Gly Ala Ala Gln Ser Phe Asp Ala Gly Gln
 95                 100                 105                 110 gag gcc ttc gcc cgc tac tcg aag ctt gtc agc aag aac aac ctg ccg      492
Glu Ala Phe Ala Arg Tyr Ser Lys Leu Val Ser Lys Asn Asn Leu Pro
                115                 120                 125 ttc att cgt gcc gat gga agt gat cgt gtt gtg gat tct gct aca aac      540
Phe Ile Arg Ala Asp Gly Ser Asp Arg Val Val Asp Ser Ala Thr Asn
            130                 135                 140 tgg act gcg ggt ttc gct tcg gca agt cac aac acg gtc cag ccc aag      588
Trp Thr Ala Gly Phe Ala Ser Ala Ser His Asn Thr Val Gln Pro Lys
        145                 150                 155 ctg aac ctg att ctc ccg caa act ggc aat gat acc ctg gaa gat aat      636
Leu Asn Leu Ile Leu Pro Gln Thr Gly Asn Asp Thr Leu Glu Asp Asn
    160                 165                 170 atg tgc cct gct gct ggc gat tct gac ccc cag gtc aac gcg tgg ttg      684
Met Cys Pro Ala Ala Gly Asp Ser Asp Pro Gln Val Asn Ala Trp Leu
175                 180                 185                 190 gct gtt gct ttc cct tcc atc act gca cgg ctc aac gcc gcc gcg ccc      732
Ala Val Ala Phe Pro Ser Ile Thr Ala Arg Leu Asn Ala Ala Ala Pro
                195                 200                 205 tct gtc aac ctc acc gac acg gac gcg ttc aac ctc gtc agt ctc tgc      780
Ser Val Asn Leu Thr Asp Thr Asp Ala Phe Asn Leu Val Ser Leu Cys
            210                 215                 220
```

```
gct ttc ttg aca gtc tcg aag gag aag aag agt gac ttc tgc acc ctg     828
Ala Phe Leu Thr Val Ser Lys Glu Lys Lys Ser Asp Phe Cys Thr Leu
        225                 230                 235 ttc gag ggc atc cct ggc tct ttc gag gcg ttc gcc tat ggt ggc gac     876
Phe Glu Gly Ile Pro Gly Ser Phe Glu Ala Phe Ala Tyr Gly Gly Asp
240                 245                 250 ctt gac aag ttc tac ggt acc ggt tac ggt cag gaa ctc gga ccc gtt     924
Leu Asp Lys Phe Tyr Gly Thr Gly Tyr Gly Gln Glu Leu Gly Pro Val
255                 260                 265                 270 caa ggc gtc ggc tac gtc aac gag ctc atc gcc cgc ctc acc aac tcc     972
Gln Gly Val Gly Tyr Val Asn Glu Leu Ile Ala Arg Leu Thr Asn Ser
                275                 280                 285 gcc gtc cgc gac aac acc cag acg aac cgc aca ctc gac gcc tcg ccc    1020
Ala Val Arg Asp Asn Thr Gln Thr Asn Arg Thr Leu Asp Ala Ser Pro
            290                 295                 300 gta acc ttc ccg ttg aac aag acg ttc tac gcc gat ttc tcc cac gac    1068
Val Thr Phe Pro Leu Asn Lys Thr Phe Tyr Ala Asp Phe Ser His Asp
        305                 310                 315 aac ctc atg gtc gcc gtc ttc tcc gcc atg ggc ctc ttc cgc cag ccc    1116
Asn Leu Met Val Ala Val Phe Ser Ala Met Gly Leu Phe Arg Gln Pro
    320                 325                 330 gcg ccg ctc agc acg tcc gtg ccg aac cca tgg cgc acg tgg cgc acg    1164
Ala Pro Leu Ser Thr Ser Val Pro Asn Pro Trp Arg Thr Trp Arg Thr
335                 340                 345                 350 agc tcc ctc gtc ccc ttc tcc gga cgc atg gtc gtg gaa cgc ctc agc    1212
Ser Ser Leu Val Pro Phe Ser Gly Arg Met Val Val Glu Arg Leu Ser
                355                 360                 365 tgt ttc ggc acg acc aag gtt cgc gtc ctc gtg cag gac cag gtg cag    1260
Cys Phe Gly Thr Thr Lys Val Arg Val Leu Val Gln Asp Gln Val Gln
            370                 375                 380 ccg ctc gag ttc tgc ggg ggt gat agg aac ggg ctg tgc acg ctt gct    1308
Pro Leu Glu Phe Cys Gly Gly Asp Arg Asn Gly Leu Cys Thr Leu Ala
        385                 390                 395 aag ttt gtg gag agc cag acg ttt gcg agg agt gat ggt gcg ggg gac    1356
Lys Phe Val Glu Ser Gln Thr Phe Ala Arg Ser Asp Gly Ala Gly Asp
    400                 405                 410 ttt gag aag tgc ttc gcg acc tcg gcg tgaggatgga cgaacaaaat          1403
Phe Glu Lys Cys Phe Ala Thr Ser Ala
415                 420 taaattgggg tattttatcg tataattatg gtgtgtgtag aacatgggct cggggtcgat  1463
ggtgaaaagc aaggtttat cgtctaaaaa aaaaaaaaaa aaaaaattcc tgcggccgc   1522

<210> SEQ ID NO 26
<211> LENGTH: 442
<212> TYPE: PRT
<213> ORGANISM: Paxillus involtus
<220> FEATURE:
<221> NAME/KEY: SIGNAL
<222> LOCATION: (1)...(19)

<400> SEQUENCE: 26

Met Leu Phe Gly Phe Val Ala Leu Ala Cys Leu Leu Ser Leu Ser Glu
            -15                 -10                  -5

Val Leu Ala Thr Ser Val Pro Lys Asn Thr Ala Pro Thr Phe Pro Ile
             1               5                  10

Pro Glu Ser Glu Gln Arg Asn Trp Ser Pro Tyr Ser Pro Tyr Phe Pro
        15                  20                  25

Leu Ala Glu Tyr Lys Ala Pro Pro Ala Gly Cys Gln Ile Asn Gln Val
30                  35                  40                  45
```

```
Asn Ile Ile Gln Arg His Gly Ala Arg Phe Pro Thr Ser Gly Ala Thr
            50                  55                  60

Thr Arg Ile Lys Ala Gly Leu Thr Lys Leu Gln Gly Val Gln Asn Phe
        65                  70                  75

Thr Asp Ala Lys Phe Asn Phe Ile Lys Ser Phe Lys Tyr Asp Leu Gly
            80                  85                  90

Asn Ser Asp Leu Val Pro Phe Gly Ala Ala Gln Ser Phe Asp Ala Gly
        95                 100                 105

Gln Glu Ala Phe Ala Arg Tyr Ser Lys Leu Val Ser Lys Asn Asn Leu
110                 115                 120                 125

Pro Phe Ile Arg Ala Asp Gly Ser Asp Arg Val Val Asp Ser Ala Thr
                130                 135                 140

Asn Trp Thr Ala Gly Phe Ala Ser Ala Ser His Asn Thr Val Gln Pro
            145                 150                 155

Lys Leu Asn Leu Ile Leu Pro Gln Thr Gly Asn Asp Thr Leu Glu Asp
        160                 165                 170

Asn Met Cys Pro Ala Ala Gly Asp Ser Asp Pro Gln Val Asn Ala Trp
            175                 180                 185

Leu Ala Val Ala Phe Pro Ser Ile Thr Ala Arg Leu Asn Ala Ala Ala
190                 195                 200                 205

Pro Ser Val Asn Leu Thr Asp Thr Asp Ala Phe Asn Leu Val Ser Leu
                210                 215                 220

Cys Ala Phe Leu Thr Val Ser Lys Glu Lys Ser Asp Phe Cys Thr
            225                 230                 235

Leu Phe Glu Gly Ile Pro Gly Ser Phe Glu Ala Phe Ala Tyr Gly Gly
        240                 245                 250

Asp Leu Asp Lys Phe Tyr Gly Thr Gly Tyr Gly Gln Glu Leu Gly Pro
255                 260                 265

Val Gln Gly Val Gly Tyr Val Asn Glu Leu Ile Ala Arg Leu Thr Asn
270                 275                 280                 285

Ser Ala Val Arg Asp Asn Thr Gln Thr Asn Arg Thr Leu Asp Ala Ser
                290                 295                 300

Pro Val Thr Phe Pro Leu Asn Lys Thr Phe Tyr Ala Asp Phe Ser His
            305                 310                 315

Asp Asn Leu Met Val Ala Val Phe Ser Ala Met Gly Leu Phe Arg Gln
        320                 325                 330

Pro Ala Pro Leu Ser Thr Ser Val Pro Asn Pro Trp Arg Thr Trp Arg
        335                 340                 345

Thr Ser Ser Leu Val Pro Phe Ser Gly Arg Met Val Val Glu Arg Leu
350                 355                 360                 365

Ser Cys Phe Gly Thr Thr Lys Val Arg Val Leu Val Gln Asp Gln Val
                370                 375                 380

Gln Pro Leu Glu Phe Cys Gly Gly Asp Arg Asn Gly Leu Cys Thr Leu
            385                 390                 395

Ala Lys Phe Val Glu Ser Gln Thr Phe Ala Arg Ser Asp Gly Ala Gly
        400                 405                 410

Asp Phe Glu Lys Cys Phe Ala Thr Ser Ala
            415                 420

<210> SEQ ID NO 27
<211> LENGTH: 1642
<212> TYPE: DNA
<213> ORGANISM: Paxillus involtus
<220> FEATURE:
<221> NAME/KEY: CDS
```

-continued

```
<222> LOCATION: (48)...(1373)
<221> NAME/KEY: mat_peptide
<222> LOCATION: (105)...(1373)
<221> NAME/KEY: sig_peptide
<222> LOCATION: (48)...(104)

<400> SEQUENCE: 27
```

| | | |
|---|---|---|
| ggatccgaat tccagtcccc aagctaatcc tctgctcgcc ttggaag atg cac ctc<br>                                                                                       Met His Leu | | 56 |
| ggc ttc gtc acc ctc gct tgt ctc ata cac ctc tcc gag gtc ttc gcg<br>Gly Phe Val Thr Leu Ala Cys Leu Ile His Leu Ser Glu Val Phe Ala<br>   -15                     -10                         -5 | | 104 |
| gca tcc gtg ccc cgg aat att gct ccg aag ttc tca att ccg gaa agc<br>Ala Ser Val Pro Arg Asn Ile Ala Pro Lys Phe Ser Ile Pro Glu Ser<br>1               5                     10                     15 | | 152 |
| gag cag cga aac tgg tcg cct tac tct cct tac ttt ccc cta gcc gaa<br>Glu Gln Arg Asn Trp Ser Pro Tyr Ser Pro Tyr Phe Pro Leu Ala Glu<br>              20                     25                     30 | | 200 |
| tac aag gct cct cca gca ggc tgc gag att aac caa gtc aat att atc<br>Tyr Lys Ala Pro Pro Ala Gly Cys Glu Ile Asn Gln Val Asn Ile Ile<br>        35                     40                     45 | | 248 |
| caa cgg cat ggc gca cgg ttc cca acc tcg ggt gcg gcc act cgc atc<br>Gln Arg His Gly Ala Arg Phe Pro Thr Ser Gly Ala Ala Thr Arg Ile<br> 50                     55                     60 | | 296 |
| aag gct ggt tta agc aag ctg caa tcc gtc cag aat ttc acc gac ccc<br>Lys Ala Gly Leu Ser Lys Leu Gln Ser Val Gln Asn Phe Thr Asp Pro<br>65               70                     75                     80 | | 344 |
| aaa ttc gac ttc atc aag tcg ttc aca tac gat ctt ggt act tcc gac<br>Lys Phe Asp Phe Ile Lys Ser Phe Thr Tyr Asp Leu Gly Thr Ser Asp<br>                   85                     90                     95 | | 392 |
| ctc gtg cca ttc ggc gca gca caa tca ttc gat gcc ggc ctg gag gtc<br>Leu Val Pro Phe Gly Ala Ala Gln Ser Phe Asp Ala Gly Leu Glu Val<br>              100                     105                    110 | | 440 |
| ttc gct cgc tat tcg aag ctc gtc agc tcg gac aac ctg cct ttc att<br>Phe Ala Arg Tyr Ser Lys Leu Val Ser Ser Asp Asn Leu Pro Phe Ile<br>          115                     120                    125 | | 488 |
| cgc tca gat ggt agc gat cgt gta gtc gac act gct acg aac tgg act<br>Arg Ser Asp Gly Ser Asp Arg Val Val Asp Thr Ala Thr Asn Trp Thr<br> 130                   135                     140 | | 536 |
| gca ggt ttt gct tcc gcg agc cgc aac gcg atc caa ccc aag ctc gac<br>Ala Gly Phe Ala Ser Ala Ser Arg Asn Ala Ile Gln Pro Lys Leu Asp<br>145               150                     155                    160 | | 584 |
| ttg ata ctt cca caa act ggc aat gac acc ctc gag gac aac atg tgt<br>Leu Ile Leu Pro Gln Thr Gly Asn Asp Thr Leu Glu Asp Asn Met Cys<br>                  165                     170                    175 | | 632 |
| cca gct gct ggc gaa tcc gac cct cag gtc gat gcg tgg ttg gcg tcc<br>Pro Ala Ala Gly Glu Ser Asp Pro Gln Val Asp Ala Trp Leu Ala Ser<br>             180                     185                    190 | | 680 |
| gcc ttc cca tct gtc acc gcg cag ctc aac gct gca gcg cct ggt gcc<br>Ala Phe Pro Ser Val Thr Ala Gln Leu Asn Ala Ala Ala Pro Gly Ala<br>          195                     200                    205 | | 728 |
| aat ctc aca gac gcc gac gcc ttc aac ctc gtc agc ctg tgt ccc ttc<br>Asn Leu Thr Asp Ala Asp Ala Phe Asn Leu Val Ser Leu Cys Pro Phe<br> 210                   215                     220 | | 776 |
| atg aca gtt tcg aag gag cag aag agc gac ttc tgc acg ttg ttc gag<br>Met Thr Val Ser Lys Glu Gln Lys Ser Asp Phe Cys Thr Leu Phe Glu<br>225               230                     235                    240 | | 824 |
| gga atc cct gga tcg ttc gag gcg ttt gcc tat gcc ggc gac ctt gac<br>Gly Ile Pro Gly Ser Phe Glu Ala Phe Ala Tyr Ala Gly Asp Leu Asp<br>                  245                     250                    255 | | 872 |

-continued

```
aag ttc tat ggg acc ggc tat ggc caa gcc ctc gga ccg gtc caa ggc      920
Lys Phe Tyr Gly Thr Gly Tyr Gly Gln Ala Leu Gly Pro Val Gln Gly
            260                 265                 270 gtc ggc tac atc aac gag ctc ctt gca cgc ctg acc aac tcc gca gtg      968
Val Gly Tyr Ile Asn Glu Leu Leu Ala Arg Leu Thr Asn Ser Ala Val
        275                 280                 285 aac gac aac aca cag acg aac cgc aca ctc gac gcc gca cca gac acg     1016
Asn Asp Asn Thr Gln Thr Asn Arg Thr Leu Asp Ala Ala Pro Asp Thr
    290                 295                 300 ttc ccg ctc aac aag acc atg tac gcc gat ttc tca cac gac aac ctc     1064
Phe Pro Leu Asn Lys Thr Met Tyr Ala Asp Phe Ser His Asp Asn Leu
305                 310                 315                 320 atg gtc gcc gtg ttc tcc gcc atg ggc ctc ttc cgc caa tcc gca ccg     1112
Met Val Ala Val Phe Ser Ala Met Gly Leu Phe Arg Gln Ser Ala Pro
                325                 330                 335 ctc agc acg tcc aca ccg gat ccg aac cgc acg tgg ctc acg agc tct     1160
Leu Ser Thr Ser Thr Pro Asp Pro Asn Arg Thr Trp Leu Thr Ser Ser
            340                 345                 350 gtc gtt ccg ttc tcc gcg cgc atg gcc gtc gaa cgc ctc agc tgt gct     1208
Val Val Pro Phe Ser Ala Arg Met Ala Val Glu Arg Leu Ser Cys Ala
        355                 360                 365 ggt acc acg aag gtg cgc gtc ctg gtg cag gac cag gtc cag cca ctc     1256
Gly Thr Thr Lys Val Arg Val Leu Val Gln Asp Gln Val Gln Pro Leu
    370                 375                 380 gag ttc tgc ggc ggc gac cag gat ggg ttg tgc gcg cta gac aag ttc     1304
Glu Phe Cys Gly Gly Asp Gln Asp Gly Leu Cys Ala Leu Asp Lys Phe
385                 390                 395                 400 gtc gag agc cag gcg tat gca cgg agt ggt ggc gca ggt gac ttt gag     1352
Val Glu Ser Gln Ala Tyr Ala Arg Ser Gly Gly Ala Gly Asp Phe Glu
                405                 410                 415 aag tgt ctt gcg acg acg gtg tgagatgggg taatctacgg tgaagcagcg        1403
Lys Cys Leu Ala Thr Thr Val
            420 gagagcctct caacgaatgc aaaggatagg ttcgaggctt acttcatcaa cctatatcat   1463 cataggacaa gcccccccaat agccagactc gtcgtttgac atcgtgtatg aaataaccc   1523 acccacgcac tccgctgcca ctattcgcgt gtatcgcata ctaggcgttt cgcccagtt    1583 gaacatgagc ccattctgtc cccagtgaaa aaaaaaaaaa aaaaaattcc tgcggccgc    1642
```

<210> SEQ ID NO 28
<211> LENGTH: 442
<212> TYPE: PRT
<213> ORGANISM: Paxillus involtus
<220> FEATURE:
<221> NAME/KEY: SIGNAL
<222> LOCATION: (1)...(19)

<400> SEQUENCE: 28

```
Met His Leu Gly Phe Val Thr Leu Ala Cys Leu Ile His Leu Ser Glu
            -15                 -10                  -5

Val Phe Ala Ala Ser Val Pro Arg Asn Ile Ala Pro Lys Phe Ser Ile
                 1               5                  10

Pro Glu Ser Glu Gln Arg Asn Trp Ser Pro Tyr Ser Pro Tyr Phe Pro
            15                  20                  25

Leu Ala Glu Tyr Lys Ala Pro Pro Ala Gly Cys Glu Ile Asn Gln Val
30                  35                  40                  45

Asn Ile Ile Gln Arg His Gly Ala Arg Phe Pro Thr Ser Gly Ala Ala
                50                  55                  60

Thr Arg Ile Lys Ala Gly Leu Ser Lys Leu Gln Ser Val Gln Asn Phe
```

```
                    65                  70                  75
Thr Asp Pro Lys Phe Asp Phe Ile Lys Ser Phe Thr Tyr Asp Leu Gly
                80                  85                  90

Thr Ser Asp Leu Val Pro Phe Gly Ala Ala Gln Ser Phe Asp Ala Gly
 95                 100                 105

Leu Glu Val Phe Ala Arg Tyr Ser Lys Leu Val Ser Ser Asp Asn Leu
110                 115                 120                 125

Pro Phe Ile Arg Ser Asp Gly Ser Asp Arg Val Val Asp Thr Ala Thr
                130                 135                 140

Asn Trp Thr Ala Gly Phe Ala Ser Ala Ser Arg Asn Ala Ile Gln Pro
                145                 150                 155

Lys Leu Asp Leu Ile Leu Pro Gln Thr Gly Asn Asp Thr Leu Glu Asp
                160                 165                 170

Asn Met Cys Pro Ala Ala Gly Glu Ser Asp Pro Gln Val Asp Ala Trp
                175                 180                 185

Leu Ala Ser Ala Phe Pro Ser Val Thr Ala Gln Leu Asn Ala Ala Ala
190                 195                 200                 205

Pro Gly Ala Asn Leu Thr Asp Ala Asp Ala Phe Asn Leu Val Ser Leu
                210                 215                 220

Cys Pro Phe Met Thr Val Ser Lys Glu Gln Lys Ser Asp Phe Cys Thr
                225                 230                 235

Leu Phe Glu Gly Ile Pro Gly Ser Phe Glu Ala Phe Ala Tyr Ala Gly
                240                 245                 250

Asp Leu Asp Lys Phe Tyr Gly Thr Gly Tyr Gly Gln Ala Leu Gly Pro
                255                 260                 265

Val Gln Gly Val Gly Tyr Ile Asn Glu Leu Leu Ala Arg Leu Thr Asn
270                 275                 280                 285

Ser Ala Val Asn Asp Asn Thr Gln Thr Asn Arg Thr Leu Asp Ala Ala
                290                 295                 300

Pro Asp Thr Phe Pro Leu Asn Lys Thr Met Tyr Ala Asp Phe Ser His
                305                 310                 315

Asp Asn Leu Met Val Ala Val Phe Ser Ala Met Gly Leu Phe Arg Gln
                320                 325                 330

Ser Ala Pro Leu Ser Thr Ser Thr Pro Asp Pro Asn Arg Thr Trp Leu
                335                 340                 345

Thr Ser Ser Val Val Pro Phe Ser Ala Arg Met Ala Val Glu Arg Leu
350                 355                 360                 365

Ser Cys Ala Gly Thr Thr Lys Val Arg Val Leu Val Gln Asp Gln Val
                370                 375                 380

Gln Pro Leu Glu Phe Cys Gly Gly Asp Gln Asp Gly Leu Cys Ala Leu
                385                 390                 395

Asp Lys Phe Val Glu Ser Gln Ala Tyr Ala Arg Ser Gly Gly Ala Gly
                400                 405                 410

Asp Phe Glu Lys Cys Leu Ala Thr Thr Val
                415                 420

<210> SEQ ID NO 29
<211> LENGTH: 1536
<212> TYPE: DNA
<213> ORGANISM: Trametes pubescens
<220> FEATURE:
<221> NAME/KEY: CDS
<222> LOCATION: (79)...(1407)
<221> NAME/KEY: mat_peptide
<222> LOCATION: (130)...(1407)
<221> NAME/KEY: sig_peptide
```

<222> LOCATION: (79)...(129)

<400> SEQUENCE: 29

| | | | | | | | | | | | | |
|---|---|---|---|---|---|---|---|---|---|---|---|---|
| ggatccgaat | tcgcccccac | attcgttcca | tcttagcagc | cgtccgcgcc | caggtcttcg | | | | | | | 60 |

| ataaccccc | gcgtgact | atg | gcc | ttc | tca | atc | ttg | gcc | tcg | ctg | ctc | ttc | 111 |
|---|---|---|---|---|---|---|---|---|---|---|---|---|---|
| | | Met | Ala | Phe | Ser | Ile | Leu | Ala | Ser | Leu | Leu | Phe | |
| | | | -15 | | | | | | -10 | | | | |

| gtg | tgt | tat | gca | tac | gcc | agg | gct | gtg | ccc | cgt | gca | cat | atc | ccg | ctc | 159 |
|---|---|---|---|---|---|---|---|---|---|---|---|---|---|---|---|---|
| Val | Cys | Tyr | Ala | Tyr | Ala | Arg | Ala | Val | Pro | Arg | Ala | His | Ile | Pro | Leu | |
| -5 | | | | | | 1 | | | 5 | | | | | | 10 | |

| cgc | gac | acc | tcc | gcg | tgt | cta | gat | gta | aca | cgc | gat | gtg | cag | cag | agc | 207 |
|---|---|---|---|---|---|---|---|---|---|---|---|---|---|---|---|---|
| Arg | Asp | Thr | Ser | Ala | Cys | Leu | Asp | Val | Thr | Arg | Asp | Val | Gln | Gln | Ser | |
| | | | 15 | | | | | 20 | | | | | 25 | | | |

| tgg | tcc | atg | tac | tct | ccc | tat | ttc | ccg | gca | gca | act | tat | gtg | gct | ccg | 255 |
|---|---|---|---|---|---|---|---|---|---|---|---|---|---|---|---|---|
| Trp | Ser | Met | Tyr | Ser | Pro | Tyr | Phe | Pro | Ala | Ala | Thr | Tyr | Val | Ala | Pro | |
| | | | 30 | | | | | 35 | | | | | 40 | | | |

| ccc | gcg | agt | tgc | cag | atc | aat | cag | gtc | cac | atc | atc | caa | cgt | cat | ggt | 303 |
|---|---|---|---|---|---|---|---|---|---|---|---|---|---|---|---|---|
| Pro | Ala | Ser | Cys | Gln | Ile | Asn | Gln | Val | His | Ile | Ile | Gln | Arg | His | Gly | |
| | | 45 | | | | | 50 | | | | | 55 | | | | |

| gca | cgc | ttt | ccc | acg | tct | ggc | gca | gca | aag | cgc | atc | cag | aca | gca | gta | 351 |
|---|---|---|---|---|---|---|---|---|---|---|---|---|---|---|---|---|
| Ala | Arg | Phe | Pro | Thr | Ser | Gly | Ala | Ala | Lys | Arg | Ile | Gln | Thr | Ala | Val | |
| | 60 | | | | | 65 | | | | | 70 | | | | | |

| gcg | aag | ctg | aag | gcc | gcg | tcc | aac | tac | acc | gat | ccc | ctg | ctc | gcg | ttc | 399 |
|---|---|---|---|---|---|---|---|---|---|---|---|---|---|---|---|---|
| Ala | Lys | Leu | Lys | Ala | Ala | Ser | Asn | Tyr | Thr | Asp | Pro | Leu | Leu | Ala | Phe | |
| 75 | | | | | 80 | | | | | 85 | | | | | 90 | |

| gtt | acg | aac | tac | acc | tac | agc | tta | ggt | cag | gac | agc | ctc | gtt | gaa | ctc | 447 |
|---|---|---|---|---|---|---|---|---|---|---|---|---|---|---|---|---|
| Val | Thr | Asn | Tyr | Thr | Tyr | Ser | Leu | Gly | Gln | Asp | Ser | Leu | Val | Glu | Leu | |
| | | | 95 | | | | | 100 | | | | | 105 | | | |

| ggt | gcg | act | cag | tcc | tcc | gaa | gcg | ggc | cag | gag | gca | ttc | acg | cgg | tac | 495 |
|---|---|---|---|---|---|---|---|---|---|---|---|---|---|---|---|---|
| Gly | Ala | Thr | Gln | Ser | Ser | Glu | Ala | Gly | Gln | Glu | Ala | Phe | Thr | Arg | Tyr | |
| | | | 110 | | | | | 115 | | | | | 120 | | | |

| tca | tcc | ctc | gtg | agc | gcg | gac | gag | ctt | ccc | ttc | gtt | cgg | gcg | tcg | ggc | 543 |
|---|---|---|---|---|---|---|---|---|---|---|---|---|---|---|---|---|
| Ser | Ser | Leu | Val | Ser | Ala | Asp | Glu | Leu | Pro | Phe | Val | Arg | Ala | Ser | Gly | |
| | | 125 | | | | | 130 | | | | | 135 | | | | |

| tca | gat | cgc | gtc | gtt | gcg | act | gcc | aac | aac | tgg | act | gca | ggt | ttc | gcg | 591 |
|---|---|---|---|---|---|---|---|---|---|---|---|---|---|---|---|---|
| Ser | Asp | Arg | Val | Val | Ala | Thr | Ala | Asn | Asn | Trp | Thr | Ala | Gly | Phe | Ala | |
| | 140 | | | | | 145 | | | | | 150 | | | | | |

| ctt | gcg | agc | tca | aac | agc | atc | acg | ccc | gtg | ctc | tca | gtc | atc | att | tcc | 639 |
|---|---|---|---|---|---|---|---|---|---|---|---|---|---|---|---|---|
| Leu | Ala | Ser | Ser | Asn | Ser | Ile | Thr | Pro | Val | Leu | Ser | Val | Ile | Ile | Ser | |
| 155 | | | | | 160 | | | | | 165 | | | | | 170 | |

| gaa | gcg | ggc | aat | gac | acc | ctc | gac | gac | aac | atg | tgc | ccc | gct | gca | ggc | 687 |
|---|---|---|---|---|---|---|---|---|---|---|---|---|---|---|---|---|
| Glu | Ala | Gly | Asn | Asp | Thr | Leu | Asp | Asp | Asn | Met | Cys | Pro | Ala | Ala | Gly | |
| | | | 175 | | | | | 180 | | | | | 185 | | | |

| gat | tcg | gat | ccc | cag | gtc | aat | caa | tgg | ctc | gcg | cag | ttc | gca | ccg | ccg | 735 |
|---|---|---|---|---|---|---|---|---|---|---|---|---|---|---|---|---|
| Asp | Ser | Asp | Pro | Gln | Val | Asn | Gln | Trp | Leu | Ala | Gln | Phe | Ala | Pro | Pro | |
| | | 190 | | | | | 195 | | | | | 200 | | | | |

| atg | act | gct | cgc | ctc | aac | gca | ggc | gcg | ccc | ggc | gcg | aac | ctc | acg | gac | 783 |
|---|---|---|---|---|---|---|---|---|---|---|---|---|---|---|---|---|
| Met | Thr | Ala | Arg | Leu | Asn | Ala | Gly | Ala | Pro | Gly | Ala | Asn | Leu | Thr | Asp | |
| | 205 | | | | | 210 | | | | | 215 | | | | | |

| acg | gac | acc | tac | aac | ctg | ctc | acg | cta | tgc | ccg | ttc | gag | act | gta | gcc | 831 |
|---|---|---|---|---|---|---|---|---|---|---|---|---|---|---|---|---|
| Thr | Asp | Thr | Tyr | Asn | Leu | Leu | Thr | Leu | Cys | Pro | Phe | Glu | Thr | Val | Ala | |
| | | 220 | | | | | 225 | | | | | 230 | | | | |

| acc | gag | cgg | cgt | agt | gaa | ttc | tgc | gac | atc | tac | gag | gag | ctg | cag | gcg | 879 |
|---|---|---|---|---|---|---|---|---|---|---|---|---|---|---|---|---|
| Thr | Glu | Arg | Arg | Ser | Glu | Phe | Cys | Asp | Ile | Tyr | Glu | Glu | Leu | Gln | Ala | |
| 235 | | | | | 240 | | | | | 245 | | | | | 250 | |

| gaa | gac | gcc | ttc | gcg | tac | aat | gcc | gat | ctc | gac | aag | ttc | tac | ggc | act | 927 |
|---|---|---|---|---|---|---|---|---|---|---|---|---|---|---|---|---|
| Glu | Asp | Ala | Phe | Ala | Tyr | Asn | Ala | Asp | Leu | Asp | Lys | Phe | Tyr | Gly | Thr | |
| | | | 255 | | | | | 260 | | | | | 265 | | | |

| gga | tac | ggc | cag | ccc | ctc | gga | ccc | gtg | caa | ggc | gtc | ggg | tac | atc | aac | 975 |
|---|---|---|---|---|---|---|---|---|---|---|---|---|---|---|---|---|

-continued

```
Gly Tyr Gly Gln Pro Leu Gly Pro Val Gln Gly Val Gly Tyr Ile Asn
            270                 275                 280 gag ctc atc gcg cgc ctc acc gcg cag aac gtg tcc gac cac acg cag      1023
Glu Leu Ile Ala Arg Leu Thr Ala Gln Asn Val Ser Asp His Thr Gln
            285                 290                 295 acg aac agc aca ctc gac tcc tcg ccc gag acg ttc ccg ctc aac cgc      1071
Thr Asn Ser Thr Leu Asp Ser Ser Pro Glu Thr Phe Pro Leu Asn Arg
300                 305                 310 acg ctc tac gcg gac ttc tcg cac gac aac cag atg gtc gcg atc ttc      1119
Thr Leu Tyr Ala Asp Phe Ser His Asp Asn Gln Met Val Ala Ile Phe
315                 320                 325                 330 tcg gcc atg ggt ctc ttc aac cag tcc gcg ccg ctc gac ccg acg acg      1167
Ser Ala Met Gly Leu Phe Asn Gln Ser Ala Pro Leu Asp Pro Thr Thr
                335                 340                 345 ccc gac ccc gcg cgc acg ttc ctc gtc aag aag atc gtg ccg ttc tcc      1215
Pro Asp Pro Ala Arg Thr Phe Leu Val Lys Lys Ile Val Pro Phe Ser
            350                 355                 360 gcg cgc atg gtc gtc gag cgc ctc gac tgc ggc ggt gcg cag agc gtg      1263
Ala Arg Met Val Val Glu Arg Leu Asp Cys Gly Gly Ala Gln Ser Val
            365                 370                 375 cgc ctg ctc gtg aac gac gca gtg cag ccg ctg gcg ttc tgc ggg gcg      1311
Arg Leu Leu Val Asn Asp Ala Val Gln Pro Leu Ala Phe Cys Gly Ala
        380                 385                 390 gac acg agc ggg gtg tgc acg ctg gac gcg ttt gtc gag agc cag gcg      1359
Asp Thr Ser Gly Val Cys Thr Leu Asp Ala Phe Val Glu Ser Gln Ala
395                 400                 405                 410 tac gcg cgg aac gat ggc gag ggc gac ttc gag aag tgc ttc gcg aca      1407
Tyr Ala Arg Asn Asp Gly Glu Gly Asp Phe Glu Lys Cys Phe Ala Thr
                415                 420                 425 tagttccagg tgtagatacc cggggaagat gtactctcta gacacctcgc atgtacttat    1467
cgattagaaa gagaccctgg ctgctctgcc ctcaaaaaaa aaaaaaaaaa aaaaaattcc    1527
tgcggccgc                                                            1536

<210> SEQ ID NO 30
<211> LENGTH: 443
<212> TYPE: PRT
<213> ORGANISM: Trametes pubescens
<220> FEATURE:
<221> NAME/KEY: SIGNAL
<222> LOCATION: (1)...(17)

<400> SEQUENCE: 30

Met Ala Phe Ser Ile Leu Ala Ser Leu Leu Phe Val Cys Tyr Ala Tyr
        -15                 -10                  -5

Ala Arg Ala Val Pro Arg Ala His Ile Pro Leu Arg Asp Thr Ser Ala
  1               5                  10                  15

Cys Leu Asp Val Thr Arg Asp Val Gln Gln Ser Trp Ser Met Tyr Ser
                 20                  25                  30

Pro Tyr Phe Pro Ala Ala Thr Tyr Val Ala Pro Ala Ser Cys Gln
             35                  40                  45

Ile Asn Gln Val His Ile Ile Gln Arg His Gly Ala Arg Phe Pro Thr
         50                  55                  60

Ser Gly Ala Ala Lys Arg Ile Gln Thr Ala Val Ala Lys Leu Lys Ala
 65                  70                  75

Ala Ser Asn Tyr Thr Asp Pro Leu Leu Ala Phe Val Thr Asn Tyr Thr
 80                  85                  90                  95

Tyr Ser Leu Gly Gln Asp Ser Leu Val Glu Leu Gly Ala Thr Gln Ser
                100                 105                 110
```

Ser Glu Ala Gly Gln Glu Ala Phe Thr Arg Tyr Ser Ser Leu Val Ser
            115                 120                 125

Ala Asp Glu Leu Pro Phe Val Arg Ala Ser Gly Ser Asp Arg Val Val
        130                 135                 140

Ala Thr Ala Asn Asn Trp Thr Ala Gly Phe Ala Leu Ala Ser Ser Asn
    145                 150                 155

Ser Ile Thr Pro Val Leu Ser Val Ile Ile Ser Glu Ala Gly Asn Asp
160                 165                 170                 175

Thr Leu Asp Asp Asn Met Cys Pro Ala Ala Gly Asp Ser Asp Pro Gln
                180                 185                 190

Val Asn Gln Trp Leu Ala Gln Phe Ala Pro Pro Met Thr Ala Arg Leu
            195                 200                 205

Asn Ala Gly Ala Pro Gly Ala Asn Leu Thr Asp Thr Asp Thr Tyr Asn
        210                 215                 220

Leu Leu Thr Leu Cys Pro Phe Glu Thr Val Ala Thr Glu Arg Arg Ser
    225                 230                 235

Glu Phe Cys Asp Ile Tyr Glu Glu Leu Gln Ala Glu Asp Ala Phe Ala
240                 245                 250                 255

Tyr Asn Ala Asp Leu Asp Lys Phe Tyr Gly Thr Gly Tyr Gly Gln Pro
                260                 265                 270

Leu Gly Pro Val Gln Gly Val Gly Tyr Ile Asn Glu Leu Ile Ala Arg
            275                 280                 285

Leu Thr Ala Gln Asn Val Ser Asp His Thr Gln Thr Asn Ser Thr Leu
        290                 295                 300

Asp Ser Ser Pro Glu Thr Phe Pro Leu Asn Arg Thr Leu Tyr Ala Asp
305                 310                 315

Phe Ser His Asp Asn Gln Met Val Ala Ile Phe Ser Ala Met Gly Leu
320                 325                 330                 335

Phe Asn Gln Ser Ala Pro Leu Asp Pro Thr Thr Pro Asp Pro Ala Arg
                340                 345                 350

Thr Phe Leu Val Lys Lys Ile Val Pro Phe Ser Ala Arg Met Val Val
            355                 360                 365

Glu Arg Leu Asp Cys Gly Gly Ala Gln Ser Val Arg Leu Leu Val Asn
        370                 375                 380

Asp Ala Val Gln Pro Leu Ala Phe Cys Gly Ala Asp Thr Ser Gly Val
385                 390                 395

Cys Thr Leu Asp Ala Phe Val Gly Ser Gln Ala Tyr Ala Arg Asn Asp
400                 405                 410                 415

Gly Glu Gly Asp Phe Glu Lys Cys Phe Ala Thr
                420                 425

<210> SEQ ID NO 31
<211> LENGTH: 276
<212> TYPE: DNA
<213> ORGANISM: Schizophyllum sp.

<400> SEQUENCE: 31
tctgccgcat ctgacggtgt ctataacccc gtcctcaacc tgattatatc agaagagctt     60
aacgacaccc tcgatgatgc gatgtgcccg aacgtcggcg aatcggacgc ccaaacggac    120
gaatggacgt ctatttacgc agcgcccatc gctgagcgtc tgaacaacaa cgccgtgggc    180
gctaacctga ccaccacgaa cgtttacaac ctcatgtctt tatgccccct tcgacacgctt    240 gcgaaggaga cgccgagccc cttctgcgat ctctttt                              276

```
<210> SEQ ID NO 32
<211> LENGTH: 92
<212> TYPE: PRT
<213> ORGANISM: Schizophyllum sp.

<400> SEQUENCE: 32

Ser Ala Ala Ser Asp Gly Val Tyr Asn Pro Val Leu Asn Leu Ile Ile
 1               5                  10                  15

Ser Glu Glu Leu Asn Asp Thr Leu Asp Asp Ala Met Cys Pro Asn Val
             20                  25                  30

Gly Glu Ser Asp Ala Gln Thr Asp Glu Trp Thr Ser Ile Tyr Ala Ala
         35                  40                  45

Pro Ile Ala Glu Arg Leu Asn Asn Asn Ala Val Gly Ala Asn Leu Thr
     50                  55                  60

Thr Thr Asn Val Tyr Asn Leu Met Ser Leu Cys Pro Phe Asp Thr Leu
 65                  70                  75                  80

Ala Lys Glu Thr Pro Ser Pro Phe Cys Asp Leu Phe
                 85                  90
```